(12) United States Patent
Tachdjian et al.

(10) Patent No.: US 9,834,544 B2
(45) Date of Patent: *Dec. 5, 2017

(54) SWEET FLAVOR MODIFIER

(71) Applicant: SENOMYX, INC., San Diego, CA (US)

(72) Inventors: Catherine Tachdjian, San Diego, CA (US); Xiao Qing Tang, San Diego, CA (US); Donald S. Karanewsky, Escondido, CA (US); Guy Servant, San Diego, CA (US); Xiaodong Li, San Diego, CA (US); Feng Zhang, San Diego, CA (US); Qing Chen, San Diego, CA (US); Hong Zhang, San Diego, CA (US); Timothy James Davis, Santee, CA (US); Vincent Darmohusodo, Encinitas, CA (US); Melissa S. Wong, San Diego, CA (US); Victor Selchau, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 14/337,764

(22) Filed: Jul. 22, 2014

(65) Prior Publication Data

US 2015/0141527 A1  May 21, 2015

Related U.S. Application Data

(63) Continuation of application No. 13/572,237, filed on Aug. 10, 2012, now Pat. No. 8,815,956.

(60) Provisional application No. 61/522,806, filed on Aug. 12, 2011.

(51) Int. Cl.
| | |
|---|---|
| C07D 405/12 | (2006.01) |
| A23L 2/60 | (2006.01) |
| C07D 401/12 | (2006.01) |
| C07D 215/54 | (2006.01) |
| C07D 451/06 | (2006.01) |
| A61K 47/22 | (2006.01) |
| C07D 215/42 | (2006.01) |
| A23L 27/00 | (2016.01) |

(52) U.S. Cl.
CPC .............. C07D 405/12 (2013.01); A23L 2/60 (2013.01); A23L 27/88 (2016.08); A61K 47/22 (2013.01); C07D 215/42 (2013.01); C07D 215/54 (2013.01); C07D 401/12 (2013.01); C07D 451/06 (2013.01); A23V 2002/00 (2013.01)

(58) Field of Classification Search
CPC ......... A23L 2/60; A23L 27/88; C07D 401/12; C07D 405/12; C07D 215/54; A23V 2002/00; A61K 47/22

See application file for complete search history.

(56) References Cited

U.S. PATENT DOCUMENTS

| | | |
|---|---|---|
| 4,552,883 A | 11/1985 | Bare |
| 4,904,651 A | 2/1990 | Warawa |
| 4,952,584 A | 8/1990 | Thompson et al. |
| 5,006,535 A | 4/1991 | Ife et al. |
| 5,240,934 A | 8/1993 | Hasegawa et al. |
| 5,475,008 A | 12/1995 | Carling et al. |
| 5,593,997 A | 1/1997 | Dow et al. |
| 5,776,942 A | 7/1998 | Furukawa et al. |
| 6,194,493 B1 | 2/2001 | Stahrfeldt et al. |
| 6,339,077 B1 | 1/2002 | Hofmeister et al. |
| 6,410,529 B1 | 6/2002 | Chan et al. |
| 7,476,399 B2 | 1/2009 | Tachdjian et al. |
| 7,928,111 B2 | 4/2011 | Tachdjian et al. |
| 8,592,592 B2 | 11/2013 | Tachdjian et al. |
| 9,000,054 B2 | 4/2015 | Tachdjian et al. |
| 9,049,878 B2 | 6/2015 | Tachdjian et al. |
| 2005/0009815 A1 | 1/2005 | DeVita et al. |
| 2005/0032158 A1 | 2/2005 | Adler et al. |
| 2005/0084506 A1 | 4/2005 | Tachdjian et al. |
| 2006/0045953 A1 | 3/2006 | Tachdjian et al. |
| 2006/0135552 A1 | 6/2006 | Malherbe et al. |
| 2006/0223843 A1 | 10/2006 | Liu |
| 2007/0104709 A1 | 5/2007 | Li et al. |
| 2008/0026077 A1 | 1/2008 | Hilfinger et al. |
| 2008/0306053 A1 | 12/2008 | Tachjian et al. |
| 2008/0306093 A1 | 12/2008 | Servant et al. |
| 2009/0111834 A1 | 4/2009 | Tachdjian et al. |
| 2009/0292010 A1 | 11/2009 | Shigemura et al. |
| 2010/0273776 A1 | 10/2010 | Lindquist et al. |
| 2012/0252805 A1 | 10/2012 | Chen et al. |
| 2013/0041046 A1 | 2/2013 | Tachdijian et al. |
| 2015/0265711 A1 | 9/2015 | Tachdjian et al. |
| 2016/0251372 A1 | 9/2016 | Tachdjian et al. |

FOREIGN PATENT DOCUMENTS

| | | |
|---|---|---|
| EP | 0 096 995 | 12/1983 |
| EP | 0 245 054 | 11/1987 |
| EP | 0 249 301 | 12/1987 |

(Continued)

OTHER PUBLICATIONS

Anderson, Sep. 2003, The process of structure-based drug design, Chemistry and Biology, 10:787-797.

Thiel, May 2004, Structure-aided drug design's next generation, Nature Biotechnology 22(5):513-519.

Doucet-Personeni et al., 2001, A Structure-Based Design Approach to the Development of Novel, Reversible AChE Inhibitors, J. Med. Chem. 44:3203-3215.

(Continued)

Primary Examiner — Savitha Rao
Assistant Examiner — Angela Brown-Pettigrew
(74) Attorney, Agent, or Firm — Knobbe Martens Olson & Bear LLP

(57) ABSTRACT

The present invention includes compounds having structural formula (I), or salts or solvates thereof. These compounds are useful as sweet flavor modifiers. The present invention also includes compositions comprising the present compounds and methods of enhancing the sweet taste of compositions.

32 Claims, No Drawings

(56) References Cited

FOREIGN PATENT DOCUMENTS

| | | |
|---|---|---|
| GB | 1348259 | 3/1974 |
| GB | 1357449 | 6/1974 |
| JP | 51-48440 | 4/1976 |
| JP | 52-142098 | 11/1977 |
| JP | 57-159784 | 10/1982 |
| JP | 06-199855 | 7/1994 |
| WO | WO 93/10783 | 6/1993 |
| WO | WO 03/037259 | 5/2003 |
| WO | WO 03/045920 | 6/2003 |
| WO | WO 04/004658 | 1/2004 |
| WO | WO 05/015158 | 2/2005 |
| WO | WO 05/077050 | 8/2005 |
| WO | WO 05/086968 | 9/2005 |
| WO | WO 05/123686 | 12/2005 |
| WO | WO 06/002421 | 1/2006 |
| WO | WO 06/007700 | 1/2006 |
| WO | WO 06/053784 | 5/2006 |
| WO | WO 06/097340 | 9/2006 |
| WO | WO 06/124944 | 11/2006 |
| WO | WO 06/125974 | 11/2006 |
| WO | WO 06/138512 | 12/2006 |
| WO | WO 07/126841 | 11/2007 |
| WO | WO 07/147578 | 12/2007 |
| WO | WO 11/106114 | 12/2008 |
| WO | WO 2008/154221 | 12/2008 |
| WO | WO 09/063070 | 5/2009 |
| WO | WO 11/075559 | 6/2011 |
| WO | WO 13/158928 | 10/2013 |
| WO | WO 14/152791 | 9/2014 |
| WO | WO 2005/041684 | 5/2015 |

OTHER PUBLICATIONS

Graves et al., 2002, Discovery of Novel Targets of Quinoline Drugs in the Human Purine Binding Proteome, Mol. Pharmacol. 62(6):1364-1372.

Jensen et al., 1995, Synthesis of 4-Quinolone Derivatives, Acta Chem. Scand. 49:53-56.

West, pp. 358 and 365 in Solid State Chemistry and its Applications, Wiley, New York, (1988).

International Search Report, PCT Appl. No. PCT/US2011/030802, 3 pages (May 26, 2011).

Written Opinion of the International Searching Authority, PCT Appl. No. PCT/US2011/030802, 7 pages (May 26, 2011).

International Search Report dated Nov. 15, 2012 in application No. PCT/US12/050461.

Written Opinion dated Nov. 15, 2012 in application No. PCT/US12/050461.

Extended European Search Report dated Feb. 25, 2015 in patent application No. 12824307.8.

Albrecht, 1972, Antibacterial activity of quinolonecarboxylic acids. II. Synthesis of 1-ethyl-4-quinolone-3-carboxylic acids with fused five-membered heterocyclic rings, Justus Liebigs Annalen der Chemie, 762:55-61.

Antoine et al., 1972, Antibacterial activity of m-dioxino quinolinecarboxylic acids, I, Chimica Therapeutica, 7(6):434-443.

Atechian et al., New vistas in quinolone synthesis, Tetrahedron, 2007, 63(13):2811-2823.

Baker et al., "Irreversible Enzyme Inhibitors. 192. Hydrophobic Bonding to Some Dehydrogenases with 5-Substituted-4-hydroxyquinoline-3-carboxylic Acids", Journal of Medicinal Chemistry, 1972 15(3), p. 237-241.

Caplus Accession No. 1973:159459 and JP 48-026772 (Yamanouchi Pharmaceutical Co., Ltd) Apr. 9, 1973.

Caplus Accession No. 1975:156277 and JP 49-133399 (Daiichi Seiyaku Co., Ltd.) Dec. 21, 1974.

Caplus Accession No. 1976:421338 and JP 51-008298 (Daiichi Seiyaku Co., Ltd) Jan. 23, 1976.

Caplus Accession No. 1978:170156.

Caplus Accession No. 2006:125585 and JP 2006036762 (Taisho Pharmaceutical Co Ltd) Feb. 9, 2006.

CAS Registry No. 933710-66-8, STN Entry date Apr. 30, 2007.

Charvat et al., 1995, Diethyl acetonedicarboxylate—a precursor for the synthesis of new substituted 4-aminoquinolines and fused 4-aminopyridines, Monatshefte fur Chemie, 126:333-340.

Davis "A Search for New Trypanocides. V. Some Derivatives of 10-Phenyl-4:9-diazaphenanthrene.", Journal of the Chemical Society, 1957 p. 828-836.

Fang et al., Hypoglycemic activity and chemical structure of the salicylates, Journal of Pharmaceutical Sciences, 1968, 578(12):2111-2116.

Fujiwara, 2012, Sweeteners interacting with the transmembrane domain of the human sweet-taste receptor induce sweet-taste synergisms in binary mixtures, Food Chemistry, 130:561-568.

Godard et al., "o-Aminoformylquinolines, new heterocyclic synthons", Journal of Heterocyclic Chemistry, 1980 17(3), p. 465-473.

Gressler et al., 2008, Quinolone alkaloids from Waltheria douradinha, Phytochemistry, 69:994-999.

Hayes, Transdisciplinary perspectives on sweetness, Chem. Percept., 1:48-57.

Hirao et al., "Studies on the Synthesis of Quinoline Compounds. IV. Syntheses of 3,3'-Dicarboxy-1,1'-diethyl-4,4'-dioxo-1,1',4,4'-tetrahydropolymethylenedioxydiquinolines", Memoirs of the Kyushu Institute of Technology, Engineering, 1984, No. 14, p. 29-34.

Hoehn et al., Potential antidiabetic agents, Pyrazolo[3,4-b]pyridines, Journal of Medicinal Chemistry, 1973, 16(12):1340-1346.

Iijima et al., "ANDP-2, A Novel Acrinol Degradation Product by Light", Journal of Health Science, 2007 53(6), p. 745-749.

Kripalani et al., "Biotransformation in the monkey of cartazolate (SQ 65,396), a substituted pyrazolopyridine having anxiolytic activity", Xenobiotica, 1981 11(7), p. 481-488.

Lalezari, "Synthesis of 4-Aminothieno [2,3-b]pyridine-5-carboxylic Acids (1).", Journal of Heterocyclic Chemistry, 1979 16(3), p. 603-604.

Li et al., Synthesis of new fluroquinolone NM394, Zhongguo Xinyao Zazhi, 2005 14(1):67-69.

Marecki et al., Aug. 1984, Synthesis of 4-substituted aminoquinoline-3-carboxylates as potential antimicrobial agents, Journal of Pharmaceutical Sciences, 73(8):1141-1143.

O'Donnell et al., A study of the analytical behavior of selected synthetic and naturally occurring quinolone using electrospray ionization ion trap mass spectrometry, liquid chromatography and gas chromatography and the construction of an appropriate database for quinolone characterization, Analytica Chimica Acta, 2006, 572(1):63-76.

Pitt, 2009. Heteroaromatic rings of the future, J. Med. Chem. 52:2952-2963.

Pozharskii et al., 1997, Heterocycles in Life and Society, Wiley, pp. 1-6.

Putz et al., Depth-related alkaloid variation in Mediterranean Aplysina sponges, Zeitschrift fuer Natruforschung, C: Journal of Biosciences, 2009, 64(3/4):279-287.

Santilli et al., "2-Oxo-1,8-naphthyridine-3-carboxylic Acid Derivatives with Potent Gastric Antisecretory Properties", Journal of Medicinal Chemistry, 1987 30(12), p. 2270-2277.

Sapelkin et al., 2005, Screening for protein kinase CK2 inhibitors among 3-carboxy-4-aminoquinoline derivatives, Ukrainica Bioorganica Acta 1, 2(1):28-32.

Schaefer et al., "The synthesis of 4-aminoquinolines by intramolecular Friedel-Crafts reaction", Monatshefte fuer Chemie, 1978 109(3), p. 527-535.

Stanczak et al., "Comparison of pharmacophore cinnoline and quinoline systems on the basis of computer calculation and pharmacological screening of their condensed systems", Pharmazie, 2001 56(6), p. 501-505.

Takahashi, Torizo "Syntheses of heterocyclic compounds of nitrogen. LXXV. 3-Quinolinecarboxylic acid derivatives." Yakugaku Zasshi, 1952 72, 1112-1114.

(56) References Cited

OTHER PUBLICATIONS

Titkova et al., "Synthesis of 4-substituted 3-carbethoxy [carboxy]-1,5-naphthyridines, their properties and biological activity, Khimiko-Farmatsevticheskii Zhurnal", 1982 16(6):699-701.
Veronese et al., Nov. 6, 1995, Tin (IV) chloride-promoted synthesis of 4-aminopyridines and 4-aminoquinolines, Tetrahedron, 51(45):12277-12284.
Zuleski et al., "Tracazolate metabolites in rat tissue, Drug Metabolism and Disposition", 1985, 13(2), p. 139-147.

SWEET FLAVOR MODIFIER

CROSS-REFERENCE TO RELATED APPLICATIONS

This application is a continuation of application Ser. No. 13/572,237, filed Aug. 10, 2012, which claims the benefit of priority to U.S. Provisional Application No. 61/522,806, filed Aug. 12, 2011 and entitled "SWEET FLAVOR MODIFIER". This application is related to U.S. patent application Ser. No. 13/076,632, filed Mar. 31, 2011 and entitled "SWEET FLAVOR MODIFIER", which claims the benefit of priority to U.S. Provisional Patent Application No. 61/320,528, filed Apr. 2, 2010 and entitled "SWEET FLAVOR MODIFIER"; and U.S. Provisional Patent Application No. 61/422,341, filed Dec. 13, 2010 and entitled "SWEET FLAVOR MODIFIER". The contents of these applications are hereby incorporated by reference in their entireties for all purposes

FIELD OF THE INVENTION

The invention relates to compounds suitable for modifying receptors and their ligands associated with chemosensory or chemosensory related sensation or reaction.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to be modulators of the chemosensory receptors in T1R family and/or their ligands and are described in the four patent applications listed below.

(1) U.S. patent application Ser. No. 11/760,592, entitled "Modulation of Chemosensory Receptors and Ligands Associated Therewith", filed Jun. 8, 2007; (2) U.S. patent application Ser. No. 11/836,074, entitled "Modulation of Chemosensory Receptors and Ligands Associated Therewith", filed Aug. 8, 2007; (3) U.S. Patent Application Ser. No. 61/027,410, entitled "Modulation of Chemosensory Receptors and Ligands Associated Therewith", filed Feb. 8, 2008; and (4) International Application No. PCT/US2008/065650, entitled "Modulation of Chemosensory Receptors and Ligands Associated Therewith", filed Jun. 3, 2008. The content of these applications are herein incorporated by reference in their entirety for all purposes.

There is a need in the art to develop novel and inventive compounds suitable for modifying receptors and/or their ligands associated with chemosensory or chemosensory related sensation or reaction.

SUMMARY OF THE INVENTION

In one embodiment, the present invention provides a compound having structural Formula (I):

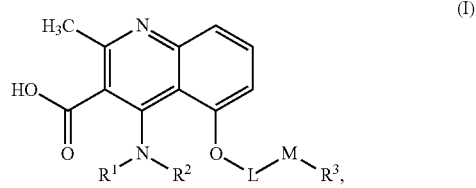

or a salt, solvate, and/or prodrug thereof; wherein
$R^1$ and $R^2$ are independently hydrogen or C1 to C6 alkyl;
L is C1 to C12 alkylene or substituted C1 to C12 alkylene;
M is —$NR^4$—C(O)— or —C(O)—$NR^4$—;
$R^4$ is hydrogen or C1 to C6 alkyl; or alternatively, when M is —$NR^4$—C(O)—, $R^4$ and one or more atoms of L, together with the nitrogen to which they are attached, form a 5- to 8-membered heterocyclic ring containing one to three heteroatoms selected from nitrogen, oxygen, and sulfur; and
$R^3$ is C1 to C12 alkyl, substituted C1 to C12 alkyl, 5- to 8-membered heterocyclyl, or substituted 5- to 8-membered heterocyclyl; or alternatively, when M is —C(O)—$NR^4$—, $R^4$ and one or more atoms of $R^3$, together with the nitrogen to which they are attached, form a 5- to 8-membered heterocyclic ring containing one to three heteroatoms selected from nitrogen, oxygen, and sulfur.

In another embodiment, the present invention provides an ingestible composition comprising a compound of the present invention; and an ingestibly acceptable excipient.

In another embodiment, the present invention provides a method of increasing the sweet taste of an ingestible composition comprising contacting the ingestible composition thereof with a compound of the present invention to form a modified ingestible composition. In the method, the present compound can be a chemosensory receptor modifier, a chemosensory receptor ligand modifier, or both, i.e., a partial chemosensory receptor modifier and partial chemosensory receptor ligand modifier. For example, the present compound can be a sweet receptor agonist, or a sweet enhancer, or a partial sweet receptor agonist and partial sweet enhancer.

In another embodiment, the present invention provides a sweet enhancing composition, comprising a compound of the present invention in an amount effective to provide sweetening in combination with a first amount of sweetener, wherein the sweetening is more than the sweetening provided by the first amount of sweetener without the compound.

In another embodiment, the present invention provides a flavoring concentrate formulation comprising i) as flavor modifying ingredient, a compound of the present invention; ii) a carrier; and iii) optionally at least one adjuvant.

In another embodiment, the present invention provides a method of treating a condition, disease, or disorder associated with a chemosensory receptor comprising administering to a subject in need of such treatment an therapeutically effective amount of a compound of the present invention, or a salt, solvate, and/or prodrug thereof.

DETAILED DESCRIPTION OF THE INVENTION

These and other embodiments, advantages, and features of the present invention are provided in the sections below. Unless defined otherwise, all technical and scientific terms used herein have the same meaning as commonly understood by one of ordinary skill in the art to which this invention belongs.

DEFINITIONS

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_{12}$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined herein below. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-1-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. "Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmnethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," or "Carbocyclyl," by itself or as part of another substituent, refers to a saturated or unsaturated cyclic alkyl radical, as defined herein. Similarly, "Cycloalkylene," or "Carbocyclylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," or "Heterocyclylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Compounds" refers to compounds encompassed by structural formulae disclosed herein, such as (I), (Ia), and (Ib) and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —S—, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —OS$(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC$ (S)OR$^b$, —NR$^b$C(O)NR$^c$R$^c$, —NR$^b$C(NR$^b$)R$^b$ and —NR$^b$C (NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)OR$^b$-alkylene-C(O)NR$^b$R$^b$, and —CH$_2$—CH$_2$—C(O)—CH$_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —R$^a$, halo, —O—, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^b$R$^b$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups useful for substituting nitrogen atoms in heteroalkyl and cycloheteroalkyl groups include, but are not limited to, —R$^a$, —O$^-$, —OR$^b$, —SR$^b$, —S$^-$, —NR$^c$R$^c$, trihalomethyl, —CF$_3$, —CN, —NO, —NO$_2$, —S(O)$_2$R$^b$, —S(O)$_2$O$^-$, —S(O)$_2$OR$^b$, —OS(O)$_2$R$^b$,—OS(O)$_2$O$^-$,—OS (O)$_2$OR$^b$, —P(O)(O$^-$)$_2$, —P(O)(OR$^b$)(O$^-$), —P(O)(OR$^b$) (OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and Re are as previously defined. Substituent groups from the above lists useful for substituting other specified groups or atoms will be apparent to those of skill in the art.

The substituents used to substitute a specified group can be further substituted, typically with one or more of the same or different groups selected from the various groups specified above.

"Treating" or "treatment" of any condition, disease or disorder refers to ameliorating the condition, disease or disorder (i.e., arresting or reducing the development of the condition, disease or disorder or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the condition, disease or disorder, either physically, (e.g., stabilization of a discernible symptom), physiologically, (e.g., stabilization of a physical parameter) or both. In yet other embodiments, "treating" or "treatment" refers to delaying the onset of the condition, disease or disorder.

"Therapeutically effective amount" means the amount of the present compound that, when administered to a patient for treating a condition, disease or disorder, is sufficient to effect such treatment for the condition, disease or disorder. The "therapeutically effective amount" will vary depending on the compound, the condition, disease or disorder and its severity and the age, weight, etc., of the patient to be treated. In one embodiment, the therapeutically effective amount is different from the taste modulating amount, such as a sweet receptor modulating amount, a sweet receptor ligand modulating amount, a sweet flavor modulating amount, a sweet flavoring agent amount, or a sweet flavor enhancing amount.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

According to the present invention, a chemosensory receptor can be any receptor associated with chemosensory sensation or chemosensory ligand triggered signal transduction, e.g., via taste receptors or taste related receptors expressed in taste bud or internal organs of the body, such as gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins. In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

An "enhancer" herein refers to a compound, or an ingestibly acceptable salt or solvate thereof, that modulates (increases) the activation of a particular receptor, preferably the chemosensory, e.g., T1R2/T1R3 receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto. Some enhancers, at its ligand enhancing concentration, do not result in activation of the particular receptor by themselves. That is, the ligand enhancing concentrations of these enhancers are concentration levels of the enhancers that increase or enhance the activation of a particular receptor by a ligand without substantially activating the particular receptor by the enhancers themselves. In some embodiments, certain enhancers, when used at a concentration higher than the ligand enhancing concentration, can also activate a particular receptor by themselves in addition to modulating (e.g., increase or enhancement) the activation of the receptor. For example, certain enhancers, when used at a concentration higher than the ligand enhancing concentration, can be sweeteners (i.e., sweet flavoring agent/entity) as well. In other embodiments, certain enhancers can activate a particular receptor by themselves in addition to modulating (e.g., increase or enhancement) the activation of the receptor simultaneously at the same concentration. In other words, certain enhancers are also sweeteners (i.e., sweet flavoring agent/entity) at the same time.

A "flavor" herein refers to the perception of taste in a subject, which include sweet, sour, salty, bitter and umami. The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "flavor modifier" or "flavor modifying agent" herein refers to a compound or the ingestibly acceptable salt or solvate thereof that modulates, including enhancing or potentiating, and/or inducing, the tastes of a flavoring agent in an animal or a human.

A "flavor enhancer" herein refers to a compound or ingestibly acceptable salt thereof that enhances and/or multiplies the tastes of a flavoring agent, or an ingestible composition comprising the flavoring agent.

A "sweet flavor" refers to the sweet taste typically induced by sugar, such as sucrose, in an animal or a human.

A "sweet flavoring agent", "sweet flavor entity", "sweetener", or "sweet compound" herein refers to a compound or ingestibly acceptable salt thereof that elicits a detectable sweet flavor in a subject, e.g., sucrose or a compound that activates a T1R2/T1R3 receptor in vitro. The subject may be a human or an animal.

A "sweet flavor modifier" or "sweet flavor modifying agent" herein refers to a compound or ingestibly acceptable salt or solvate thereof that modulates, including enhancing or potentiating, inducing, or blocking, the sweet taste of a sweet flavoring agents in an animal or a human. The sweet flavor modifier includes both sweet flavor enhancer and sweet flavoring agent.

A "sweet flavor enhancer" or "sweet flavor enhancing agent" herein refers to an enhancer of a sweet flavor wherein the term enhancer is the same as defined above.

A "sweet receptor activating compound" or "sweet receptor agonist" herein refers to a compound that activates a sweet receptor, such as a T1R2/T1R3 receptor. One example of a sweet receptor activating compound is a sweetener, such as sucrose.

A "sweet receptor modulating compound" herein refers to a compound that modulates (activates, block, or enhances/reduces activation of) a sweet receptor such as a T1R2/T1R3 receptor.

A "sweet receptor enhancing compound" herein refers to a compound that enhances or potentiates the effect of a sweet receptor activating compound, e.g., sucrose.

Although most sweet receptor enhancing compounds or sweet flavor enhancers, at its ligand enhancing concentration of use, do not result in activation of the particular receptor by themselves, some of the sweet receptor enhancing compounds or sweet flavor enhancers, can also activate a particular receptor by themselves in addition to modulating (increase) the activation of the receptor. For example, some of the sweet receptor enhancing compounds or sweet flavor enhancers can also activate a sweet receptor, such as a T1R2/T1R3 receptor, acting as the receptor agonists.

A "sweet flavor modulating amount" herein refers to an amount of a compound of Formula (I) that is sufficient to alter (either increase or decrease) sweet taste in an ingestible composition, or a precursor thereof, sufficiently to be perceived by a human subject. In many embodiments of the invention, at least about 0.001 ppm of the present compound would need to be present in order for most human subjects to perceive a modulation of the sweet flavor of an ingestible composition comprising the present compound. A broad range of concentration that would typically be employed in order to economically provide a desirable degree of sweet flavor modulation can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor enhancing amount" herein refers to an amount of a compound that is sufficient to enhance the taste of flavoring agents, e.g., sucrose, in a ingestible composition, as perceived by an animal or a human. A broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm. In some embodiments, sweet flavor enhancing amount is the amount corresponding to ligand enhancing concentration(s) of a sweet flavor enhancer of the present invention.

A "sweet receptor modulating amount" herein refers to an amount of a compound that is sufficient to modulate (activate, enhance or block) a sweet taste receptor protein. In many embodiments of the invention, a sweet receptor modulating amount is at least about 1 pM, or at least about 1 nM, or at least about 10 nM, or at least about 100 nM (i.e. about 0.1 µM). A "T1R2/T1R3 receptor modulating or activating amount" is an amount of compound that is sufficient to modulate or activate a T1R2/T1R3 receptor. A "sweet receptor" is a taste receptor that can be modulated by a sweet compound. Preferably a sweet receptor is a G protein coupled receptor, and more preferably the sweet receptor is a T1R2/T1R3 receptor.

Compounds

In one embodiment, the present invention provides a compound having structural Formula (I):

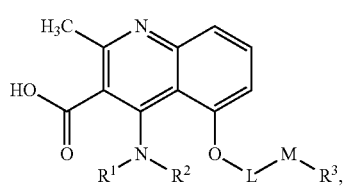

or a salt, solvate, and/or prodrug thereof; wherein
$R^1$ and $R^2$ are independently hydrogen or C1 to C6 alkyl;
L is C1 to C12 alkylene or substituted C1 to C12 alkylene;
M is —$NR^4$—C(O)— or —C(O)—$NR^4$—;
$R^4$ is hydrogen or C1 to C6 alkyl; or alternatively, when M is —$NR^4$—C(O)—, $R^4$ and one or more atoms of L, together with the nitrogen to which they are attached, form a 5- to 8-membered heterocyclic ring which is optionally substituted and contains one to three heteroatoms selected from nitrogen, oxygen, and sulfur; and
$R^3$ is C1 to C12 alkyl, substituted C1 to C12 alkyl, 5- to 8-membered heterocyclyl, or substituted 5- to 8-membered heterocyclyl; or alternatively, when M is —C(O)—$NR^4$—, $R^4$ and one or more atoms of $R^3$, together with the nitrogen to which they are attached, form a 5- to 8-membered heterocyclic ring which is optionally substituted and contains one to three heteroatoms selected from nitrogen, oxygen, and sulfur.

In one embodiment of Formula (I), the substituent group(s) on the C1 to C12 alkylene, the heterocyclyl, the heterocyclic ring, and the C1 to C12 alkyl is selected from the group consisting of halo, amino, N-alkyl amino, N,N-dialkyl amino, hydroxyl, alkoxy, aryl, heteroaryl, heterocyclyl, carbocyclyl, =O, =S, =$NR^a$, =N—$OR^a$, —CN, —OCN, —SCN, —NO, —$NO_2$, =$N_2$, —$N_3$, —C(O)$R^b$, —C(O)$OR^a$, —C(O)$NR^aR^a$, —OC(O)OH, —OC(O)$OR^a$, —$NR^a$C(O)$R^b$, —$NR^a$C(O)$OR^a$, and —$NR^a$C(O)$NR^aR^a$, wherein each $R^a$ is independently hydrogen or alkyl including straight, branched, and cyclic alkyl; or alternatively, two $R^a$, taken together with the nitrogen to which they are attached, form a heterocyclic ring; and each $R^b$ is alkyl including straight, branched, and cyclic alkyl.

In one embodiment of the present invention, Formula (I) does not include the compound species described in U.S. patent application Ser. No. 13/076,632. In one more specific embodiment, Formula (I) does not include compounds listed in Table X below:

TABLE X

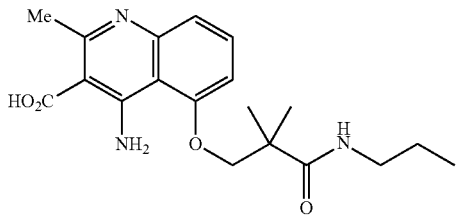 [SMILES: CCCNC(=O)C(C)(C)COc1cccc2nc(C)c(C(=O)O)c(N)c12]

TABLE X-continued

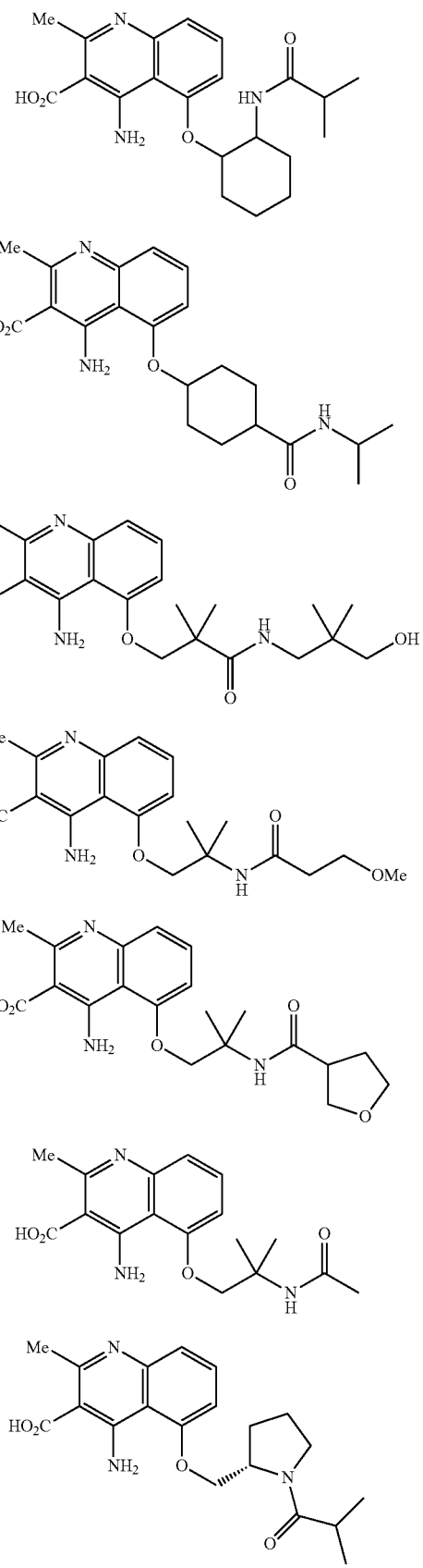

TABLE X-continued
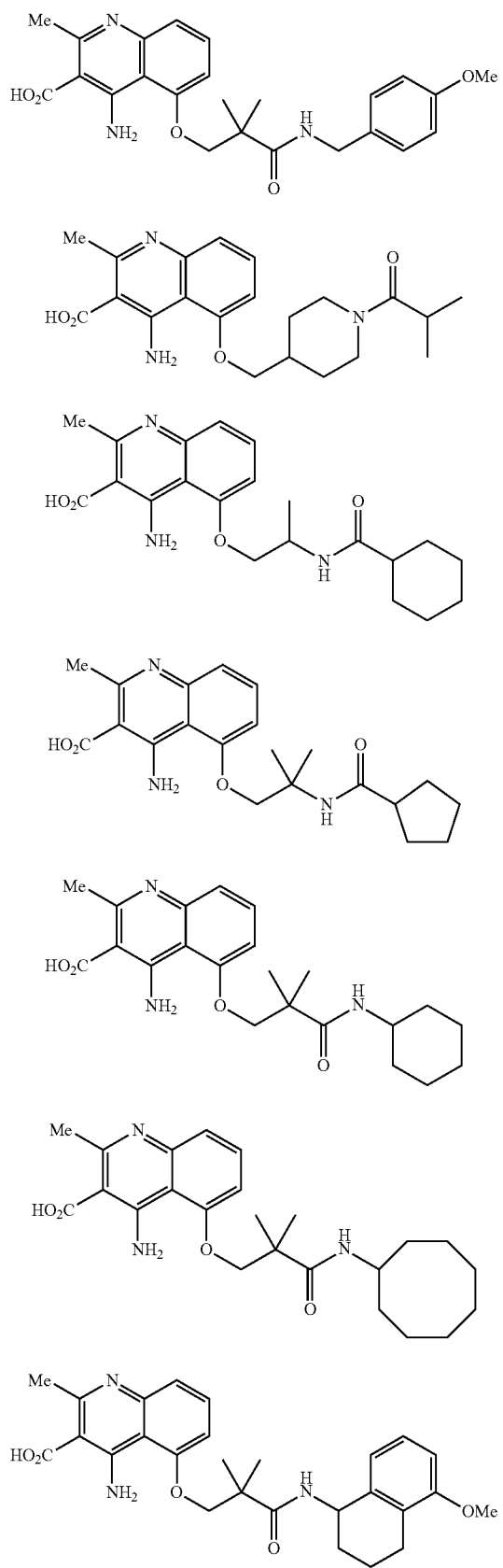
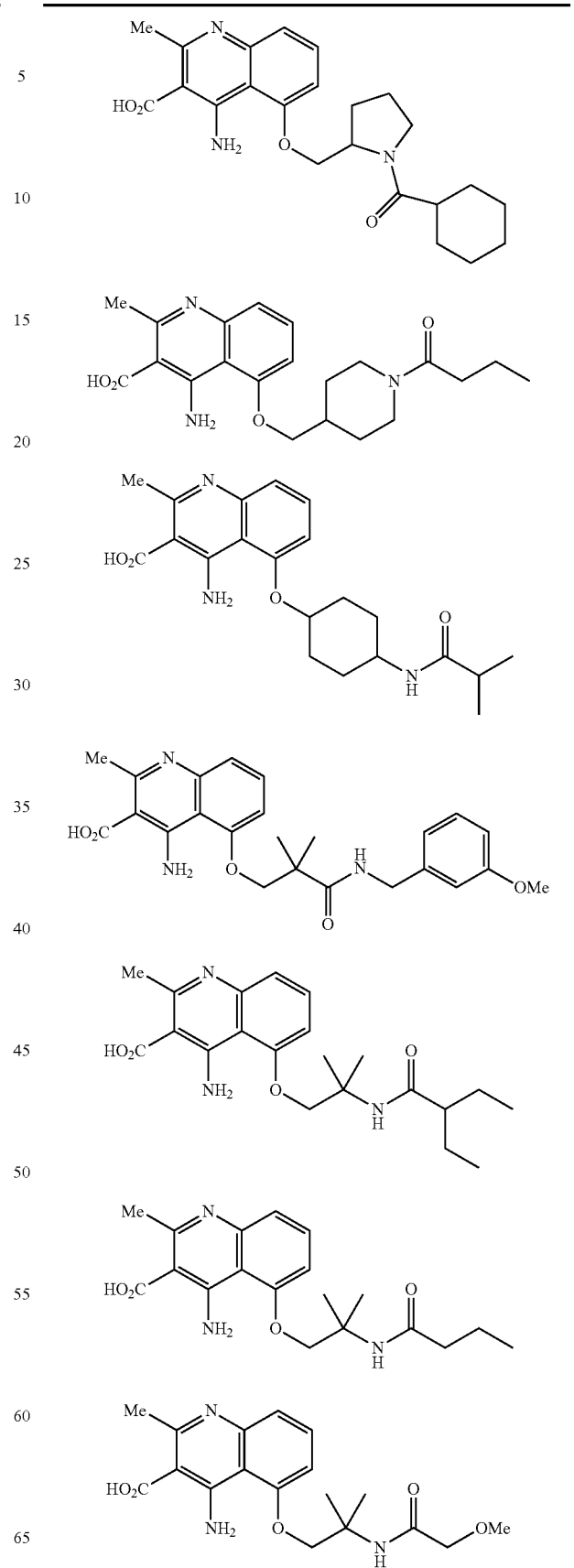

TABLE X-continued

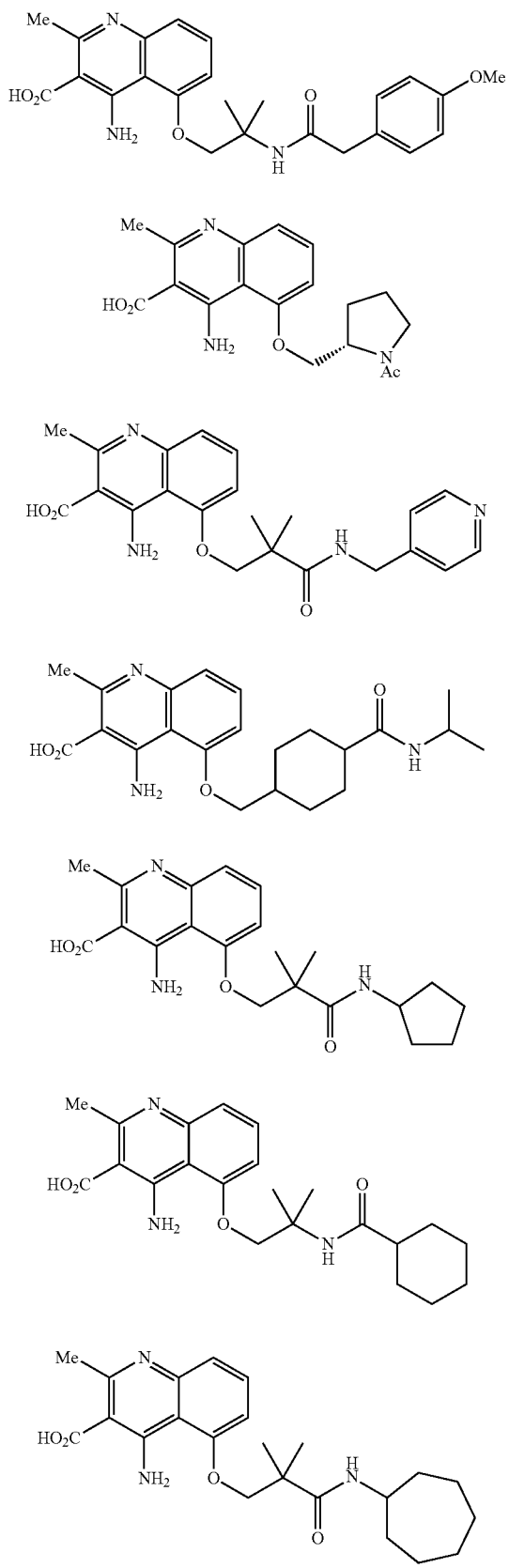

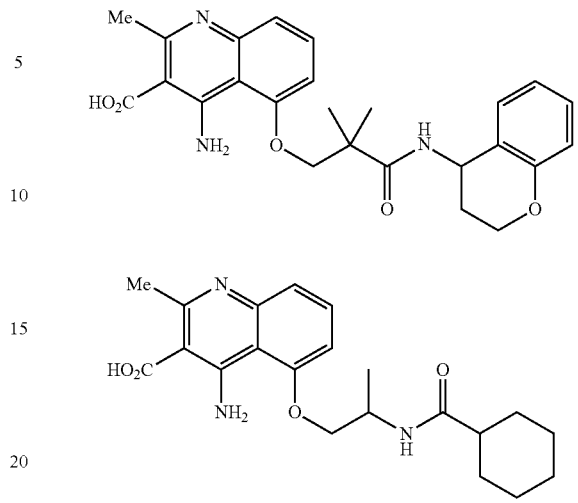

In one embodiment of Formula (I), $R^1$ and $R^2$ are both hydrogen.

In one embodiment of Formula (I), the alkylene is straight, branched, cyclic, or a combination thereof.

In one embodiment of Formula (I), the alkyl is straight, branched, cyclic, or a combination thereof.

In one embodiment of Formula (I), the compound can be represented by structural Formula (Ia):

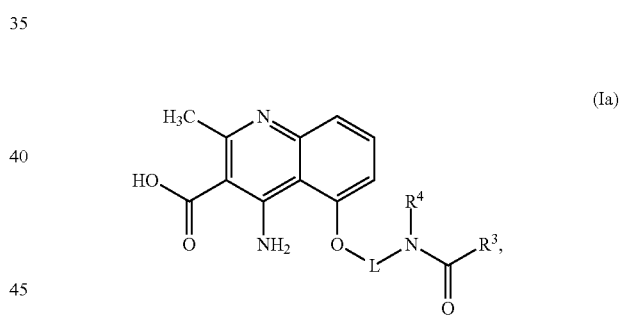

(Ia)

wherein,

L is C1 to C12 alkylene or substituted C1 to C12 alkylene;

$R^4$ is hydrogen or C1 to C6 alkyl; or alternatively, $R^4$ and one or more atoms of L, together with the nitrogen to which they are attached, form a 5- to 8-membered heterocyclic ring containing one to three heteroatoms selected from nitrogen, oxygen, and sulfur; and $R^3$ is C1 to C12 alkyl, substituted C1 to C12 alkyl, 5- to 8-membered heterocyclyl, or substituted 5- to 8-membered heterocyclyl.

In one embodiment of Formula (Ia), L is branched or cyclic C3 to C6 alkylene; $R^4$ is hydrogen; and $R^3$ is branched C3 to C6 alkyl or straight C1 to C6 alkyl.

In one embodiment of Formula (I), the compound can be represented by structural Formula (Ib):

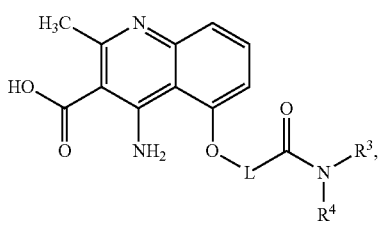

(Ib)

wherein:

L is C1 to C12 alkylene or substituted C1 to C12 alkylene;

R$^4$ is hydrogen or C1 to C6 alkyl; and

R$^3$ is C1 to C12 alkyl, substituted C1 to C12 alkyl, 5- to 8-membered heterocyclyl, substituted 5- to 8-membered heterocyclyl; or alternatively, R$^4$ and one or more atoms of R$^3$, together with the nitrogen to which they are attached, form a 5- to 8-membered heterocyclic ring containing one to three heteroatoms selected from nitrogen, oxygen, and sulfur.

In one embodiment of Formula (Ib), L is straight C1 to C6 alkylene or branched C3 to C6 alkylene; R$^4$ is hydrogen; and R$^3$ is straight C1 to C6 alkyl or branched or cyclic C3 to C6 alkyl.

In certain specific embodiments of Formula (I), the compound is selected from the group consisting of

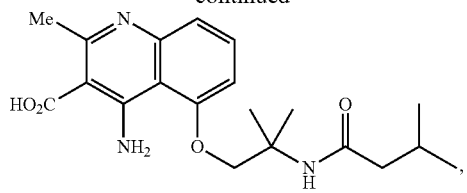

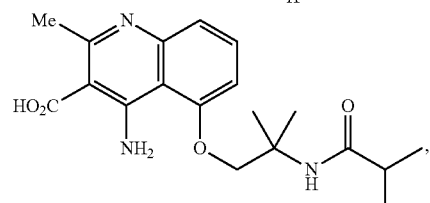

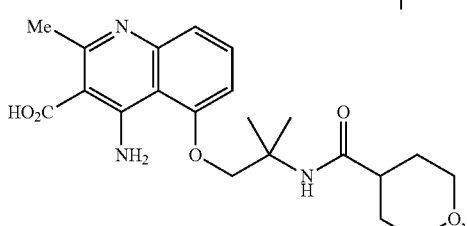

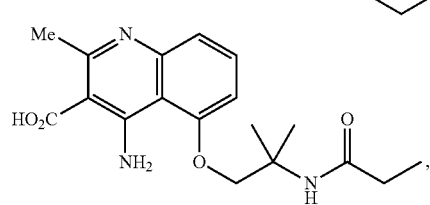

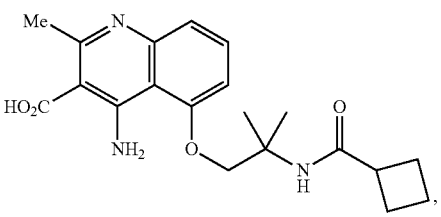

-continued

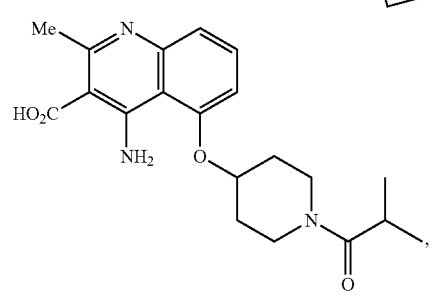

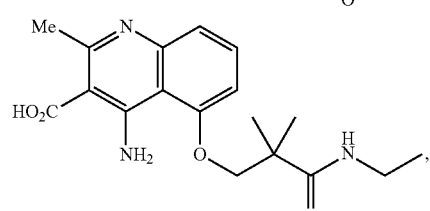

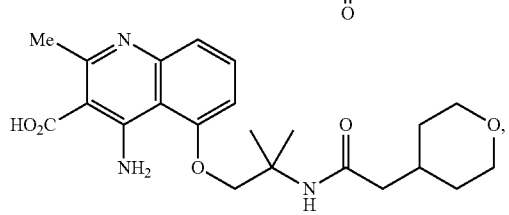

-continued
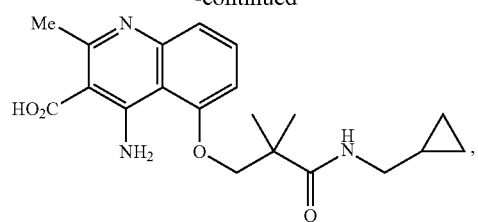
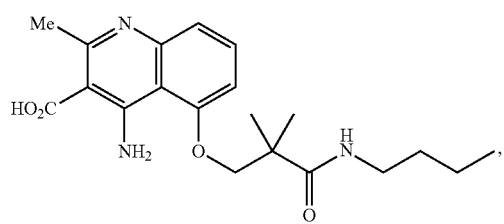
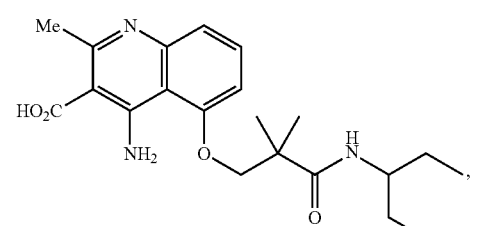
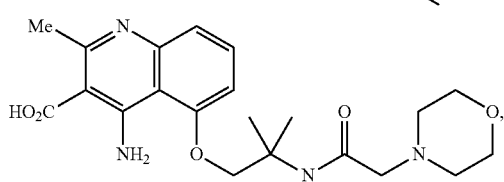
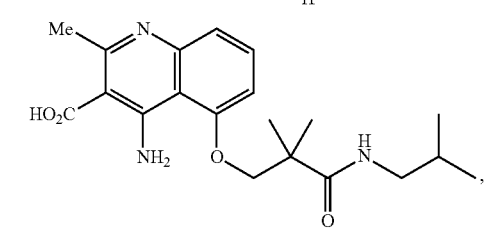
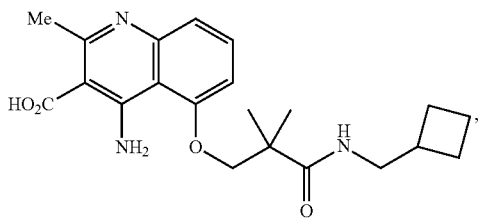
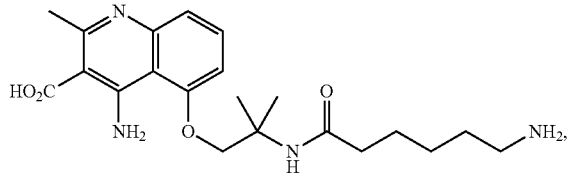
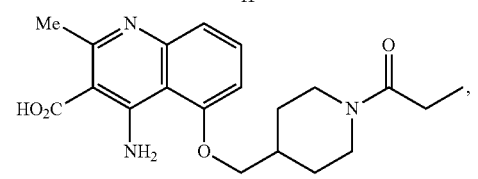
-continued
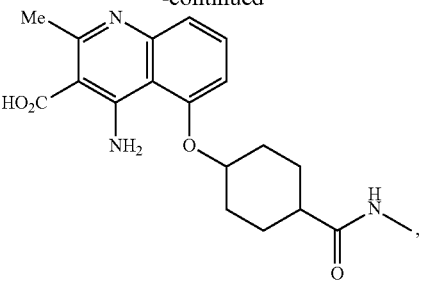
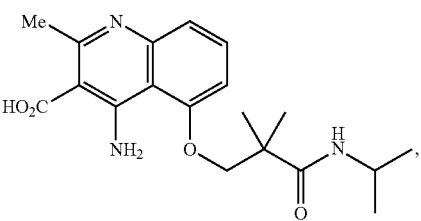
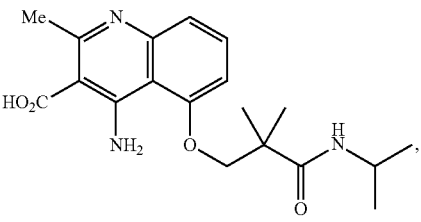
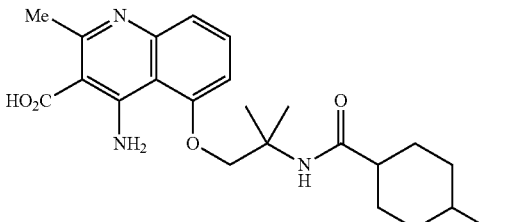
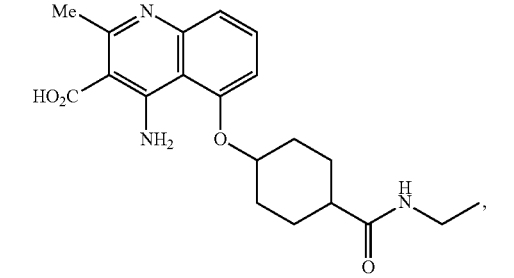
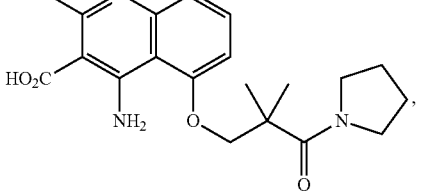
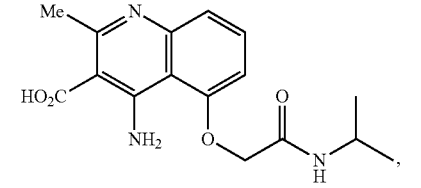

-continued
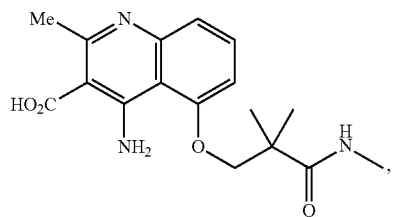
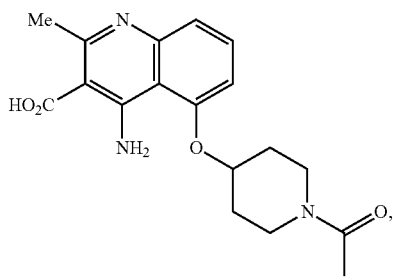
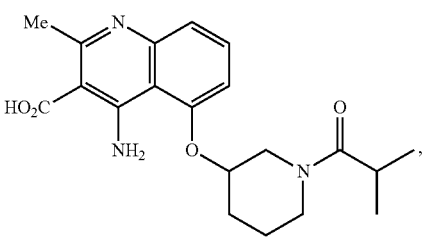
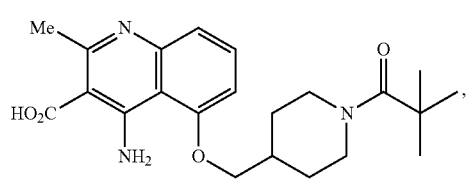
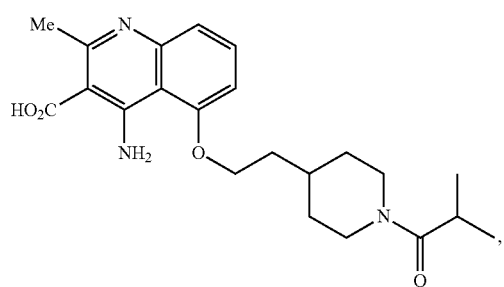
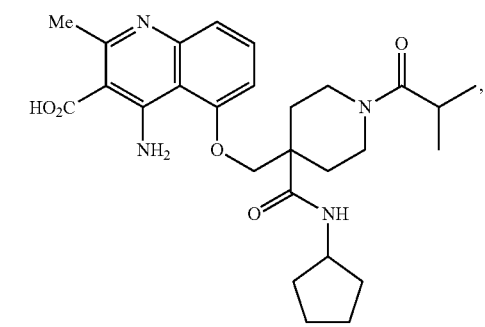
-continued
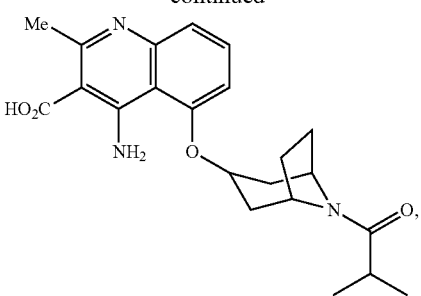
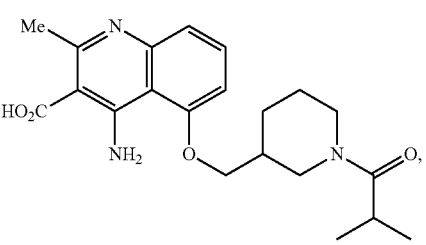
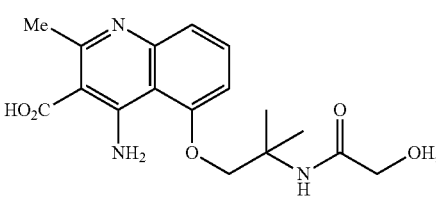
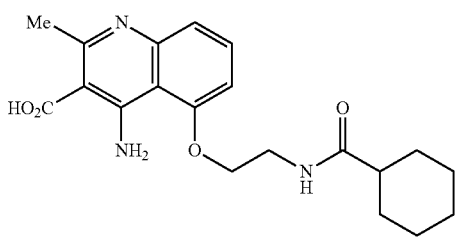
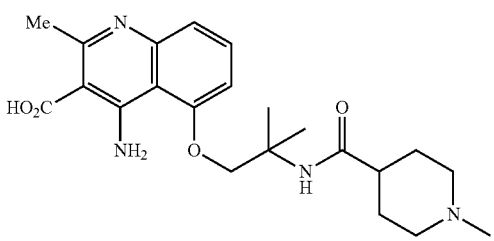
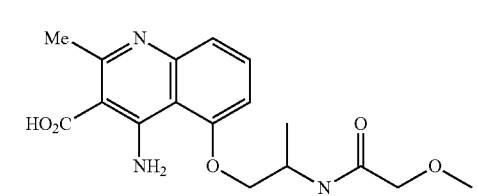
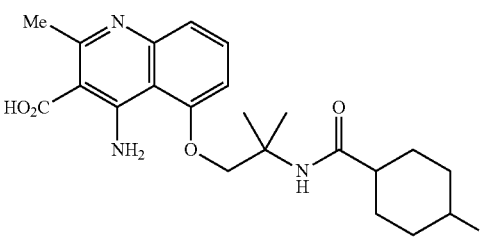

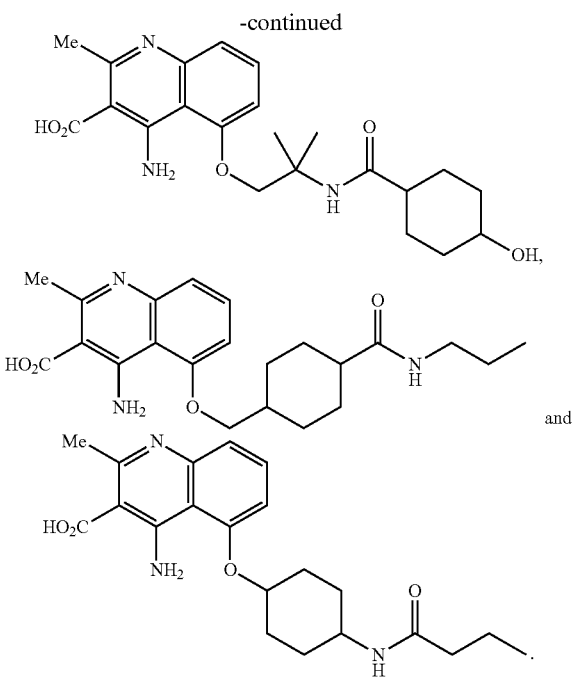

Compositions

The present compounds can be used for one or more methods of the present invention, e.g., modifying receptors and their ligands associated with chemosensory or chemosensory related sensation or reaction. According to the present invention, a method of modulating a chemosensory receptor and/or its ligand includes modulating the activity, structure, function, expression, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g., gastrointestinal disorders, metabolic disorders, functional gastrointestinal disorders, etc. In one embodiment, the method includes increasing or enhancing sweet flavor. In another embodiment, the method includes modulating a sweet receptor and/or its ligand expressed in a place of the body other than the taste buds, such as an internal organ. In general, the compounds of the present invention, individually or in combination, can be provided in a composition, such as, e.g., an ingestible composition. In one embodiment, the present compound can impart a more sugar-like temporal profile and/or flavor profile to a sweetener composition by combining one or more present compound with one or more sweetener in the sweetener composition. In another embodiment, the present compound can increase or enhance the sweet taste of a composition by contacting the composition thereof with one or more present compound to form a modified composition. In another embodiment, the present compound can be in a composition that modulates the sweet receptors and/or their ligands expressed in the body other than in the taste buds.

The compounds of Formula (I), (Ia), and (Ib) and its various subgenuses and species, and their salts and/or solvates, should preferably be comestibly acceptable, e.g., deemed suitable for consumption in food or drink from the perspective of giving unmodified comestible compositions an improved and/or pleasing sweet taste, and would not be significantly toxic or causes unpleasant or undesirable pharmacological or toxicological effects on an animal or human at the typical concentrations they are employed as flavoring agents for the comestible compositions.

One of the methods of demonstrating that a flavorant compound is comestibly acceptable is to have the compound tested and/or evaluated by an Expert Panel of the Flavor and Extract Manufacturers Association (FEMA) and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference. In addition to the FEMA expert panel, an independent, qualified panel of experts in pertinent scientific disciplines may be formed by the manufacturer to evaluate the safety of a specific compound for GRAS status. This process is known as a "self determination of GRAS status." Another method of demonstrating that a flavorant compound is comestibly acceptable is to obtain favorable review by the WHO/FAO Joint Expert Committee on Food Additives, or JECFA. There are also other evaluation methods, such as independent review by the regulatory agency, which are generally known to those of ordinary skill in the food product preparation arts.

In one embodiment, the compounds of the present invention can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment of the present invention, the present compounds can enhance the sweetness of a sweetener under a broad range of pH, e.g., from lower pH to neutral pH. The lower and neutral pH includes, but is not limited to, a pH from about 2.5 to about 8.5; from about 3.0 to about 8.0; from about 3.5 to about 7.5; and from about 4.0 to about 7. In certain embodiments, the present compounds can enhance the perceived sweetness of a fixed concentration of a sweetener in taste tests at a compound concentration of about 50 µM, 40 µM, 30 µM, 20 µM, or 10 µM at both low to neutral pH value. In certain embodiments, the enhancement factor of the present compounds at the lower pH is substantially similar to the enhancement factor of the compounds at neutral pH. Such consistent sweet enhancing property under a broad range of pH render the present compounds good candidates for a broad use in a wide variety of foods and beverages.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

In one embodiment, the present compound is added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In another embodiment, the present compounds are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, enhancing or inhibiting) the sweet taste or other taste properties of other natural or synthetic sweet tastants, and ingestible compositions made therefrom. In one embodiment, the compounds of the present invention is used or provided in its ligand enhancing concentration(s). For example, a broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In one embodiment, the present invention provides a sweet enhancing composition. The sweet enhancing composition comprises a compound of the present invention in an amount effective to provide sweetening, e.g., sweet flavor enhancing amount in combination with a first amount of sweetener, wherein the sweetening is more than the sweetening provided by the first amount of sweetener without the compound.

In one embodiment, the present invention provides an ingestible composition which comprises the sweet enhancing composition of the present invention. In certain embodiments, the present ingestible composition is in the form of a food or beverage product, a pharmaceutical composition, a nutritional product, a dietary supplement, over-the-counter medication, or oral care product.

In one embodiment, the present invention provides a sweetener replacement composition which comprises one or more compounds of the present invention in an amount effective to provide sweetening, e.g., at a concentration higher than their ligand enhancing concentration in the absence of a sweetener, e.g., sucrose other than the present compound(s).

According to another aspect of the invention, the compounds of the present invention are provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacture in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) as flavor modifying ingredient, a compound of the present invention; ii) a carrier; and iii) optionally at least one adjuvant. The term "as flavor modifying ingredient" denotes that the compound of the present invention acts as a flavoring agent or a flavor modifying agent (such as a flavor enhancer) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. The present flavoring concentrate formulation can be carbonated or non-carbonated.

The flavoring concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 3015 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Therapeutic Utilities

In one aspect of the present invention, the present compounds can be used for therapeutic purpose. That is, the present compounds can be used in methods for modulating a chemosensory receptor and/or its ligand to achieve therapeutic effect. For example, the present method includes modulating a chemosensory receptor and/or its ligand expressed in the body other than in the taste buds.

In one embodiment, the method of the present invention, e.g., modulating a chemosensory receptor and/or its ligand includes modulating the expression, secretion, and/or functional level of T1R expressing cells associated with hormone, peptide, enzyme production. In one example, the method of the present invention includes modulating the level of glucose, e.g., inhibitors of a chemosensory receptor such as T1R2 can be used to decrease glucose level (e.g., glucose absorption) in a subject. In another example, the method of the present invention includes modulating the level of incretins, e.g., agonist of a chemosensory receptor such as T1R2 can be used to increase glucagon-like peptide 1 (GLP-1) and thus increase the production of insulin. In yet another example, the method of the present invention includes modulating the expression, secretion, and/or activity level of hormones or peptides produced by T1R expressing cells or gastrointestinal hormone producing cells, e.g., ligands for 5HT receptors (e.g., serotonin), incretins (e.g., GLP-1 and glucose-dependent insulinotropic polypeptide (GIP)), gastrin, secretin, pepsin, cholecystokinin, amylase, ghrelin, leptin, somatostatin, etc. In still another example, the method of the present invention includes modulating the pathways associated with hormones, peptides, and/or enzymes secreted by T1R expressing cells.

In another embodiment, the method of the present invention, e.g., modulating a chemosensory receptor and/or its ligand includes modulating the activity of T1R (e.g., T1R1, T1R2, or T1R3) expressing cells, e.g., liver cells (e.g., hepatocytes, endothelial cells, Kupffer cells, Stellate cells, epithelial cells of bile duct, etc.), heart cells (e.g., endothelial, cardiac, and smooth muscle cells, etc.), pancreatic cells (e.g., alpha cell, beta cell, delta cell, neurosecretory PP cell, D1 cell, etc.), cells in the nipple (e.g., ductal epithelial cells, etc.), stomach cells (e.g., mucous cells, parietal cells, chief cells, G cells, P/D1 cells), intestinal cells (e.g., enteroendocrine cells, brush cells, etc.), salivary gland cells (e.g., Seromucous cells, mucous cells, myoepithelial cells, intercalated duct cell, striated duct cell, etc.), L cells (e.g., expressing GLP-1, etc.), enterochromaffin cells (e.g., expressing serotonin), enterochromaffin-like cells, G cells (e.g., expressing gastrin), D cells (delta cells, e.g., expressing somatostatin), I cells (e.g., expressing cholescystokinin (CCK), K cells (e.g., expressing gastric inhibitory polypeptide), P/D1 cells (e.g., expressing ghrelin), chief cells (e.g., expressing pepsin), and S cells (e.g., expressing secretin). In one example, the method of the present invention includes increasing the expression level of T1R in T1R expressing cells. In another example, the method of the present invention includes increasing the secretion level of T1R expressing cells.

In yet another embodiment, the method of the present invention, e.g., modulating a chemosensory receptor and/or its ligand includes modulation, treatment, and/or prophylactic measure of a condition associated with the gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g., inflammatory or infiltrative disorders, biochemical or genetic abnormalities, endocrine and metabolic disorders, protein-losing enteropathy, etc.), autoimmune diseases of the digestive tract (e.g., celiac disease, Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectial disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc.

In still another embodiment, the method of the present invention, e.g., modulating a chemosensory receptor and/or its ligand includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impairments associated with protein-energy malnutrition, etc.), obesity, secondary obesity (e.g., hypothyroidism, Cushing's disease, insullinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycermia, hyperlipoproteinemias, etc.

In still yet another embodiment, the method of the present invention, e.g., modulating a chemosensory receptor and/or its ligand includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastricintestinal tract, cold sensation of extremities, difficulty in concentration, impatience, sleep disorder, headache, general malaise, palpitation, night sweat, anxiety, dizziness, vertigo, hot flash, excess sweating, depression, etc.

In still yet another embodiment, the method of the present invention, e.g., modulating a chemosensory receptor and/or its ligand includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. In general, such promotion can be achieved either directly or via increasing the secretion of a regulatory entity, e.g., hormones, etc.

In still yet another embodiment, the method of the present invention, e.g., modulating a chemosensory receptor and/or its ligand includes increasing one or more gastrointestinal functions of a subject, e.g., to improve the quality of life or healthy state of a subject.

In one embodiment, the present invention provides a pharmaceutical composition containing a therapeutically effective amount of one or more compounds of the present invention, or a salt, solvate, and/or prodrug thereof, optionally with a suitable amount of a pharmaceutically acceptable vehicle. In another embodiment, the pharmaceutical composition comprises a therapeutically effective amount of one or more compounds of the present invention, or a salt, solvate, and/or prodrug thereof; and a suitable amount of a pharmaceutically acceptable vehicle so as to provide the form for proper administration to a patient.

In one embodiment, when administered to a patient, the compounds of the present invention and the optional pharmaceutically acceptable vehicles are sterile. In one embodiment, water is a preferred vehicle when a compound of the present invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the present invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration a compound of the present invention may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, the compounds of the present invention are formulated in accordance with routine procedures as a pharmaceutical composition adapted for intravenous administration to human beings. Typically, compounds of the present invention for intravenous administration are solutions in sterile isotonic aqueous buffer. For injection, a compound of the present invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the present invention is administered by infusion, it can be dispensed, for example, with an infusion bottle containing sterile pharmaceutical grade water or saline. When the compound of the present invention is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of the present invention may also be formulated in rectal or vaginal pharmaceutical compositions such as suppositories or retention enemas, e.g., containing conventional suppository bases such as cocoa butter or other glycerides.

In addition to the formulations described previously, a compound of the present invention may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

A compound of the present invention, and/or pharmaceutical composition thereof, will generally be used in an amount effective to achieve the intended purpose. For use to treat or prevent diseases or disorders the compounds of the present invention and/or pharmaceutical compositions thereof, are administered or applied in a therapeutically effective amount.

The amount of a compound of the present invention that will be effective in the treatment of a particular disorder or condition disclosed herein will depend on the nature of the disorder or condition and can be determined by standard clinical techniques known in the art. In addition, in vitro or in vivo assays may optionally be employed to help identify optimal dosage ranges. The amount of a compound of the present invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the compounds of the present invention are delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound of the present invention per kilogram body weight. Dosage ranges may be readily determined by methods known to the artisan of ordinary skill the art.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

In one embodiment, a therapeutically effective dose of a compound of the present invention described herein will provide therapeutic benefit without causing substantial toxicity. Toxicity of compounds of the present invention may be determined using standard pharmaceutical procedures and may be readily ascertained by the skilled artisan. The dose ratio between toxic and therapeutic effect is the therapeutic index. A compound of the present invention will preferably exhibit particularly high therapeutic indices in treating disease and disorders. The dosage of a compound of the present invention described herein will preferably be within a range of circulating concentrations that include an effective dose with little or no toxicity.

In certain embodiments of the present invention, the compounds of the present invention and/or pharmaceutical compositions thereof can be used in combination therapy with at least one other agent. The compound of the present invention and/or pharmaceutical composition thereof and the other agent can act additively or, more preferably, synergistically. In some embodiments, a compound of the present invention and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haen, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions oïMethoden der Organischen Chemie (Houben-Weyl), and the like. Many general methods for preparation of starting materials comprising variously substituted heterocyclic, hetereoaryl, and aryl rings (the precursors of Ar, $hAr^1$, and/or $hAr^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entireties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, 3ʳ Ed., John Wiley & Sons (1999).

Some exemplary synthetic methods for preparing the present compounds are illustrated in the Schemes 1 to 3 below.

Scheme 1: Preparation of substituted 4-aminoquinoline-3-carboxylate derivatives (VI) from substituted anilines (I)

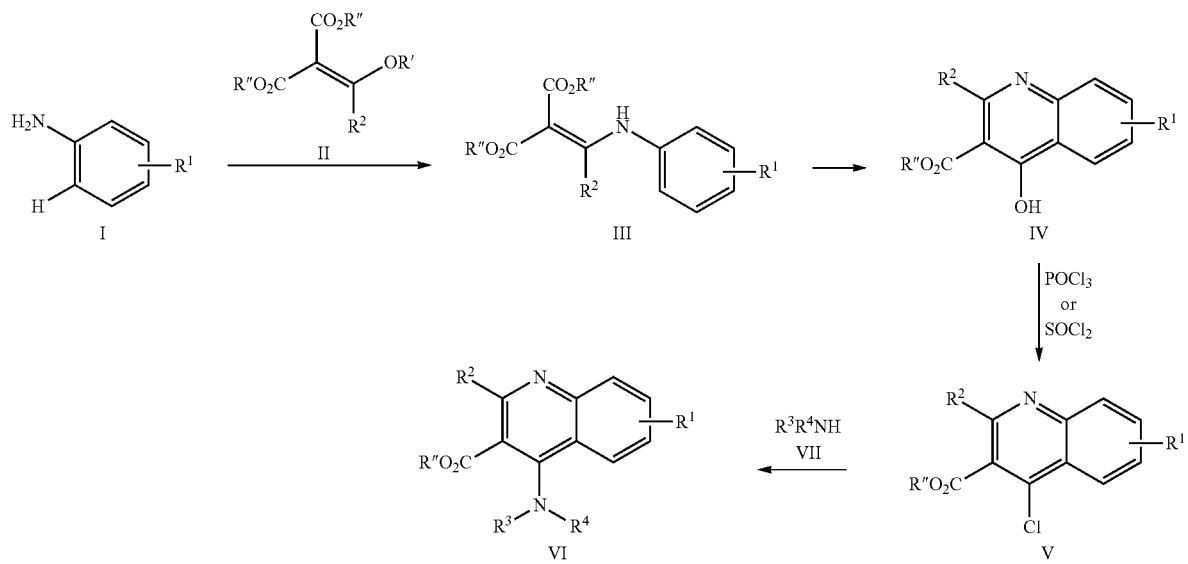

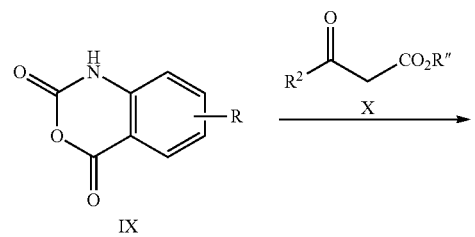

As shown in Scheme 1, substituted 4-aminoquinoline-3-carboxylate derivatives (VI) can be prepared by reacting the corresponding anilines I with 2-(alkoxymethylene)malonates II followed by cyclization of the intermediates III under elevated temperature to provide the hydroxyl intermediates IV that can be treated with POCl₃ or SO₂Cl₂ to provide the corresponding chloride derivatives V that can be further treated with ammonia or amines to give the desired amino-ququinolines VI. (Kamal, A. et al. *Bioorg. Med. Chem.* 2005, 13, 2021-2029; Fryer, R. I. et al. *J. Med. Chem.* 1993, 36, 1669-1673; Bi, Y. et al. *Bioorg. Med. Chem. Lett.* 2004, 14, 1577-1580; Li, S. Y. et al. *Bioorg. Med. Chem.* 2006, 14, 7370-7376. Koga, H. et al. *J. Med. Chem.* 1980, 23, 1358-1363).

Scheme 2: Preparation of substituted 4-aminoquinoline-3-carboxylate derivatives (VI) from substituted 2-aminobenzoic acid derivatives (VIII)

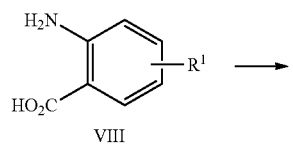

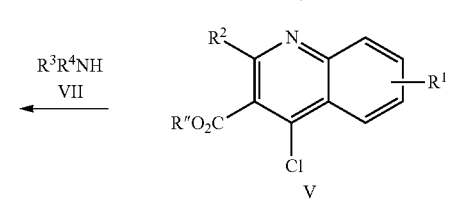

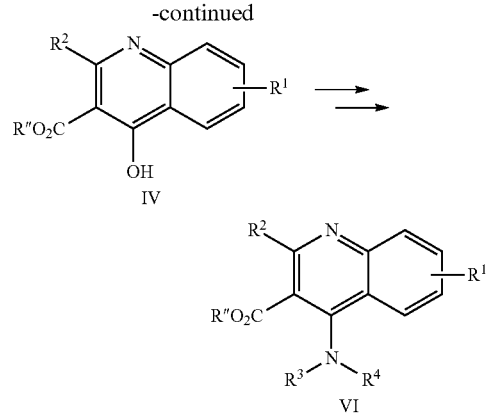

Substituted 4-aminoquinoline-3-carboxylate derivatives (VI) can also be prepared by reacting the corresponding 2-aminobenzoic acids VIII with phosgene or equivalent to provide the isatoic anhydrides IX that can be further reacted with X to give the derivatives IV (Mai, A. et al. *J. Med. Chem.* 2006, 49, 6897-6907. Beutner, G. L. et al. *J. Org. Chem.* 2007, 72, 7058-7061, and references cited therein), which can be converted to VI as described in Scheme 1.

Scheme 3: Preparation of substituted 4-aminoquinoline-3-carboxylate derivatives (VI) from substituted 2-amino benzonitrile derivatives (XI)

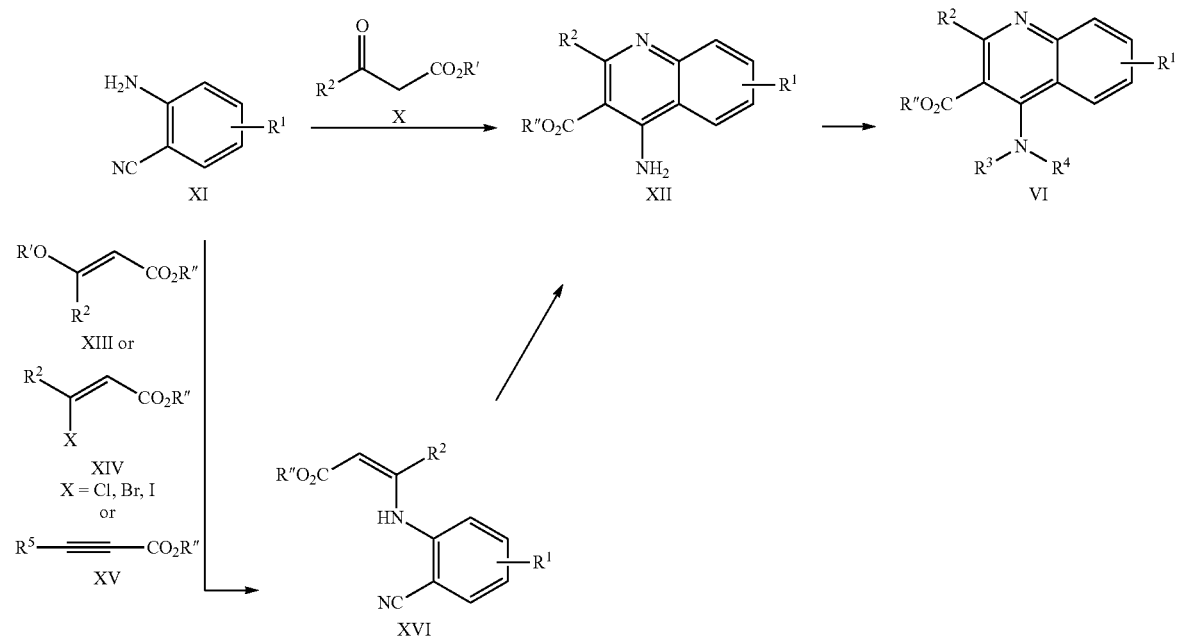

Alternatively, substituted 4-aminoquinoline-3-carboxylate derivatives (VI) can be prepared by reacting the corresponding amino benzonitriles XI with X to provide the amino derivatives XII (Sestili, I. et al. *Eur. J. Med. Chem.* 2004, 39, 1047-1057. Doucet-Personeni, C. et al. *J. Med. Chem.* 2001, 44, 3203-3215. Veronese, A. C. et al. *Tetrahedron* 1995, 51, 12277-12284, and the references cited therein.) that can be further alkylated to give the substituted aminoquinolines VI as shown in Scheme 3. Amino quinolines XII can also be prepared via a Michael addition of the 2-amino benzonitriles XI to various α,β-unsaturated carboxylate derivatives XIII, XIV or XV to provide the adducts XVI (MacNab, H. et al. *Synthesis* 2009, 2171-2174. Vicario, J. L. *Synthesis* 2007, 2065-2092, and references cited therein.) that can be further cyclized to give the amino quinolines XII (Han, G. F. et al. *Synth. Commun.* 2009, 39, 2492-2505. Tabarrini, O. et al. *Bioorg. Med. Chem.* 2001, 9, 2921-2928. Shutske, G. M. et al. *J. Med. Chem.* 1989, 32, 1805-1813, and references cited therein).

EXAMPLES

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

Example A 4-amino-6-methoxyquinoline-3-carboxylic acid

To a stirred solution of ethyl 4-amino-6-methoxyquinoline-3-carboxylate (Example Aa, 1.23 g, 5.0 mmol) in EtOH (20.0 mL) was added aqueous NaOH (2.0 N, 5.0 mL) at room temperature. The reaction mixture was then refluxed for 3 hr. The solution was then filtered and washed with water. The filtrate was cooled to 0° C. and neutralized carefully with 1 N HCl to pH 7. Most of the EtOH was removed under reduced pressure, and the precipitate was collected by filtration, washed with cold water, and dried under vacuum to give the title compound as an off-white solid (1.01 g, 93%). $^1$H NMR (400 MHz, DMSO-$d_6$) δ 3.89 (s, 3H), 7.40 (dd, J=2.8, 9.4 Hz, 1H), 7.73 (d, J=9.4 Hz, 1H), 7.77 (d, J=2.8 Hz, 1H), 8.77 (s, 1H). MS 219 (MH$^+$).

Example Aa ethyl 4-amino-6-methoxyquinoline-3-carboxylate

A mixture of ethyl 4-chloro-6-methoxyquinoline-3-carboxylate (Example Ab, 796 mg, 3.0 mmol) and ammonia (25% aqueous solution, 10 mL) in isopropanol (40 mL) was stirred at 110° C. in a pressure reactor overnight. Most of the solvent was then removed under reduced pressure, and the reaction mixture was diluted with water. The precipitate was collected by filtration, washed with cold water, and dried under vacuum to give the title compound as an off-white solid (680 mg, 92%). $^1$H NMR (400 MHz, DMSO-d$_6$) δ 1.33 (t, J=7.0 Hz, 3H), 3.88 (s, 3H), 4.32 (q, J=7.0 Hz, 2H), 7.36 (dd, J=2.8, 8.8 Hz, 1H), 7.72 (d, J=8.8 Hz, 1H), 7.74 (d, J=2.8 Hz, 1H), 8.23 (bs, 2H), 8.77 (s, 1H). MS 247 (MH$^+$).

Example Ab ethyl 4-chloro-6-methoxyquinoline-3-carboxylate

A solution of ethyl 4-hydroxy-6-methoxyquinoline-3-carboxylate (Example Ac, 1.24 g, 5.0 mmol) in POCl$_3$ was refluxed under nitrogen for 3 hrs. The solution was cooled to room temperature and evaporated under reduced pressure. The residue was carefully quenched with ice, and neutralized with 2.0 N NaOH to pH 7. The precipitate was collected by filtration, washed with cold water, and dried under vacuum to give the title compound as a pale-yellow solid (1.29 g, 97%). $^1$H NMR (400 MHz, DMSO-d$_6$) δ 1.36 (t, J=7.0 Hz, 3H), 3.96 (s, 3H), 4.41 (q, J=7.0 Hz, 2H), 7.57 (d, J=2.8 Hz, 1H), 7.61 (dd, J=2.8, 8.8 Hz, 1H), 8.05 (d, J=8.8 Hz, 1H), 8.97 (s, 1H). MS 266, 268 (MH$^+$).

Example Ac ethyl 4-hydroxy-6-methoxyquinoline-3-carboxylate

A mixture of 4-methoxyaniline (12.3 g, 100 mmol) and diethyl 2-(ethoxymethylene)malonate (21.6 g, 100 mmol) was stirred at 120° C. under nitrogen for 4 hrs. The solution was cooled to room temperature and Ph$_2$O (100 mL) was added. The reaction mixture was refluxed at 260° C. under nitrogen for 8 hrs. The solution was cooled to room temperature and diluted with hexanes. The resultant precipitate was collected by filtration, washed with 25% ethyl acetate in hexanes, and dried under vacuum to give ethyl 4-hydroxy-6-methoxyquinoline-3-carboxylate as a pale-yellow solid (4.21 g, 17%). $^1$H NMR (400 MHz, DMSO-d$_6$) δ 1.26 (t, J=7.0 Hz, 3H), 3.83 (s, 3H), 4.19 (q, J=7.0 Hz, 2H), 7.32 (dd, J=3.2, 9.6 Hz, 1H), 7.55 (d, J=3.2 Hz, 1H), 7.56 (d, J=9.6 Hz, 1H), 8.47 (s, 1H), 12.27 (s, 1H). MS 248 (MH$^+$).

Example B 4-amino-5-(2,2-dimethyl-3-oxo-3-(propylamino) propoxy)-2-methyl-quinoline-3-carboxylic acid

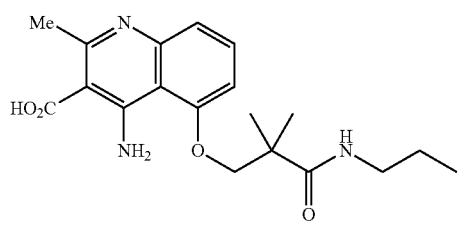 [SMILES: CCCNC(=O)C(C)(C)COc1cccc2nc(C)c(C(=O)O)c(N)c12]

Prepared as in Example A from ethyl 4-amino-5-(2,2-dimethyl-3-oxo-3-(propylamino)-propoxy)-2-methylquinoline-3-carboxylate (Example Ba) as an off-white solid (41%). $^1$H NMR (400 MHz, DMSO-d$_6$) δ 0.73 (t, J=7.6 Hz, 3H), 1.25 (s, 6H), 1.33-1.42 (m, 2H), 2.76 (s, 3H), 3.00-3.05 (m, 2H), 4.16 (s, 2H), 7.01 (d, J=8.0 Hz, 1H), 7.29 (d, J=8.0 Hz, 1H), 7.67 (t, J=8.0 Hz, 1H), 7.89 (t, J=5.8 Hz, 1H), 8.85 (bs, 1H), 12.28 (bs, 1H), 12.78 (bs, 1H). MS 360 (MH$^+$).

Example Ba ethyl 4-amino-5-(2,2-dimethyl-3-oxo-3-(propylamino)propoxy)-2-methylquinoline-3-carboxylate To a solution of 3-(3-amino-2-cyanophenoxy)-2,2-dimethyl-N-propylpropan-amide (Tachdjian, C. et al. *PCT Int. Appl.* 2008, WO 2008154221, 1.38 g, 5.0 mmol) and ethyl acetoacetate (0.66 g, 5.0 mmol) in dry toluene (150 mL) was added SnCl$_4$ (2.61 g, 10.0 mmol) dropwise via syringe at room temperature under nitrogen. After 1 hr at room temperature, the reaction mixture was refluxed for an additional 5 hrs. The solution was cooled to room temperature and the solvent removed under reduced pressure. The residue was diluted with EtOAc, and aqueous NaOH (2N) was added at room temperature to pH>8. The solution was filtered and the organic layer separated. The aqueous layer was extracted with EtOAc (5×). The combined organic layers was washed with brine, and dried over Na$_2$SO$_4$. After evaporation of the solvent, the residue was purified by chromatography on silica gel (0.5% MeOH in EtOAc) to give the title compound as an off-white solid (1.63 g, 84%). $^1$H NMR (400 MHz, DMSO-d$_6$) δ 0.73 (t, J=7.6 Hz, 3H), 1.25 (s, 6H), 1.32 (t, J=7.4 Hz, 3H), 1.35-1.42 (m, 2H), 2.54 (s, 3H), 3.00-3.05 (m, 2H), 4.12 (s, 2H), 4.31 (q, J=7.4 Hz, 2H), 6.87 (d, J=8.0 Hz, 1H), 7.23 (d, J=8.0 Hz, 1H), 7.50 (t, J=8.0 Hz, 1H), 7.80 (t, J=5.6 Hz, 1H), 8.08 (s, 2H). MS 388 (MH$^+$).

Example C 4-amino-5-(2-ethylbutoxy)-2-methylquinoline-3-carboxylic acid

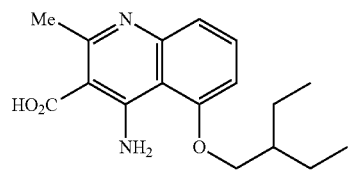 [SMILES: CCC(CC)COc1cccc2nc(C)c(C(=O)O)c(N)c12]

Prepared as in Example A from ethyl 4-amino-5-(2-ethylbutoxy)-2-methylquinoline-3-carboxylate (Example Ca) as a white solid (45%). M.p.: 145-151° C. $^1$H NMR (400 MHz, DMSO-d$_6$) δ 0.90 (t, J=8 Hz, 6H), 1.48-1.41, (m, 4H), 1.84-1.78 (m, 1H), 2.73 (s, 3H), 4.11 (d, J=8 Hz, 2H), 6.99 (d, J=8 Hz, 1H), 7.32 (d, J=8 Hz, 1H), 7.59 (t, J=8 Hz, 1H), 8.40 (brs, 1H), 11.09 (brs, 1H), 13.91 (brs, 1H). MS 303 (MH$^+$).

Example Ca ethyl 4-amino-5-(2-ethylbutoxy)-2-methylquinoline-3-carboxylate

Prepared as in Example Ba from 2-amino-6-(2-ethylbutoxyl)benzonitrile (Example Cb) and ethyl 3-oxobutanoate as a white solid (89%). $^1$H NMR (400 MHz, DMSO-d$_6$) δ 0.90 (t, J=8 Hz, 6H), 1.32 (t, J=8 Hz, 3H), 1.48-1.41 (m, 4H), 1.79-1.73 (m, 1H), 2.54 (s, 3H), 4.08 (d, J=4 Hz, 2H), 4.31

(q, J=8 Hz, 2H), 6.92 (dd, J=2, 8 Hz, 1H), 7.23 (dd, J=2, 8 Hz, 1H), 7.50 (t, J=8 Hz, 1H), 8.04 (brs, 1H). MS 331 (MH+).

Example Cb 2-amino-6-(2-ethylbutoxyl)benzonitrile

To a solution of 2-ethylbutan-1-ol (1.02 g, 10.0 mmol) in dry THF (60 mL) was carefully added NaH (60% in mineral oil, 480 mg, 12.0 mmol) in small portions at 0° C. under nitrogen. The reaction mixture was stirred at 0 OC under nitrogen for 2 hrs. To this solution was added 2-amino-6-fluorobenzonitrile (1.36 g, 10.0 mmol), and the reaction solution was stirred at 0° C.-RT for 2 hrs, and then at 65 OC overnight under nitrogen. The reaction was cooled down to room temperature then quenched with brine, and extracted with EtOAc (3×). The combined organic layers were washed with brine, dried over Na$_2$SO$_4$. Filtered and evaporated under reduced pressure. The residue was purified by chromatography on silica gel (eluent: 20% EtOAc in hexanes) to give the title compound as colorless oil (1.29 g, 59%). $^1$H NMR (400 MHz, CDCl$_3$) δ 0.93 (t, J=8 Hz, 6H), 1.55-1.43 (m, 4H), 1.73-1.65 (m, 1H), 3.90 (d, J=4 Hz, 2H), 4.10 (brs, 2H), 6.25 (d, J=8 Hz, 1H), 6.34 (d, J=8 Hz, 1H), 7.20 (t, J=8 Hz, 1H).

Example D 4-amino-5-(2-(isonicotinamido)-2-methylpropoxy)-2-methylquinoline-3-carboxylic acid

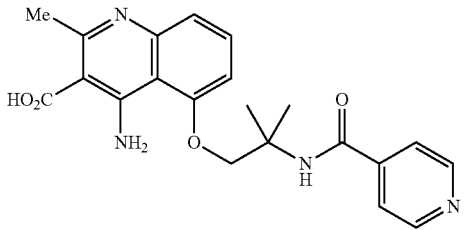 [SMILES: Cc1nc2cccc(OCC(C)(C)NC(=O)c3ccncc3)c2c(N)c1C(=O)O]

Prepared as in Example A from ethyl 4-amino-5-(2-(isonicotinamido)-2-methylpropoxy)-2-methylquinoline-3-carboxylate (Example Da) as a white solid (67%). M.p.: 195-198° C. $^1$H NMR (400 MHz, DMSO-d$_6$) δ 1.51 (s, 6H), 2.75 (s, 3H), 4.48 (s, 2H), 7.07 (d, J=8 Hz, 1H), 7.31 (d, J=8 Hz, 1H), 7.67 (t, J=8 Hz, 1H), 7.70 (dd, J=1, 8 Hz, 2H), 8.50 (s, 1H), 8.67 (dd, J=1, 8 Hz, 2H), 8.76 (brs, 1H), 12.19 (brs, 1H), 12.85 (brs, 1H). MS 395 (MH+).

Example Da ethyl 4-amino-5-(2-(isonicotinamido)-2-methylpropoxy)-2-methylquino-line-3-carboxylate To a solution of ethyl 4-amino-5-(2-amino-2-methylpropoxy)-2-methylquinoline-3-carboxylate (Example Db, 1.0 g, 3.15 mmol) in dry DMF (20 mL) was added isonicotinic acid (504 mg, 4.10 mmol), followed by EDCI (783 mg, 4.10 mmol), HOBt (554 mg, 4.10 mmol), and triethylamine (414 mg, 4.10 mmol) at room temperature under nitrogen. After it was stirred at room temperature for 12 hrs, the reaction mixture was concentrated under reduced pressure. The residue was diluted with water, and extracted with EtOAc (3×). The aqueous layer was basified with 2N NaOH to pH 8 and extracted with EtOAc (3×). The combined organic layers were washed with brine, dried over MgSO$_4$, filtered, concentrated, and purified by chromatography on silica gel eluting with 10% MeOH in dichloromethane to give the title compound as a yellow solid (1.1 g, 83%). $^1$H NMR (400 MHz, DMSO-d$_6$) δ 1.29 (t, J=4 Hz, 3H), 1.51 (s, 6H), 2.94 (s, 3H), 4.28 (q, J=4 Hz, 2H), 4.42 (s, 2H), 6.93 (dd, J=1, 8 Hz, 1H), 7.24 (dd, J=1, 8 Hz, 2H), 7.52 (t, J=8 Hz, 1H), 7.69 (dd, J=2, 4 Hz, 2H), 8.14 (s, 2H), 8.37 (s, 1H), 8.67 (dd, J=2, 4 Hz, 2H). MS 423 (MH+).

Example Db ethyl 4-amino-5-(2-amino-2-methylpropoxy)-2-methylquinoline-3-carboxylate Prepared as in Example Ba from benzyl 1-(3-amino-2-cyanophenoxy)-2-methylpropan-2-ylcarbamate (Example Dc) and ethyl 3-oxobutanoate as a yellow-brown solid (91%). $^1$H NMR (400 MHz, DMSO-d$_6$) δ 1.15 (s, 6H), 1.31 (t, J=4 Hz, 3H), 2.54 (s, 3H), 3.87 (s, 2H), 4.31 (q, J=4 Hz, 2H), 6.85 (d, J=4 Hz, 1H), 7.21 (d, J=4 Hz, 1H), 7.49 (t, J=8 Hz, 1H), 8.38 (brs, 2H). MS 318 (MH+).

Example Dc benzyl 1-(3-amino-2-cyanophenoxy)-2-methylpropan-2-ylcarbamate

To a solution of 2-amino-6-(2-amino-2-methylpropoxy)benzonitrile (Example Dd, 30.5 g, 148.6 mmol) in THF/H$_2$O (1:1, 400 mL) was added NaHCO$_3$ (24.7 g, 294 mmol), followed by benzyl (2,5-dioxopyrrolidin-1-yl) carbonate (44.0 g, 176 mmol) at room temperature. The reaction was stirred at room temperature for 4 h then the organic layer was separated and the aqueous layer was extracted with EtOAc (2×). The combined organic layers were washed with brine and dried over MgSO$_4$. After filtration, the solvent was evaporated and the crude oil was purified by chromatography on silica gel (eluent: 0-60% EtOAc in hexane) to give the title compound as yellow oil (44.8 g, 89%). $^1$H NMR (400 MHz, DMSO-d$_6$) δ 1.30 (s, 6H), 4.02 (s, 2H), 4.96 (s, 2H), 5.98 (s, 2H), 6.14 (d, J=8.0 Hz, 1H), 6.32 (dd, J=0.8, 8.4 Hz, 1H), 7.12 (t, J=8.4 Hz, 1H), 7.38-7.21 (m, 6H). MS 340 (MH+).

Example Dd 2-amino-6-(2-amino-2-methylpropoxy)benzonitrile

To a solution of 2-amino-2-methylpropan-1-ol (14.4 g, 161 mmol) in anhydrous THF (150 mL) was added NaH (6.8 g, 161 mmol, 60% in mineral oil) in small portions at 0 OC under nitrogen. The mixture was stirred at 0 OC for 30 minutes and then stirred at room temperature for another 30 minutes. The solution was cooled down to 0 OC again, and to this solution was added dropwise a solution of 2-amino-6-fluorobenzonitrile (20.0 g, 147 mmol) in anhydrous THF (50 mL). The reaction mixture was then refluxed overnight under nitrogen. The reaction mixture was cooled down to room temperature and carefully quenched with aqueous NH$_4$Cl solution and extracted with ethyl acetate (3×). The combined organic layers were washed with brine, dried over MgSO$_4$, filtered and concentrated. The crude mixture was purified by chromatography on silica gel eluting with 10% MeOH in DCM to give the title compound as yellow solid (23.4 g 71%). ¹H NMR (400 MHz, DMSO-d₆) δ 1.08 (s, 6H), 3.15 (s, 2H), 3.64 (s, 2H), 5.98 (s, 2H), 6.13 (d, J=8.0 Hz, 1H), 6.31 (d, J=8.4 Hz, 1H), 7.15 (t, J=8.4 Hz, 1H). MS 236 (MH⁺).

Example E 4-amino-5-(3-(cyclohexylamino)-2,2-dimethyl-3-oxopropoxy)-2-methyl-quinoline-3-carboxylic acid

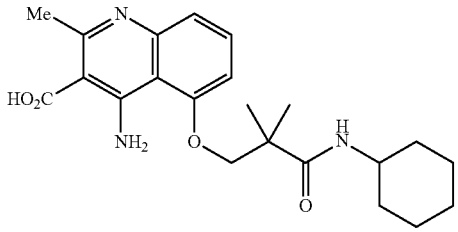 [SMILES: Cc1nc2cccc(OCC(C)(C)C(=O)NC3CCCCC3)c2c(N)c1C(=O)O]

Prepared as in Example A from ethyl 4-amino-5-(3-(cyclohexylamino)-2,2-dimethyl-3-oxopropoxy)-2-methylquinoline-3-carboxylate (Example Ea) as an off-white solid (13%). MS 400 (MH⁺).

Example Ea ethyl 4-amino-5-(3-(cyclohexylamino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example Eb) and cyclohexanamine as a yellow-brown solid (46%). MS 428 (MH⁺).

Example Eb 3-((4-amino-3-(ethoxycarbonyl)-2-methylquinolin-5-yl)oxy)-2,2-dimethyl-propanoic acid Prepared as in Example Ba from benzyl 3-(3-amino-2-cyanophenoxy)-2,2-dimethyl-propanoate (Example Ec) and ethyl 3-oxobutanoate as a brown solid (80%). MS 192 (MH⁺).

Example Ec 3-(3-amino-2-cyanophenoxy)-2,2-dimethyl-propanoate

To a solution of benzyl 3-(2-cyano-3-nitrophenoxy)-2,2-dimethylpropanoate (Example Ed, 200 mg, 0.56 mmol) in AcOH (5 mL) was added iron powder (158 mg, 2.82 mmol) at room temperature. The reaction mixture was then stirred at 90° C. for 1 h. The reaction mixture was was cooled to room temperature then diluted with AcOEt. The precipitate was filtered off and the filtrate was successively washed with 1 N NaOH and brine, then dried over Na₂SO₄, filtered and evaporated. The residue was purified by chromatography on silica gel (eluent: 40% EtOAc in hexanes) to give a title compound as a colorless oil (187 mg, 100%). MS 325 (MH⁺).

Example Ed benzyl 3-(2-cyano-3-nitrophenoxy)-2,2-dimethylpropanoate

To a solution of benzyl 3-hydroxy-2,2-dimethylpropanoate (Yang, D. et al. *J. Am. Chem. Soc.* 2002, 124, 9966. 6.68 g, 32.1 mmol) in dry THF (200 mL) was carefully added NaH (60% in mineral oil, 3.5 g, 87.5 mmol) in small portions at 0 OC under nitrogen. The reaction mixture was stirred at 0° C. under nitrogen for 2 hrs. To this solution was added 2,6-dinitrobenzonitrile (6.19 g, 32.1 mmol), and the reaction solution was stirred at 0° C.-RT under nitrogen overnight. The reaction mixture was quenched with brine, and extracted with EtOAc (3×). The combined organic layers were washed with brine, dried over Na₂SO₄. After evaporation of the solvent, the residue was purified by chromatography on silica gel eluting (Elunet: 20% EtOAc in hexanes) to give the title compound as a brown solid (10.0 g, 87%). MS 355 (MH⁺).

Example F 4-amino-5-(cyclohexyloxy)-2-methylquinoline-3-carboxylic acid hydrochloride

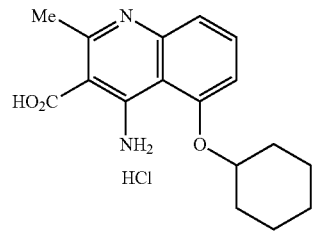 [SMILES: Cc1nc2cccc(OC3CCCCC3)c2c(N)c1C(=O)O ; Cl]

To a suspension of 4-amino-5-(cyclohexyloxy)-2-methylquinoline-3-carboxylic acid (Example H, 1.0 g, 3.33 mmol) in ethanol (10 mL) was added 1.25 M solution of HCl in ethanol (2.93 mL, 3.66 mmol). The clear solution was stirred for 30 minutes and evaporated to dryness to provide 4-amino-5-(cyclohexyloxy)-2-methylquinoline-3-carboxylic acid hydrochloride (1.12 g, 100%) as a white solid. ¹H NMR (400 MHz, DMSO-d₆) δ 1.30 (m, 1H), 1.39-1.47 (m, 2H), 1.53-1.72 (m, 5H), 2.01-2.05 (m, 2H), 2.82 (s, 3H), 4.78-4.82 (m, 1H), 7.29-7.31 (d, J=8.0 Hz, 1H), 7.61-7.63 (d, J=8.0 Hz, 1H), 7.82 (t, J=8.4 Hz, 1H), 9.30 (bs, 1H), 9.93 (bs, 1H). MS 301 (MH⁺-HCl).

Example G sodium 4-amino-5-(cyclohexyloxy)-2-methylquinoline-3-carboxylate

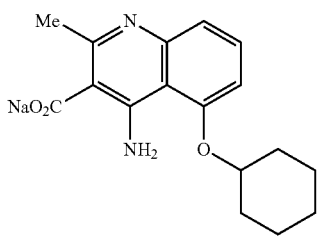

To a solution of 4-amino-5-(cyclohexyloxy)-2-methylquinoline-3-carboxylic acid (Example II, 1.0 g, 3.33 mmol) in ethanol (20 mL) was added a solution of NaHCO$_3$ (294 mg, 3.50 mmol) in water (15 mL). The mixture was stirred and warmed up to 60° C. until the solution become clear then evaporated to dryness to provide sodium 4-amino-5-(cyclohexyloxy)-2-methylquinoline-3-carboxylate (1.07 g, 100%) as a white solid. $^1$H NMR (400 MHz, DMSO-d$_6$) δ 1.25-1.45 (m, 3H), 1.50-1.70 (m, 5H), 1.53-1.72 (m, 5H), 1.98-2.00 (m, 2H), 2.64 (s, 3H), 4.59-4.63 (m, 1H), 6.87-6.89 (d, J=7.6 Hz, 1H), 7.20-7.22 (d, J=8.0 Hz, 1H), 7.42 (t, J=8.0 Hz, 1H). MS 301 (MH$^+$+H-Na).

Example II 4-amino-5-(cyclohexyloxy)-2-methylquinoline-3-carboxylic acid

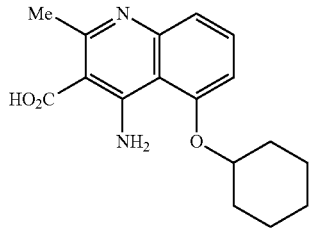 [SMILES: Cc1nc2cccc(OC3CCCCC3)c2c(N)c1C(=O)O]

To a solution of ethyl 4-amino-5-(cyclohexyloxy)-2-methylquinoline-3-carboxylate (Example IIa, 110 g, 0.335 mol) in EtOH (450 mL) was added a solution of NaOH (33.5 g, 0.837 mol) in water (200 mL) at room temperature. The reaction mixture was then refluxed overnight. The reaction solution was cooled down to 0° C. and carefully neutralized with 4N HCl to pH 7. The resultant solution was concentrated under reduced pressure to remove most of the EtOH. The precipitate was collected by filtration, and re-dissolved in EtOH (4 L) at 65° C. and treated with activated charcoal (5 g) for 0.5 h. The charcoal was removed by filtration over celite, and the filtrate was concentrated. The precipitate was collected by filtration, washed with cold water, and dried under vacuum at 60° C. overnight to give the title compound as a white solid (100 g, 99%). M.p.: 220.0-221.5° C. $^1$H NMR (400 MHz, DMSO-d$_6$) δ 1.28-1.72 (m, 8H), 2.00-2.04 (m, 2H), 2.75 (s, 3H), 4.69-4.71 (m, 1H), 7.10-7.12 (d, J=8.0 Hz, 1H), 7.24-7.26 (d, J=8.0 Hz, 1H), 7.65 (t, J=8.0 Hz, 1H), 12.80 (brs, 1H). MS 301 (MH$^+$). Elemental Analysis Calculated (Found) for C$_{17}$H$_{20}$N$_2$O$_3$: C, 67.98% (67.74%); H, 6.71% (7.01%); N, 9.33% (9.40%).

Example IIa ethyl 4-amino-5-(cyclohexyloxy)-2-methylquinoline-3-carboxylate

A solution of ethyl 3-oxobutanoate (29.9 g, 0.230 mol) in anhydrous toluene (200 mL) was added to a solution of 2-amino-6-(cyclohexyloxy)benzonitrile (Example IIb, 49.8 g, 0.230 mol) in anhydrous toluene (1000 mL) under nitrogen in a 3 L round bottom flask sitting in an oil bath at room temperature. SnCl$_4$ (53.9 mL, 0.461 mol) was added slowly over a period of approximately 1 h. The oil bath temperature was then raised to 110° C. and the reaction mixture was stirred at that temperature for 2.5 h. It was then cooled down to 5° C., still under nitrogen, and the toluene was decanted away from the immiscible viscous oil at the bottom of the flask. The viscous oil was further concentrated under vacuum at 60° C., re-dissolved in boiling ethyl acetate (1 L), and transferred to a 4 liter Erlenmeyer flask. The solution was diluted with more EtOAc (1.5 L), cooled down to –15° C., and neutralized with NaOH (3 N, 500 mL). The organic layer was separated, and the aqueous emulsion was extracted once more with ethyl acetate. The insoluble tin salts were filtered out from the aqueous layer, then both the salts and aqueous filtrate were washed once more with ethyl acetate. The combined organic layers were dried over MgSO$_4$, concentrated, and passed through a silica column using 0% to 60% ethyl acetate in hexanes. The product was purified by recrystallization from EtOAc to give the title compound as an off-white solid (64.3 g, 85%). $^1$H NMR (400 MHz, DMSO-d$_6$) δ 1.28-1.34 (m, 1H), 1.32 (t, 3H), 1.37-1.45 (m, 2H), 1.51-1.63 (m, 3H), 1.67-1.71 (m, 2H), 1.99-2.03 (m, 2H), 2.54 (s, 3H), 4.28-4.33 (q, J=6.8 Hz, 2H), 4.64 (m, 1H), 6.95-6.97 (d, J=7.6 Hz, 1H), 7.19-7.21 (d, J=8.4 Hz, 1H), 7.65 (t, J=8.4 Hz, 1H), 8.15 (brs, 2H). MS 329 (MH$^+$).

Example IIb 2-amino-6-(cyclohexyloxy)benzonitrile

To a solution of cyclohexanol (19.1 g, 0.191 mol) in anhydrous THF (500 mL) was added NaH (7.6 g, 40% in mineral oil, 0.191 mol) in small portions at 0 OC under nitrogen. The mixture was stirred at room temperature for 1 h and a solution of 2-amino-6-fluorobenzonitrile (20.0 g, 0.15 mol) in anhydrous THF (150 mL) was added drop-wise at room temperature. The reaction mixture was heated to reflux overnight then cooled to room temperature and most of the THF removed under reduced pressure. Ice water (100 mL) was added to the concentrated reaction mixture followed by EtOAc (500 mL). The organic layer was separated and successively washed with water and brine, dried over Na$_2$SO$_4$, filtered and evaporated under reduced pressure. The residue was purified by chromatography on silica gel eluting with 25-30% EtOAc in hexanes to give 2-amino-6-(cyclohexyloxy)benzonitrile as a light yellow oil (17.9 g, 56%). $^1$H NMR (400 MHz, CDCl$_3$) δ 1.32-1.43 (m, 3H), 1.51-1.55 (m, 1H), 1.62-1.69 (m, 2H), 1.79-1.95 (m, 4H), 4.31-4.36 (m, 3H), 6.23-6.27 (m, 2H), 7.18 (d, J=8.0 Hz, 1H). MS 329 (MH$^+$).

Example IIb 2-amino-6-(cyclohexyloxy)benzonitrile

Alternative Methode a):

To a solution of 2-(cyclohexyloxy)-6-nitrobenzonitrile (Example IIc, 50.0 g, 0.20 mol) in THF/AcOH (1:1 by volume, 500 mL) was added iron powder (34.0 g, 0.61 mol) in one portion at room temperature under nitrogen. The reaction mixture was refluxed for 40 min under nitrogen and cooled down to room temperature and EtOAc (2 L) was added. The precipitate that formed was filtered off and washed with EtOAc. The organic layer was separated and washed successively with water (2×300 mL), aqueous NaOH (1.0 N, 2×300 mL), saturated Na$_2$CO$_3$ solution (300 mL), brine (300 mL), dried over Na$_2$SO$_4$ filtered and evaporated under reduced pressure. The residue was purified by chromatography on silica gel eluting with 25% EtOAc in hexanes to give 2-amino-6-(cyclohexyloxy)benzonitrile as a pale yellow oil (45.0 g, 94%), which solidified after storage overnight at room temperature.

Alternative Methode b):

A 3-L 3-neck round bottom flask was first purged with nitrogen. 10% Pd/C (2.81 g) was then added under nitrogen, followed successively by 2-(cyclohexyloxy)-6-nitrobenzonitrile (Example IIe, 43.2 g, 0.175 mol), anhydrous methanol (389 mL), and acetic acid (80.4 mL). A reflux condenser, a dropping funnel containing a solution of ammonium formate (49.8 g, 0.790 mol) in anhydrous methanol (498 mL), thermometer, nitrogen inlet and nitrogen outlet were attached. Ammonium formate solution (75 mL) was added at room temperature, then the reaction was slowly heated to a maximum of 42° C. The mixture was monitored carefully until initiation of the reaction was observed (an evolution of gas occurred with roughly a 10° C. exotherm). Initiation of the reaction often took up to 40 minutes before starting. The remaining of the ammonium formate solution was then added at a rate which maintained an internal reaction temperature of 40 OC to 48° C. After the addition was complete, the reaction mixture was stirred for another 10 minutes at 45° C., then cooled down to room temperature. The Pd/C was filtered out using a Teflon filter, and the solvent was evaporated. Ice water (1 L) was added to the residue, then the water was decanted and discarded. The residue was dissolved in diethyl ether, washed with water, then saturated sodium bicarbonate solution, then dried with magnesium sulfate and concentrated. The product was then purified on silica gel using isocratic DCM to give the product as a yellow oil (31.5 g, 83%).

Example Hc 2-(cyclohexyloxy)-6-nitrobenzonitrile

To a solution of cyclohexanol (46.8 grams, 0.467 mol) in anhydrous THF (1 L) was added sodium hydride (20.3 grams, 0.508 mol) at −40 OC under nitrogen. The reaction mixture was allowed to warm slowly to room temperature and stir for another 1 hour. It was then cooled down to −55° C. and 2,6-dinitrobenzonitrile (78.4 g, 0.406 mol) was added. The reaction was stirred at room temperature overnight, then cooled down to −20° C., and citric acid (23.4 grams, 0.122 mol) was added. The mixture was then poured into ice water (5 L) which contained citric acid (7.8 g, 0.041 mol), stirred for 15 minutes, and the precipitated product was collected by filtration. The crude product was recrystallized from isopropanol (750 mL, heated to boiling, then cooled down to 0° C.), filtered, washed with isopropanol (300 mL), then air dried to give 84.4 g yellow solid. The solid was dissolved in dichloromethane (169 mL) and filtered through a plug of alumina to give the title compound as a pale yellow solid (83.2 g, 83.2%). $^1$H NMR (400 MHz, DMSO-$d_6$) δ 1.4 (m, 4H), 1.6 (m, 2H), 1.7 (m, 2H), 1.9 (m, 2H), 4.75 (m, 1H), 7.79 (dd, J=2.0, 8.0 Hz, 1H), 7.84-7.91 (m, 2H).

Example 1

4-amino-5-(3-(isopropylamino)-2,2-dimethyl-3-oxo-propoxy)-2-methylquino-line-3-carboxylic acid

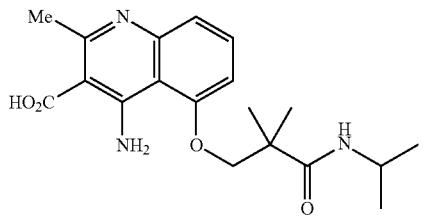 [SMILES: Cc1nc2cccc(OCC(C)(C)C(=O)NC(C)C)c2c(N)c1C(=O)O]

To a solution of ethyl 4-amino-5-(3-(isopropylamino)-2,2-dimethyl-3-oxopropoxy)-2-methylquinoline-3-carboxylate (Example 1a, 14.0 g, 36.2 mmol) in EtOH (140 mL) was added aqueous NaOH solution (2.0 N, 46 mL) at room temperature. The reaction mixture was stirred at 90° C. for 4 hrs. The resulting solution was neutralized at 0° C. to pH 7 with 6 N HCl, and concentrated under reduced pressure. The residue was re-dissolved in EtOH (400 mL) and water (25 mL), and treated with charcoal (200 mg) at 65° C. for 30 minutes. After removal of the charcoal by filtration, the filtrate was concentrated, and the resultant white solid was purified by re-crystallization from EtOH/$H_2O$ and dried under vacuum at 70° C. to give the title compound as a white solid (11.5 g, 89%). M.p.: 216-218° C. $^1$H NMR (400 MHz, DMSO-$d_6$) δ 1.01 (d, J=6.4 Hz, 6H), 1.24 (s, 6H), 2.75 (s, 3H), 3.86-3.93 (m, 1H), 4.17 (s, 2H), 7.01 (d, J=8.0 Hz, 1H), 7.28 (d, J=8.4 Hz, 1H), 7.57 (d, J=7.6 Hz, 1H), 7.67 (t, J=8.0 Hz, 1H), 8.83 (brs, 1H), 12.34 (brs, 1H), 12.78 (brs, 1H). MS 360 (MH$^+$).

Example 1a ethyl 4-amino-5-(3-(isopropylamino)-2,2-dimethyl-3-oxopropoxy)-2-methylquinoline-3-carboxylate Method A: to a solution of 3-(3-amino-2-cyanophenoxy)-N-isopropyl-2,2-dimethyl-propanamide (Example 1b, 11.35 g, 41.27 mmol) and ethyl 3-oxobutanoate (5.2 mL, 41.27 mmol) in anhydrous 1,2-dichloroethane (110 mL) and toluene (110 mL) was added dropwise SnCl$_4$ (9.66 mL, 82.55 mmol) at room temperature under nitrogen. The reaction mixture was heated to reflux for 3 hrs. The solution was cooled to room temperature and the solvent removed under reduced pressure. The residue was dissolved in EtOAc (600 mL) and neutralized at 0 OC to pH 8 with 6 N NaOH. The organic layer was separated and the aqueous layer was further extracted with EtOAc (100 mL). The combined organic layers were washed with brine, dried over Na$_2$SO$_4$, filtered and evaporated. The residue was purified by chromatography on Biotage SP-1, 40S×4 column eluting with 0-5% MeOH in dichloromethane, and re-crystallized from EtOAc to give the title compound as a cream white solid (14.0 g, 88%). $^1$H NMR (400 MHz, DMSO-$d_6$) δ 1.01 (d, J=6.4 Hz, 6H), 1.24 (s, 6H), 1.32 (t, J=7.2 Hz, 3H), 2.55 (s, 3H), 3.87-3.93 (m, 1H), 4.12 (s, 2H), 4.31 (q, J=7.2 Hz, 21H), 6.87 (d, J=7.2 Hz, 1H), 7.23 (d, J=8.4 Hz, 1H), 7.49-7.53 (m, 3H), 8.09 (s, 2H). MS 388 (MH$^+$).

Method B: to a solution of 3-(3-amino-2-cyanophenoxy)-N-isopropyl-2,2-dimethyl-propanamide (Example 1b, 10.0 g, 36.4 mmol) in ethyl 3-oxobutanoate (110 mL, 874 mmol, 24 eq.) was added anhydrous FeCl$_3$ (6.5 g, 40 mmol, 1.1 eq.) at room temperature under nitrogen. The black reaction mixture was stirred for 2 h at 110° C. Excess of ethyl 3-oxobutanoate was rotary evaporated at 80 OC. The thick resulting mixture was dissolved in EtOAc (200 mL). An aqueous solution of NaOH (15%) (80 ml) was slowly added at 0 OC. The mixture was stirred for 15 min. The organic layer was separated and the aqueous solution was extracted once more with EtOAc (100 mL). The combined organic layers were washed with brine, dried over Na$_2$SO$_4$. After evaporation of the solvent, the residue was purified by chromatography on silica gel eluting with 5-10% MeOH in DCM, and re-crystallized from EtOAc to give the title compound as an off-white solid (5.57 g, 40%).

Example 1b 3-(3-amino-2-cyanophenoxy)-N-isopropyl-2,2-dimethylpropanamide

To a solution of 3-hydroxy-N-isopropyl-2,2-dimethylpropanamide (Example 1c, 5.12 g, 32.15 mmol) in dry THF (100 mL) was added portion-wise NaH (60% in mineral oil, 1.41 g, 35.37 mmol) at 0° C. under nitrogen. The reaction mixture was stirred at 0° C. for about 30 minutes until bubbling ceased. 2-Amino-6-fluorobenzonitrile (4.38 g, 32.15 mmol) was added and the solution stirred at 80° C. overnight. The reaction mixture was quenched slowly with water at 0 OC, and concentrated under reduced pressure. The residue was taken up in EtOAc and washed consecutively with brine and water, dried over $Na_2SO_4$ and concentrated. The residue was purified by re-crystallization from EtOAc/hexane to give the title compound as a white crystalline solid (4.4 g, 50%). $^1$H NMR (400 MHz, CDCl$_3$) δ 1.18 (d, J=6.8 Hz, 6H), 1.32 (s, 6H), 3.94 (s, 2H), 4.04-4.12 (m, 1H), 4.43 (s, 2H), 5.98 (d, J=6.8 Hz, 1H), 6.21 (d, J=8.0 Hz, 1H), 6.32 (d, J=8.0 Hz, 1H), 7.21 (t, J=8.0 Hz, 1H). MS 276 (MH$^+$).

Example 1c 3-hydroxy-N-isopropyl-2,2-dimethylpropanamide

Method A: to a Parr Reactor was added methyl 3-hydroxy-2,2-dimethylpropanoate (66.0 g, 0.5 mol) and propan-2-amine (59.1 g, 1.0 mol) at room temperature. The reaction mixture was then stirred at 190° C. overnight. The reaction was cooled to room temperature and the solution concentrated under reduced pressure. The residue was dissolved in EtOAc and the solution successively washed with brine (5×), dried over $Na_2SO_4$, and evaporated under reduced pressure. The residue was co-evaporated with dry toluene (100 mL×2) to give the title compound as a colorless oil (38.76 g, 49%). $^1$H NMR (400 MHz, DMSO-d$_6$) δ 0.98 (s, 6H), 1.02 (d, J=6.4 Hz, 6H), 3.32 (d, J=5.2 Hz, 2H), 3.79-3.88 (m, 1H), 4.83 (t, J=5.2 Hz, 1H), 7.11 (d, J=7.2 Hz, 1H). MS 160 (MH$^+$).

Method B: to a solution of propan-2-amine (9.7 mL, 113.0 mmol) and 3-hydroxy-2,2-dimethylpropanoic acid (11.1 g, 94.2 mmol) in dichloromethane (500 mL) was added 1-(3-dimethylaminopropyl)-3-ethyl-carbodiimide hydrochloride (22.0 g, 113 mmol), 1-hydroxybenzotriazole monohydrate (17.3 g, 113 mmol), and triethylamine (16 mL, 113 mmol). The reaction mixture was stirred at room temperature overnight. The crude mixture was concentrated on the rotovap. The residue was taken up in EtOAc and washed with saturated NaHCO$_3$, brine, and water. The organic layer was dried over $Na_2SO_4$, filtered and evaporated under reduced pressure to afford the title compound as a clear oil (5.12 g, 34%). MS 160 (MH$^+$).

Example 2

4-amino-5-(3-(cyclopropylamino)-2,2-dimethyl-3-oxopropoxy)-2-methyl-quinoline-3-carboxylic acid

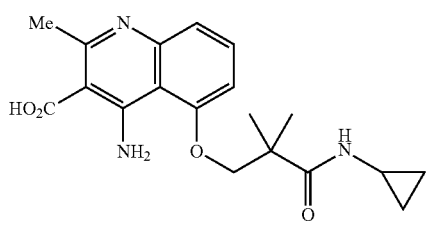 [SMILES: Cc1nc2cccc(OCC(C)(C)C(=O)NC3CC3)c2c(N)c1C(=O)O]

Prepared as in Example A from ethyl 4-amino-5-(3-(cyclopropylamino)-2,2-dimethyl-3-oxopropoxy)-2-methylquinoline-3-carboxylate (Example 2a) as a white solid (60%). M.p.: 227-229° C. $^1$H NMR (400 MHz, DMSO-d$_6$) δ 0.40-0.44 (m, 2H), 0.58-0.62 (m, 2H), 1.24 (s, 6H), 2.62 (m, 1H), 2.77 (s, 3H), 4.15 (s, 2H), 7.01 (d, J=8.0 Hz, 1H), 7.30 (d, J=8.0 Hz, 1H), 7.67 (t, J=8.0 Hz, 1H), 7.86 (d, J=4.0 Hz, 1H), 8.75 (brs, 1H), 12.25 (brs, 1H), 12.77 (brs, 1H). MS 358 (MH$^+$).

Example 2a ethyl 4-amino-5-(3-(cyclopropylamino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example 47b) and cyclopropanamine as a pale yellow solid (64%). $^1$H NMR (400 MHz, DMSO-d$_6$) δ 0.14-0.45 (m, 2H), 0.57-0.62 (m, 2H), 1.25 (s, 6H), 1.35 (t, J=8.0 Hz, 3H), 2.58 (s, 3H), 2.62-2.65 (m, 1H), 4.13 (s, 2H), 4.35 (q, J=8.0 Hz, 2H), 6.90 (d, 1H), 7.27 (d, 1H), 7.53 (t, J=8.0 Hz, 1H), 7.79 (d, J=4.0 Hz, 1H), 8.09 (s, 2H). MS 386 (MH$^+$).

Example 3

4-amino-5-(3-(cyclobutylamino)-2,2-dimethyl-3-oxopropoxy)-2-methylquino-line-3-carboxylic acid

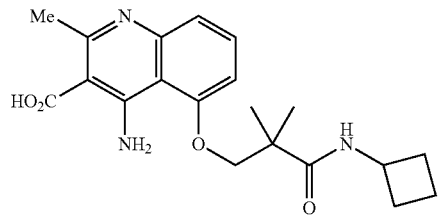 [SMILES: Cc1nc2cccc(OCC(C)(C)C(=O)NC3CCC3)c2c(N)c1C(=O)O]

Prepared as in Example A from ethyl 4-amino-5-(3-(cyclobutylamino)-2,2-dimethyl-3-oxopropoxy)-2-methylquinoline-3-carboxylate (Example 3a) as a white solid (45%). M.p.: 183-187° C. $^1$H NMR (400 MHz, DMSO-d$_6$) δ 1.24 (s, 611), 1.52-1.63 (m, 2H), 1.87-1.98 (m, 2H), 2.03-2.12 (m, 2H), 2.75 (s, 3H), 4.16 (s, 2H), 4.17-4.26 (m, 1H), 7.01 (d, J=8.0 Hz, 1H), 7.27 (d, J=8.0 Hz, 1H), 7.67 (t, J=8.0 Hz, 1H), 7.97 (d, J=8.0 Hz, 1H), 8.78 (brs, 1H), 12.35 (brs, 1H), 12.70 (brs, 1H). MS 372 (MH$^+$).

Example 3a ethyl 4-amino-5-(3-(cyclobutylamino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example 47b) and cyclobutanamine as an off-white solid (71%). MS 400 (MH$^+$).

Example 4

4-amino-5-(((1,4)-trans-4-isobutyramidocyclohexyl)oxy)-2-methylquinoline-3-carboxylic acid

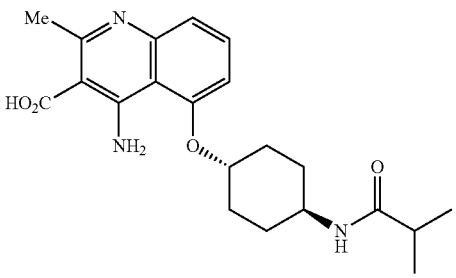 [SMILES: Cc1nc2cccc(O[C@H]3CC[C@H](NC(=O)C(C)C)CC3)c2c(N)c1C(=O)O]

Prepared as in Example A from ethyl 4-amino-5-(((1,4)-trans-4-isobutyramidocyclohexyl)oxy)-2-methylquinoline-3-carboxylate (Example 4a) as a white solid (86%). M.p.: 183-185 OC. $^1$H NMR (400 MHz, DMSO-$d_6$) δ 0.95 (s, 3H), 0.97 (s, 3H), 1.34-1.38 (m, 2H), 1.65-1.68 (m, 2H), 1.81-1.84 (m, 2H), 2.13-2.15 (m, 2H), 2.29-2.34 (m, 1H), 2.75 (s, 3H), 3.57-3.59 (m, 1H), 4.64 (m, 1H), 7.14 (d, J=8.4 Hz, 1H), 7.26 (d, J=8.4 Hz, 1H), 7.53 (s, 1H), 7.65 (m, 2H). MS 386 (MH$^+$).

Example 4a ethyl 4-amino-5-(((1,4)-trans-4-isobutyramidocyclohexyl)oxy)-2-methylquinoline-3-carboxylate Prepared as in Example Ba from N-((1,4)-trans-4-(3-amino-2-cyanophenoxy)cyclohexyl)isobutyramide (Example 4b) and ethyl acetoacetate as an off-white solid (88%). MS 414 (MH$^+$).

Example 4b

N-((1,4)-trans-4-(3-amino-2-cyanophenoxy)cyclohexyl)isobutyramide

Prepared as in Example Ca from N-((1,4)-trans-4-hydroxycyclohexyl)isobutyramide (Example 4c) and 2-amino-6-fluorobenzonitrile as an off-white solid (91%). MS 302 (MH$^+$).

Example 4c

N-((1,4)-trans-4-hydroxycyclohexyl)isobutyramide

Prepared as in Example Da from isobutyric acid and (1,4)-trans-4-aminocyclohexanol as a colorless oil (51%). MS 186 (MH$^+$).

Example 5

4-amino-2-methyl-5-(2-methyl-2-(3-methylbutanamido)propoxy)quinoline-3-carboxylic acid

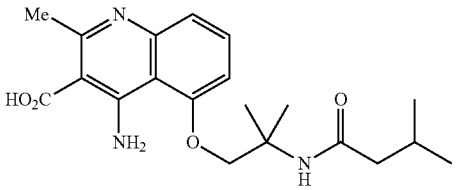 [SMILES: Cc1nc2cccc(OCC(C)(C)NC(=O)CC(C)C)c2c(N)c1C(=O)O]

Prepared as in Example A from ethyl 4-amino-2-methyl-5-(2-methyl-2-(3-methylbutan-amido)propoxy)quinoline-3-carboxylate (Example 5a) as a white solid (47%). M.p.: 195-198° C. $^1$H NMR (400 MHz, DMSO-$d_6$) δ 1.50 (d, J=4.0 Hz, 6H), 1.37 (s, 6H), 1.90-2.0 (m, 3H), 2.73 (s, 3H), 4.32 (s, 2H), 6.92 (d, J=8.0 Hz, 1H), 7.28 (d, J=8.0 Hz, 1H), 7.57 (t, J=8.0 Hz, 1H), 8.45 (s, 1H), 11.14 (brs, 1H), 12.94 (brs, 1H). MS 374 (MH$^+$).

Example 5a ethyl 4-amino-2-methyl-5-(2-methyl-2-(3-methylbutanamido)propoxy)-quinoline-3-carboxylate Prepared as in Example Da from ethyl 4-amino-5-(2-amino-2-methylpropoxy)-2-methylquinoline-3-carboxylate (Example Db) and 3-methylbutanoic acid as an off-white solid (100%). MS 402 (MH$^+$).

Example 6

4-amino-5-(2-isobutyramido-2-methylpropoxy)-2-methylquinoline-3-carboxylic acid

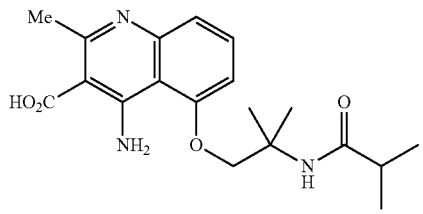 [SMILES: Cc1nc2cccc(OCC(C)(C)NC(=O)C(C)C)c2c(N)c1C(=O)O]

Prepared as in Example A from ethyl 4-amino-5-(2-isobutyramido-2-methylpropoxy)-2-methylquinoline-3-carboxylate (Example 6a) as a white solid (38%). M.p.: 184-186° C. $^1$H NMR (400 MHz, DMSO-$d_6$) δ 0.89 (d, J=8.0 Hz, 6H), 1.35 (s, 6H), 2.41 (m, 1H), 2.79 (s, 3H), 4.35 (s, 2H), 7.01 (d, J=8.0 Hz, 1H), 7.33 (d, J=8.0 Hz, 1H), 7.65 (t, J=8.0 Hz, 1H), 7.82 (s, 1H), 8.83 (brs, 1H), 12.10 (brs, 1H), 13.10 (brs, 1H). MS 360 (MH$^+$).

Example 6a ethyl 4-amino-5-(2-isobutyramido-2-methylpropoxy)-2-methylquinoline-3-carboxylate Prepared as in Example Da from ethyl 4-amino-5-(2-amino-2-methylpropoxy)-2-methylquinoline-3-carboxylate (Example Db) and isobutyric acid as a white solid (58%). MS 388 (MH$^+$).

Example 7

4-amino-2-methyl-5-(2-methyl-2-(tetrahydro-2H-pyran-4-carboxamido)-propoxy)quinoline-3-carboxylic acid

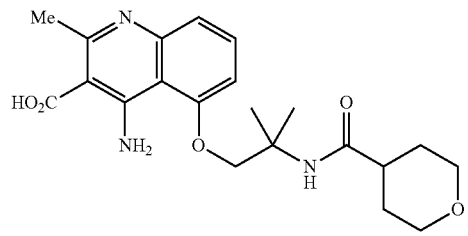

Prepared as in Example A from ethyl 4-amino-2-methyl-5-(2-methyl-2-(tetrahydro-2H-pyran-4-carboxamido)propoxy)quinoline-3-carboxylate (Example 7a) as a white solid (65%). M.p.: 170-173° C. $^1$H NMR (400 MHz, DMSO-d$_6$) δ 1.35 (s, 6H), 1.44-1.49 (m, 4H), 2.40 (m, 1H), 2.76 (s, 3H), 3.19-3.25 (m, 2H), 3.75-3.79 (m, 2H), 4.34 (s, 2H), 6.99 (d, J=8.0 Hz, 1H), 7.27 (d, J=8.0 Hz, 1H), 7.65 (t, J=8.0 Hz, 1H), 7.84 (s, 1H). MS 402 (MH$^+$).

Example 7a ethyl 4-amino-2-methyl-5-(2-methyl-2-(tetrahydro-2H-pyran-4-carbox-amido)propoxy)quinoline-3-carboxylate Prepared as in Example Da from ethyl 4-amino-5-(2-amino-2-methylpropoxy)-2-methylquinoline-3-carboxylate (Example Db) and tetrahydro-2H-pyran-4-carboxylic acid as a pale-yellow solid (63%). MS 430 (MH$^+$).

Example 8

4-amino-2-methyl-5-(2-methyl-2-propionamidopropoxy)quinoline-3-carboxylic acid

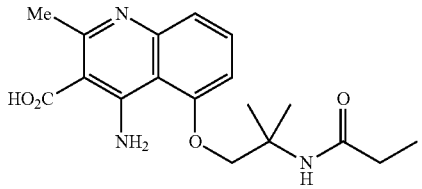 [SMILES: CCC(=O)NC(C)(C)COc1cccc2nc(C)c(C(=O)O)c(N)c12]

Prepared as in Example A from ethyl 4-amino-2-methyl-5-(2-methyl-2-propionamido-propoxy)quinoline-3-carboxylate (Example 8a) as a white solid (31%). M.p.: 189-193° C. $^1$H NMR (400 MHz, DMSO-d$_6$) δ 0.89 (t, J=8.0 Hz, 6H), 1.34 (s, 6H), 2.05 (q, J=8.0 Hz, 2H), 2.72 (s, 3H), 4.31 (s, 2H), 6.90 (d, J=8.0 Hz, 1H), 7.28 (d, J=8.0 Hz, 1H), 7.54 (t, J=8.0 Hz, 1H), 7.80 (s, 1H), 8.41 (brs, 1H), 11.02 (brs, 1H), 13.17 (brs, 1H). MS 346 (MH$^+$).

Example 8a ethyl 4-amino-2-methyl-5-(2-methyl-2-propionamidopropoxy)quinoline-3-carboxylate Prepared as in Example Da from ethyl 4-amino-5-(2-amino-2-methylpropoxy)-2-methylquinoline-3-carboxylate (Example Db) and propionic acid as a pale-yellow solid (23%). MS 374 (MH$^+$).

Example 9

4-amino-5-(2-(cyclobutanecarboxamido)-2-methylpropoxy)-2-methylquino-line-3-carboxylic acid

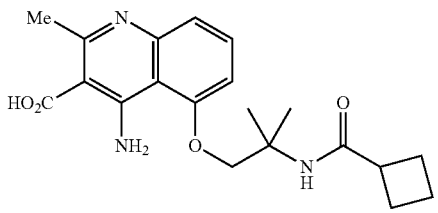 [SMILES: Cc1nc2cccc(OCC(C)(C)NC(=O)C3CCC3)c2c(N)c1C(=O)O]

Prepared as in Example A from ethyl 4-amino-5-(2-(cyclobutanecarboxamido)-2-methylpropoxy)-2-methylquinoline-3-carboxylate (Example 9A) as a white solid (65%).

M.p.: 186-190° C. 1H NMR (400 MHz, DMSO-d$_6$) δ 1.34 (s, 6H), 1.56-1.66 (m, 1H), 1.73-1.84 (m, 1H), 1.87-2.03 (m, 4H), 2.78 (s, 3H), 3.00-3.08 (m, 1H), 4.36 (s, 2H), 7.01 (d, J=8.0 Hz, 1H), 7.32 (d, J=8.0 Hz, 1H), 7.66 (t, J=8.0 Hz, 1H), 7.73 (s, 1H), 8.76 (brs, 1H), 12.01 (brs, 1H), 13.05 (brs, 1H). MS 372 (MH$^+$).

Example 9a ethyl 4-amino-5-(2-(cyclobutanecarboxamido)-2-methylpropoxy)-2-methylquinoline-3-carboxylate Prepared as in Example Da from ethyl 4-amino-5-(2-amino-2-methylpropoxy)-2-methylquinoline-3-carboxylate (Example Db) and cyclobutanecarboxylic acid as an off-white solid (61%). MS 400 (MH$^+$).

Example 10

4-amino-5-((1-isobutyrylpiperidin-4-yl)oxy)-2-methylquinoline-3-carboxylic acid

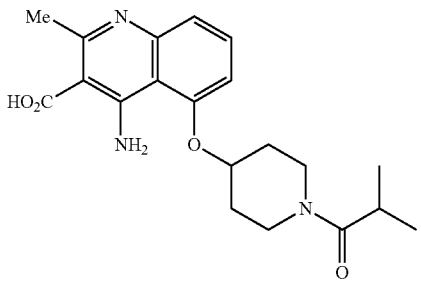 [SMILES: Cc1nc2cccc(OC3CCN(C(=O)C(C)C)CC3)c2c(N)c1C(=O)O]

Prepared as in Example A from ethyl 4-amino-5-((1-isobutyrylpiperidin-4-yl)oxy)-2-methylquinoline-3-carboxylate (Example 10a) as a white solid (88%). M.p.: 184-186 OC. $^1$H NMR (400 MHz, DMSO-d$_6$) δ 0.95 (s, 3H), 0.99 (t, 6H), 1.68-1.82 (m, 2H), 2.02-2.11 (m, 2H), 2.74 (s, 3H), 2.89 (m, 1H), 3.01 (m, 1H), 3.35 (m, 1H), 3.84 (m, 1H), 4.04 (m, 1H), 4.94 (m, 1H), 7.16 (d, J=8.4 Hz, 1H), 7.26 (d, J=7.6 Hz, 1H), 7.67 (t, J=8.4 Hz, 1H). MS 372 (MH$^+$).

Example 10a ethyl 4-amino-5-((1-isobutyrylpiperidin-4-yl)oxy)-2-methylquinoline-3-carboxylate Prepared as in Example Ba from 2-amino-6-((1-isobutyrylpiperidin-4-yl)oxy)benzonitrile (Example 10b) and ethyl acetoacetate as an off-white solid (82%). MS 400 (MH$^+$).

Example 10b 2-amino-6-((1-isobutyrylpiperidin-4-yl)oxy)benzonitrile

Prepared as in Example Ca from 1-(4-hydroxypiperidin-1-yl)-2-methylpropan-1-one (Example 10c) and 2-amino-6-fluorobenzonitrile as an off-white solid (87%). MS 288 (MH$^+$)

Example 10c 1-(4-hydroxypiperidin-1-yl)-2-methylpropan-1-one

Prepared as in Example Da from isobutyric acid and piperidin-4-ol as a colorless oil (43%). MS 172 (MH$^+$).

Example 12

4-amino-5-(3-(ethylamino)-2,2-dimethyl-3-oxopropoxy)-2-methylquinoline-3-carboxylic acid

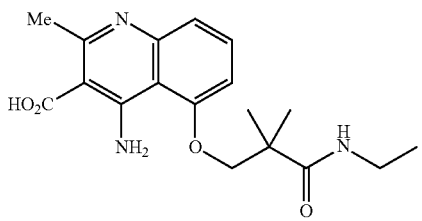 [SMILES: CCNC(=O)C(C)(C)COc1cccc2nc(C)c(C(=O)O)c(N)c12]

Prepared as in Example A from ethyl 4-amino-5-(3-(ethylamino)-2,2-dimethyl-3-oxopropoxy)-2-methylquinoline-3-carboxylate (Example 12a) as a white solid (75%). M.p.: 168-170° C. $^1$H NMR (400 MHz, DMSO-d$_6$) δ 0.96 (t, J=8 Hz, 3H), 1.24 (s, 6H), 3.06 (s, 3H), 3.09 (dq, J=1.6, 8.0 Hz, 2H), 4.14 (s, 2H), 7.00 (d, J=8.0 Hz, 1H), 7.26 (d, J=8.0 Hz, 1H), 7.66 (t, J=8.0 Hz, 1H), 7.90 (t, J=8.0 Hz, 1H), 8.85 (brs, 1H), 12.32 (brs, 1H), 12.70 (brs, 1H). MS 346 (MH$^+$).

Example 12a ethyl 4-amino-5-(3-(ethylamino)-2,2-dimethyl-3-oxopropoxy)-2-methyl-quinoline-3-carboxylate Prepared as in Example Da from 3-((4-amino-3-(ethoxycarbonyl)-2-methylquinolin-5-yl)oxy)-2,2-dimethylpropanoic acid (Example Eb) and ethylamine hydrochloride as an off-white solid (61%). MS 374 (MH$^+$).

Example 13

4-amino-2-methyl-5-(2-methyl-2-(2-(tetrahydro-2H-pyran-4-yl)acetamido)-propoxy)quinoline-3-carboxylic acid

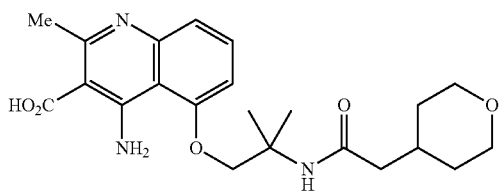 [SMILES: Cc1nc2cccc(OCC(C)(C)NC(=O)CC3CCOCC3)c2c(N)c1C(=O)O]

Prepared as in Example A from ethyl 4-amino-2-methyl-5-(2-methyl-2-(2-(tetrahydro-2H-pyran-4-yl)acetamido)propoxy)quinoline-3-carboxylate (Example 13a) as a white solid (28%). M.p.: 175-178° C. $^1$H NMR (400 MHz, DMSO-d$_6$) δ 1.06-1.13 (m, 2H), 1.35-1.38 (m, 8H), 1.79 (m, 1H), 1.98 (d, J=4.0 Hz, 21H), 2.77 (s, 3H), 3.10 (t, J=4.0 Hz, 2H), 3.60 (m, 2H), 4.34 (s, 2H), 7.01 (d, J=8.0 Hz, 1H), 7.27 (d, J=8.0 Hz, 1H), 7.65 (t, J=8.0 Hz, 1H), 7.88 (s, 1H), 8.76 (brs, 1H), 12.43 (brs, 1H), 12.71 (brs, 1H). MS 416 (MH$^+$).

Example 13a ethyl 4-amino-2-methyl-5-(2-methyl-2-(2-(tetrahydro-2H-pyran-4-yl)acetamido)propoxy)quinoline-3-carboxylate Prepared as in Example Da from ethyl 4-amino-5-(2-amino-2-methylpropoxy)-2-methylquinoline-3-carboxylate (Example Db) and 2-(tetrahydro-2H-pyran-4-yl)acetic acid as a yellow solid (37%). $^1$H NMR (400 MHz, DMSO-d$_6$) (1.05-1.08 (m, 2H), 1.30-1.38 (m, 11H), 1.79 (m, 1H), 1.97 (d, J=4.0 Hz, 2H), 2.56 (s, 3H), 3.07 (t, J=8.0 Hz, 2-1H), 3.61 (d, J=8.0 Hz, 2H), 4.28-4.34 (m, 4H), 6.87 (d, J=8.0 Hz, 1H), 7.23 (d, J=8.0 Hz, 1H), 7.49 (t, J=8.0 Hz, 1H), 7.73 (s, 1H), 8.21 (s, 2H). MS 444 (MH$^+$).

Example 14

4-amino-5-(3-((cyclopropylmethyl)amino)-2,2-dimethyl-3-oxopropoxy)-2-methylquinoline-3-carboxylic acid

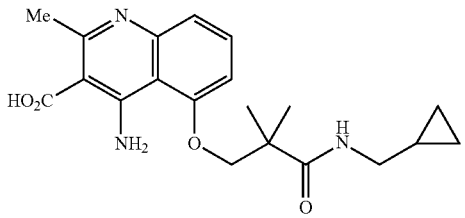 [SMILES: Cc1nc2cccc(OCC(C)(C)C(=O)NCC3CC3)c2c(N)c1C(=O)O]

Prepared as in Example A from ethyl 4-amino-5-(3-((cyclopropylmethyl)amino)-2,2-dimethyl-3-oxopropoxy)-2-methylquinoline-3-carboxylate (Example 14a) as a white solid (39%). M.p.: 177-179° C. $^1$H NMR (400 MHz, DMSO-d$_6$) δ 0.12-0.13 (m, 2H), 0.30-0.31 (m, 2H), 0.89 (m, 1H), 1.28 (s, 6H), 2.76 (s, 3H), 2.98 (t, J=4.0 Hz, 2H), 4.17 (s, 2H), 7.03 (d, J=8.0 Hz, 1H), 7.29 (d, J=8.0 Hz, 1H), 7.68 (t, J=8.0 Hz, 1H), 7.98 (t, J=8.0 Hz, 1H), 8.80 (brs, 1H), 12.26 (brs, 1H), 12.76 (brs, 1H). MS 372 (MH$^+$).

Example 14a ethyl 4-amino-5-(3-((cyclopropylmethyl)amino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example Eb) and cyclopropylmethanamine as a pale-yellow solid (80%). $^1$H NMR (400 MHz, DMSO-d$_6$) δ 0.12-0.13 (m, 2H), 0.29-0.31 (m, 2H), 0.90 (m, 1H), 1.27 (s, 6H), 1.33 (t, J=8.0 Hz, 3H), 2.56 (s, 3H), 2.97 (t, J=8.0 Hz, 2H), 4.14 (s, 2H), 4.32 (q, J=8.0 Hz, 2H), 6.88 (d, J=8.0 Hz, 1H), 7.26 (d, J=4.0 Hz, 1H), 7.53 (t, J=8.0 Hz, 1H), 7.91 (t, J=4.0 Hz, 1H), 8.11 (s, 2H). MS 400 (MH$^+$).

Example 15

4-amino-5-(3-(butylamino)-2,2-dimethyl-3-oxo-propoxy)-2-methylquinoline-3-carboxylic acid

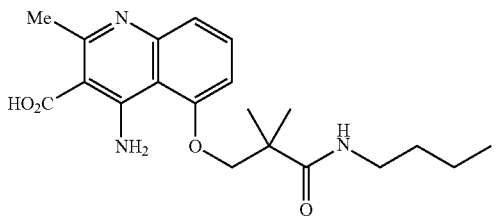 [SMILES: CCCCNC(=O)C(C)(C)COc1cccc2nc(C)c(C(=O)O)c(N)c12]

Prepared as in Example A from ethyl 4-amino-5-(3-(butylamino)-2,2-dimethyl-3-oxopropoxy)-2-methylquinoline-3-carboxylate (Example 15a) as an off-white solid (59%). M.p.: 195-199° C. $^1$H NMR (400 MHz, DMSO-$d_6$) δ 0.74 (t, J=8.0 Hz, 3H), 1.11-1.21 (m, 2H), 1.27 (s, 6H), 1.32-1.39 (m, 2H), 2.77 (s, 3H), 3.09 (q, J=8.0 Hz, 2H), 4.17 (s, 2H), 7.03 (d, J=8.0 Hz, 1H), 7.30 (d, J=8.0 Hz, 1H), 7.69 (t, J=8.0 Hz, 1H), 7.88 (t, J=8.0 Hz, 1H), 8.87 (brs, 1H), 12.41 (brs, 1H), 12.74 (brs, 1H). MS 374 (MH$^+$).

Example 15a ethyl 4-amino-5-(3-(butylamino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example Eb) and n-butylamine as a pale-yellow solid (91%). $^1$H NMR (400 MHz, DMSO-$d_6$) δ 0.74 (t, J=8.0 Hz, 3H), 1.15-1.20 (m, 2H), 1.27 (s, 6H), 1.32-1.38 (m, 5H), 2.57 (s, 3H), 3.06-3.11 (q, J=8.0 Hz, 2H), 4.14 (s, 2H), 4.35 (q, J=8.0 Hz, 2H), 6.90 (d, J=8.0 Hz, 1H), 7.26 (d, J=8.0 Hz, 1H), 7.53 (t, J=8.0 Hz, 1H), 7.81 (t, J=8.0 Hz, 1H), 8.10 (s, 2H). MS 402 (MH$^+$).

Example 16

4-amino-5-(2,2-dimethyl-3-oxo-3-(pentan-3-ylamino)propoxy)-2-methyl-quinoline-3-carboxylic acid

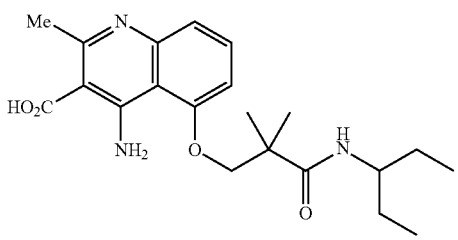 [SMILES: CCC(CC)NC(=O)C(C)(C)COc1cccc2nc(C)c(C(=O)O)c(N)c12]

Prepared as in Example A from ethyl 4-amino-5-(2,2-dimethyl-3-oxo-3-(pentan-3-ylamino)propoxy)-2-methylquinoline-3-carboxylate (Example 16a) as a white solid (72%). M.p.: 172-174° C. $^1$H NMR (400 MHz, DMSO-$d_6$) δ 0.69 (t, J=8.0 Hz, 6H), 1.29 (s, 6H), 1.32-1.42 (m, 4H), 2.76 (s, 3H), 3.59-3.64 (m, 1H), 4.21 (s, 2H), 7.03 (d, J=8.0 Hz, 1H), 7.29 (d, J=8.0 Hz, 1H), 7.43 (d, J=8.0 Hz, 1H), 7.69 (t, J=8.0 Hz, 1H), 8.79 (brs, 1H), 12.35 (brs, 1H), 12.73 (brs, 1H). MS 388 (MH$^+$).

Example 16a ethyl 4-amino-5-(2,2-dimethyl-3-oxo-3-(pentan-3-ylamino)propoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example Eb) and pentan-3-amine as a pale-yellow solid (78%). $^1$H NMR (400 MHz, DMSO-$d_6$) δ 0.68 (t, J=8.0 Hz, 6H), 1.27 (s, 6H), 1.31 (t, J=8.0 Hz, 3H), 1.37-1.42 (m, 4H), 2.54 (s, 3H), 3.56-3.61 (m, 1H), 4.16 (s, 2H), 4.30 (q, J=8.0 Hz, 2H), 6.87 (d, J=8.0 Hz, 1H), 7.23 (d, J=8.0 Hz, 1H), 7.32 (d, J=8.0 Hz, 1H), 7.51 (t, 0.1=8.0 Hz, 1H), 8.06 (s, 2H). MS 416 (MH$^+$).

Example 17

4-amino-2-methyl-5-(2-methyl-2-(2-morpholinoacetamido)propoxy)quinoline-3-carboxylic acid

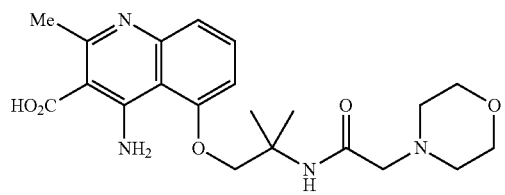 [SMILES: Cc1nc2cccc(OCC(C)(C)NC(=O)CN3CCOCC3)c2c(N)c1C(=O)O]

Prepared as in Example A from ethyl 4-amino-2-methyl-5-(2-methyl-2-(2-morpholino-acetamido)propoxy)quinoline-3-carboxylate (Example 17a) as a white solid (32%). M.p.: 173-175° C. $^1$H NMR (400 MHz, DMSO-$d_6$) δ 1.39 (s, 6H), 2.35 (t, J=4.8 Hz, 4H), 2.74 (s, 3H), 2.85 (s, 2H), 3.47 (t, J=4.8 Hz, 4H), 4.35 (s, 2H), 7.00 (d, J=8.0 Hz, 1H), 7.27 (d, J=8.4 Hz, 1H), 7.63 (t, J=8.0 Hz, 1H), 7.71 (s, 1H). MS 417 (MH$^+$).

Example 17a ethyl 4-amino-2-methyl-5-(2-methyl-2-(2-morpholinoacetamido)propoxy)quinoline-3-carboxylate Prepared as in Example Da from ethyl 4-amino-5-(2-amino-2-methylpropoxy)-2-methylquinoline-3-carboxylate (Example Db) and 2-morpholinoacetic acid as a yellow solid (37%). MS 445 (MH$^+$).

Example 18

4-amino-5-(3-(isobutylamino)-2,2-dimethyl-3-oxopropoxy)-2-methylquino-line-3-carboxylic acid

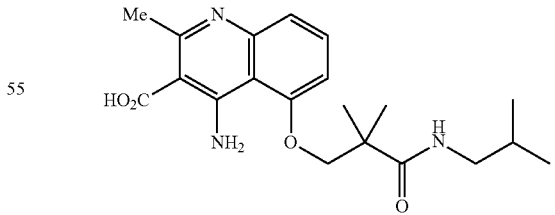

Prepared as in Example A from ethyl 4-amino-5-(3-(isobutylamino)-2,2-dimethyl-3-oxopropoxy)-2-methylquinoline-3-carboxylate (Example 18a) as an off-white solid (60%). M.p.: 176-179° C. $^1$H NMR (400 MHz, DMSO-$d_6$) δ 0.73 (d, J=6.8 Hz, 6H), 1.27 (s, 6H), 1.65-1.75 (m, 1H), 2.77 (s, 3H), 2.89 (t, J=6.4 Hz, 2H), 4.17 (s, 2H), 7.01 (d, J=8.4 Hz, 1H), 7.31 (d, J=8.4 Hz, 1H), 7.67 (t, J=8.4 Hz, 1H), 7.90 (t, J=5.8 Hz, 1H), 8.84 (brs, 1H), 12.16 (brs, 1H), 12.91 (brs, 1H). MS 374 (MH+).

Example 18a ethyl 4-amino-5-(3-(isobutylamino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example Eb) and isobutylamine as an off-white solid (82%). MS 402 (MH+).

Example 19

4-amino-5-(3-((cyclobutylmethyl)amino)-2,2-dimethyl-3-oxopropoxy)-2-methylquinoline-3-carboxylic acid

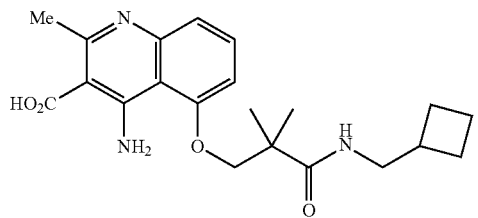 [SMILES: Cc1nc2cccc(OCC(C)(C)C(=O)NCC3CCC3)c2c(N)c1C(=O)O]

Prepared as in Example A from ethyl 4-amino-5-(3-((cyclobutylmethyl)amino)-2,2-dimethyl-3-oxopropoxy)-2-methylquinoline-3-carboxylate (Example 19a) as a white solid (54%). M.p.: 170-172° C. $^1$H NMR (400 MHz, DMSO-$d_6$) δ 1.26 (s, 6H), 1.54-1.71 (m, 4H), 1.76-1.84 (m, 2H), 2.35-2.42 (m, 1H), 2.76 (s, 3H), 3.10 (t, J=6.0 Hz, 2H), 4.18 (s, 2H), 7.13 (d, J=8.4 Hz, 1H), 7.33 (d, J=8.0 Hz, 1H), 7.77 (t, J=8.0 Hz, 1H), 7.87 (t, J=6.4 Hz, 1H), 9.21 (brs, 1H), 10.92 (brs, 1H). MS 386 (MH+).

Example 19a ethyl 4-amino-5-(3-((cyclobutylmethyl)amino)-2,2-dimethyl-3-oxopropoxy)-2-methylquinoline-3-carboxylate Prepared as in Example Da from 3-((4-amino-3-(ethoxycarbonyl)-2-methylquinolin-5-yl)oxy)-2,2-dimethylpropanoic acid (Example Eb) and cyclobutylmethanamine as an off-white solid (67%). MS 414 (MH+).

Example 20

5-(2-(6-Ammoniohexanamido)-2-methylpropoxy)-3-carboxy-2-methylquinolin-4-aminium trifluoroacetate

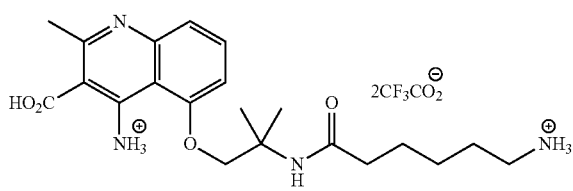 [SMILES: Cc1nc2cccc(OCC(C)(C)NC(=O)CCCCC[NH3+])c2c([NH3+])c1C(=O)O]

A solution of 4-amino-5-(2-(6-(tert-butoxycarbonylamino)hexanamido)-2-methylpropoxy)-2-methylquinoline-3-carboxylic acid (Example 20a) (59.6 mg, 0.12 mmol) in CH$_2$Cl$_2$ (9.0 mL) was treated with trifluoroacetic acid (1.0 mL) at room temperature. After being stirred at room temperature for 2 h the reaction mixture was evaporated to dryness. The residue was dissolved in H$_2$O (5.0 mL) and the product was isolated by preparative HPLC (RPC18, H$_2$O→CH$_3$CN gradient). The appropriate fractions were collected and evaporated under reduced pressure. The residue was dried in a dessicator over phosphorus pentoxide to give 43.6 mg (58%) of 5-(2-(6-ammoniohexanamido)-2-methylpropoxy)-3-carboxy-2-methylquinolin-4-aminium trifluoroacetate as a white solid. $^1$H NMR (400 MHz, DMSO-$d_6$) δ 13.56 (s, 1H), 9.98 (s, 1H), 9.40 (s, 1H), 7.88 (t, J=8.3 Hz, 1H), 7.75 (s, 1H), 7.72-7.56 (m, 3H), 7.42 (d, J=7.9 Hz, 1H), 7.25 (d, J=8.1 Hz, 1H), 4.42 (s, 2H), 2.81 (s, 3H), 2.72-2.60 (m, 2H), 2.08 (t, J=7.3 Hz, 2H), 1.50-1.39 (m, 4H), 1.38 (s, 6H), 1.26-1.14 (m, 2H). MS 404 (M+).

Example 20a

4-Amino-5-(2-(6-(tert-butoxycarbonylamino)hexanamido)-2-methylpropoxy)-2-methylquinoline-3-carboxylic acid A solution of 6-(tert-butoxycarbonylamino)hexanoic acid (0.21 g, 0.90 mmol) in dry DMF (10 mL) was treated with triethylamine (0.46 g, 4.51 mmol, 0.63 mL) and N,N,N',N'-tetramethyl-O—(N-succinimidyl)uronium tetrafluoroborate (TSTU) (0.30 g, 0.99 mmol) at room temperature under a nitrogen atmosphere. The reaction mixture was stirred at room temperature over 3 h and then a solution of 5-(2-ammonio-2-methylpropoxy)-3-carboxy-2-methylquinolin-4-aminium chloride (Example 20b) (0.33 g, 0.90 mmol) and triethylamine (0.46 g, 4.51 mmol, 0.63 mL) in dry DMF was added dropwise at room temperature. The obtained mixture was stirred at room temperature over 3 days and the solvent was evaporated. The residue was dissolved in a mixture of MeOH and H$_2$O (50 mL, 1:1) and the product was isolated by preparative HPLC (RPC18, H$_2$O→CH$_3$CN gradient). The appropriate fractions were collected and evaporated under reduced pressure. The residue was dried in a dessicator over phosphorus pentoxide to give 0.21 g (45%) of 4-amino-5-(2-(6-(tert-butoxycarbonylamino)hexanamido)-2-methylpropoxy)-2-methylquinoline-3-carboxylic acid as a white solid. $^1$H NMR (400 MHz, DMSO-$d_6$) δ 12.95-12.65 (m, 1H), 12.45-11.95 (m, 1H), 9.05-8.60 (m, 1H), 7.84 (s, 1H), 7.67 (t, J=8.0 Hz, 1H), 7.29 (d, J=8.2 Hz, 1H), 7.02 (d, J=8.1 Hz, 1H), 6.71 (t, J=5.6 Hz, 1H), 4.36 (s, 2H), 2.78 (s, 3H), 2.70 (q, J=6.4 Hz, 2H), 2.05 (t, J=7.3 Hz, 2H), 1.45-1.34 (m, 2H), 1.36 (s, 3H), 1.34 (s, 3H), 1.30-1.19 (m, 2H), 1.14-1.03 (m, 2H). MS 503 (MH+).

Example 20b 5-(2-Ammonio-2-methylpropoxy)-3-carboxy-2-methylquinolin-4-aminium chloride To a solution of ethyl 4-amino-5-(2-amino-2-methylpropoxy)-2-methylquinoline-3-carboxylate (Example Db) (0.65 g, 2.05 mmol) in EtOH (35 mL) was added a solution of NaOH in H$_2$O (2.0 M, 5.2 mL) at room temperature under a nitrogen atmosphere. The obtained reaction mixture was heated at 80 OC over 3 h and cooled to room temperature. The pH of the cold mixture was adjusted to 1 with a solution of HCl (1.5 M) and the acidified solution was evaporated to dryness. The residue was dissolved in a mixture of EtOH and H₂O (30 mL, 1:1) and the product was isolated by preparative HPLC (RPC18, H₂O→CH₃CN gradient). The appropriate fractions were collected and evaporated under reduced pressure. The residue was dried in a dessicator over phosphorus pentoxide to give 0.41 g (54%) 5-(2-ammonio-2-methylpropoxy)-3-carboxy-2-methylquinolin-4-aminium chloride as a white solid. $^1$H NMR (400 MHz, DMSO-$d_6$) δ 10.05-9.90 (m, 1H), 9.15-9.00 (m, 1H), 8.69-8.57 (m, 3H), 7.91 (t, J=8.3 Hz, 1H), 7.65 (d, J=8.0 Hz, 1H), 7.38 (d, J=8.3 Hz, 1H), 4.39 (s, 2H), 2.84 (s, 3H), 1.44 (s, 6H). MS 291 (M$^+$)

Example 21

4-amino-2-methyl-5-((1-propionylpiperidin-4-yl)methoxy)quinoline-3-carboxylic acid

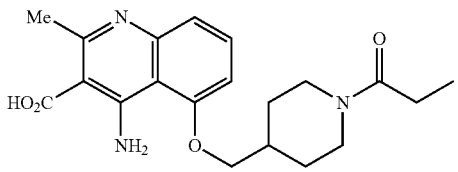 [SMILES: CCC(=O)N1CCC(COc2cccc3nc(C)c(C(=O)O)c(N)c23)CC1]

Prepared as in Example A from ethyl 4-amino-2-methyl-5-((l-propionylpiperidin-4-yl)methoxy)quinoline-3-carboxylate (Example 21a) as an off-white solid (55%). M.p.: 168-170° C. $^1$H NMR (400 MHz, DMSO-$d_6$) δ 0.96 (t, J=7.6 Hz, 3H), 1.08-1.25 (m, 2H), 1.81 (t, J=15.6 Hz, 2H), 2.19-2.26 (m, 1H), 2.30 (q, J=7.2 Hz, 2H), 2.55 (t, J=12 Hz, 1H), 2.75 (s, 3H), 3.01 (t, J=12 Hz, 1H), 3.88 (d, J=13.6 Hz, 1H), 4.1 (d, J=5.6 Hz 2H), 4.42 (d, J=13.2 Hz, 1H), 7.02 (d, J=8.4 Hz, 1H), 7.27 (d, J=7.6 Hz, 1H), 7.65 (t, J=8.4 Hz, 1H). MS 372 (MH$^+$).

Example 21a ethyl 4-amino-2-methyl-5-((1-propionylpiperidin-4-yl)methoxy)quinoline-3-carboxylate Prepared as in Example Ba from 2-amino-6-((l-propionylpiperidin-4-yl)methoxy)benzonitrile (Example 21b) and ethyl acetoacetate as an off-white solid (41%). MS 400 (MH$^+$).

Example 21 b 2-amino-6-((1-propionylpiperidin-4-yl)methoxy)benzonitrile

Prepared as in Example 22a from 1-(4-(hydroxymethyl)piperidin-1-yl)propan-1-one (Example 21c) and 2-amino-6-fluorobenzonitrile as a pale-yellow solid (15%). MS 288 (MH$^+$).

Example 21c 1-(4-(hydroxymethyl)piperidin-1-yl)propan-1-one

Prepared as in Example 24a from propionyl chloride and piperidin-4-ylmethanol as a colorless oil (40%). MS 172 (MH$^+$).

Example 22

4-amino-2-methyl-5-(((1,4)-trans-4-(methylcarbamoyl)cyclohexyl)oxy)quinoline-3-carboxylic acid

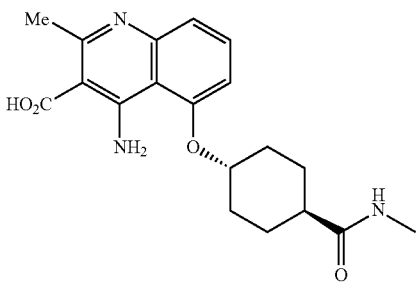 [SMILES: CNC(=O)[C@H]1CC[C@H](Oc2cccc3nc(C)c(C(=O)O)c(N)c23)CC1]

Prepared as in Example A from ethyl 4-amino-2-methyl-5-(((1,4)-trans-4-(methylcarbamoyl)cyclohexyl)oxy)quinoline-3-carboxylate (Example 22a) as a white solid (42%). M.p.: 195-198° C. $^1$H NMR (400 MHz, DMSO-$d_6$) δ 1.55-1.80 (m, 6H), 2.00-2.10 (m, 2H), 2.20-2.30 (m, 1H), 2.55 (d, J=8.0 Hz, 3H), 2.76 (s, 3H), 4.96 (s, 1H), 7.07 (d, J=8.0 Hz, 1H), 7.27 (d, J=8.0 Hz, 1H), 7.66-7.72 (m, 1H), 8.76 (brs, 1H), 12.00 (brs, 1H), 12.83 (brs, 1H). MS 358 (MH$^+$).

Example 22a ethyl 4-amino-2-methyl-5-(((1,4)-trans-4-(methylcarbamoyl)cyclohexyl-)oxy)quinoline-3-carboxylate Prepared as in Example Ba from (1,4)-trans-4-(3-amino-2-cyanophenoxy)-N-methylcyclohexanecarboxamide (Example 22b) and ethyl acetoacetate as a yellow solid (43%). MS 386 (MH$^+$).

Example 22b (1,4)-trans-4-(3-amino-2-cyanophenoxy)-N-methylcyclohexanecarboxamide Prepared as in Example Ec from 4-(2-cyano-3-nitrophenoxy)-N-methylcyclohexanecarboxamide (Example 22c) as pale-yellow solid (41%). MS 274 (MH$^+$).

Example 22c 4-(2-cyano-3-nitrophenoxy)-N-methylcyclohexanecarboxamide

Prepared as in Example Da from 4-(2-cyano-3-nitrophenoxy)cyclohexanecarboxylic acid (Example 22d) and methylamine hydrochloride as an orange solid (80%). MS 304 (MH$^+$).

Example 22d 4-(2-cyano-3-nitrophenoxy)cyclohexanecarboxylic acid

Prepared as in Example Ed from 4-hydroxycyclohexanecarboxylic acid and 2,6-dinitrobenzonitrile as a brown solid (50%). MS 291 (MH$^+$).

Example 23

4-amino-5-(3-(isopropylamino)-2,2-dimethyl-3-oxo-propoxy)-2-methylquino-line-3-carboxylic acid phosphate

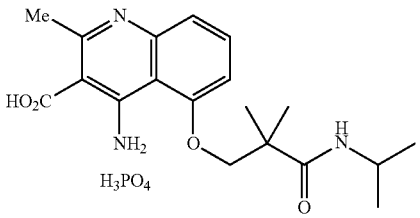

Prepared as in Example F from 4-amino-5-(3-(isopropylamino)-2,2-dimethyl-3-oxopropoxy)-2-methylquinoline-3-carboxylic acid (Example 1) and $H_3PO_4$ as a white solid (100%). $^1$H NMR (400 MHz, DMSO-$d_6$) δ 1.01 (d, J=6.4 Hz, 6H), 1.25 (s, 6H), 2.76 (s, 3H), 3.86-3.95 (m, 1H), 4.17 (s, 2H), 7.04 (d, J=8.0 Hz, 1H), 7.30 (dd, J=8.0 Hz, 0.8 Hz, 1H), 7.57 (d, J=8.0 Hz, 1H), 7.70 (t, J=8.0 Hz, 1H). MS 360 (MH$^+$+H-H$_3$PO$_4$).

Example 24 sodium 4-amino-5-(3-(isopropylamino)-2,2-dimethyl-3-oxopropoxy)-2-methylquinoline-3-carboxylate

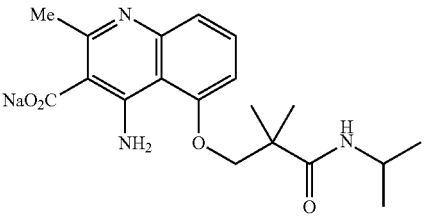

Prepared as in Example G from 4-amino-5-(3-(isopropylamino)-2,2-dimethyl-3-oxopropoxy)-2-methylquinoline-3-carboxylic acid (Example 1) and NaHCO$_3$ as a white solid (100%). $^1$H NMR (400 MHz, DMSO-$d_6$) δ 1.01 (d, J=6.4 Hz, 6H), 1.23 (s, 6H), 2.56 (s, 3H), 3.86-3.94 (m, 1H), 4.07 (s, 2H), 6.66 (d, J=8.0 Hz, 1H), 7.14 (d, J=8.0 Hz, 1H), 7.32 (t, J=8.0 Hz, 1H), 7.48 (d, J=8.0 Hz, 1H). MS 360 (MH$^+$+H-Na).

The following compounds in Table G were synthesized following the procedures described above.

TABLE G

| Compound No. | Compound | MS (MH+) |
|---|---|---|
| G-1 | 4-amino-5-(2-(4-hydroxycyclohexanecarboxamido)-2-methylpropoxy)-2-methylquinoline-3-carboxylic acid | 416 |
| G-2 | 4-amino-5-((4-(ethylcarbamoyl)cyclohexyl)oxy)-2-methylquinoline-3-carboxylic acid | 372 |
| G-3 | 4-amino-5-(2,2-dimethyl-3-oxo-3-(pyrrolidin-1-yl)propoxy)-2-methylquinoline-3-carboxylic acid | 372 |

TABLE G-continued

| Compound No. | Compound | MS (MH+) |
| --- | --- | --- |
| G-4 | 4-amino-5-(2-(isopropylamino)-2-oxoethoxy)-2-methylquinoline-3-carboxylic acid | 318 |
| G-5 | 4-amino-5-(2,2-dimethyl-3-(methylamino)-3-oxopropoxy)-2-methylquinoline-3-carboxylic acid | 332 |
| G-6 | 5-((1-acetylpiperidin-4-yl)oxy)-4-amino-2-methylquinoline-3-carboxylic acid | 344 |
| G-7 | 4-amino-5-((1-isobutyrylpiperidin-3-yl)oxy)-2-methylquinoline-3-carboxylic acid | 372 |
| G-8 | 4-amino-2-methyl-5-((1-pivaloylpiperidin-4-yl)methoxy)quinoline-3-carboxylic acid | 400 |

TABLE G-continued

| Compound No. | Compound | MS (MH+) |
|---|---|---|
| G-9 | 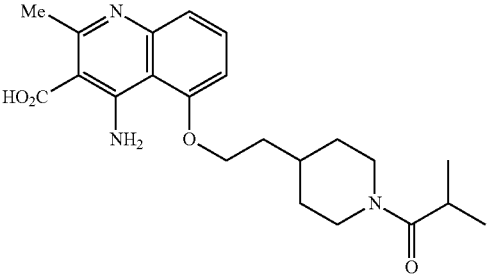 [SMILES: Cc1nc2cccc(OCCC3CCN(C(=O)C(C)C)CC3)c2c(N)c1C(=O)O]<br>4-amino-5-(2-(1-isobutyrylpiperidin-4-yl)ethoxy)-2-methylquinoline-3-carboxylic acid | 400 |
| G-10 | 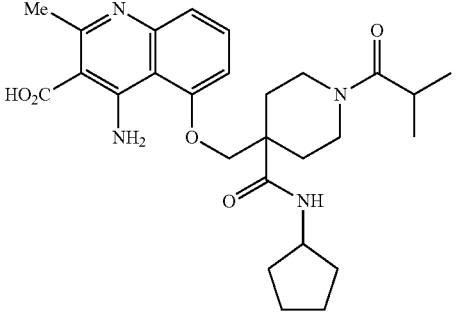 [SMILES: Cc1nc2cccc(OCC3(C(=O)NC4CCCC4)CCN(C(=O)C(C)C)CC3)c2c(N)c1C(=O)O]<br>4-amino-5-((4-(cyclopentylcarbamoyl)-1-isobutyrylpiperidin-4-yl)methoxy)-2-methylquinoline-3-carboxylic acid | 497 |
| G-11 | 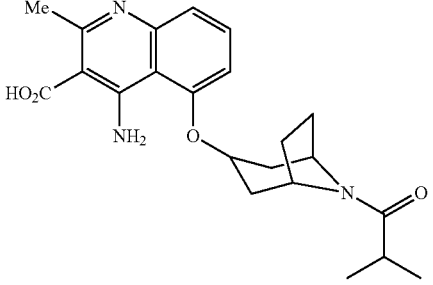 [SMILES: Cc1nc2cccc(OC3CC4CCC(C3)N4C(=O)C(C)C)c2c(N)c1C(=O)O]<br>4-amino-5-(((1R,5S)-8-isobutyryl-8-azabicyclo[3.2.1]octan-3-yl)oxy)-2-methylquinoline-3-carboxylic acid | 398 |
| G-12 | 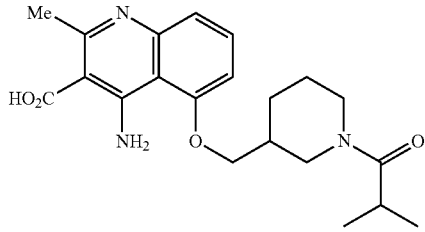 [SMILES: Cc1nc2cccc(OCC3CCCN(C(=O)C(C)C)C3)c2c(N)c1C(=O)O]<br>4-amino-5-((1-isobutyrylpiperidin-3-yl)methoxy)-2-methylquinoline-3-carboxylic acid | 386 |
| G-13 | 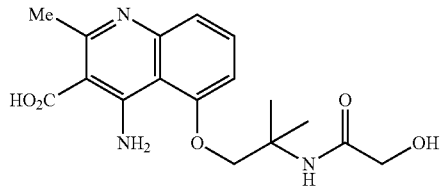 [SMILES: Cc1nc2cccc(OCC(C)(C)NC(=O)CO)c2c(N)c1C(=O)O]<br>4-amino-5-(2-(2-hydroxyacetamido)-2-methylpropoxy)-2-methylquinoline-3-carboxylic acid | 348 |

TABLE G-continued

| Compound No. | Compound | MS (MH+) |
|---|---|---|
| G-14 | 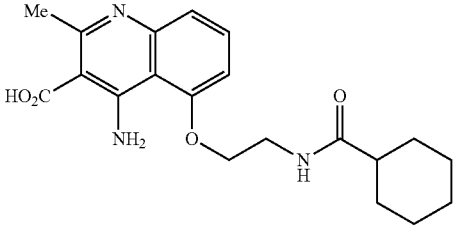 [SMILES: Cc1nc2cccc(OCCNC(=O)C3CCCCC3)c2c(N)c1C(=O)O]<br>4-amino-5-(2-(cyclohexanecarboxamido)ethoxy)-2-methylquinoline-3-carboxylic acid | 372 |
| G-15 | 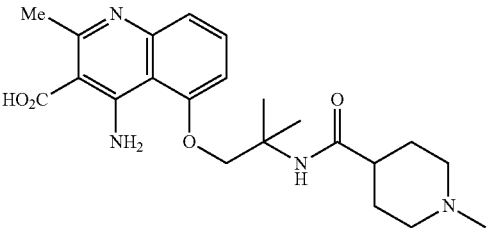 [SMILES: Cc1nc2cccc(OCC(C)(C)NC(=O)C3CCN(C)CC3)c2c(N)c1C(=O)O]<br>4-amino-2-methyl-5-(2-methyl-2-(1-methylpiperidine-4-carboxamido)propoxy)quinoline-3-carboxylic acid | 415 |
| G-16 | 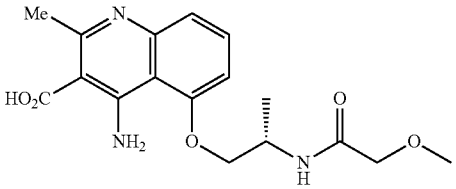 [SMILES: COCC(=O)N[C@@H](C)COc1cccc2nc(C)c(C(=O)O)c(N)c12]<br>(S)-4-amino-5-(2-(2-methoxyacetamido)propoxy)-2-methylquinoline-3-carboxylic acid | 348 |
| G-17 | 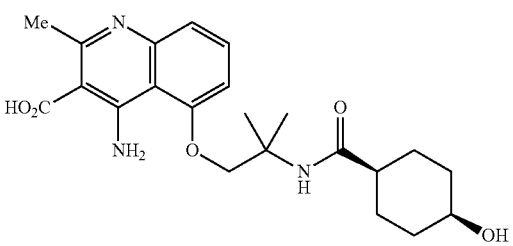 [SMILES: Cc1nc2cccc(OCC(C)(C)NC(=O)[C@H]3CC[C@@H](O)CC3)c2c(N)c1C(=O)O]<br>4-amino-5-(2-((1s,4s)-4-hydroxycyclohexanecarboxamido)-2-methylpropoxy)-2-methylquinoline-3-carboxylic acid | 416 |
| G-18 | 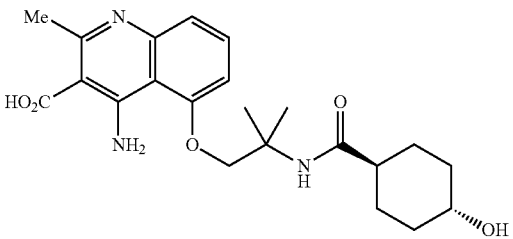 [SMILES: Cc1nc2cccc(OCC(C)(C)NC(=O)[C@H]3CC[C@H](O)CC3)c2c(N)c1C(=O)O]<br>4-amino-5-(2-((1r,4r)-4-hydroxycyclohexanecarboxamido)-2-methylpropoxy)-2-methylquinoline-3-carboxylic acid | 416 |

TABLE G-continued

| Compound No. | Compound | MS (MH+) |
|---|---|---|
| G-19 | 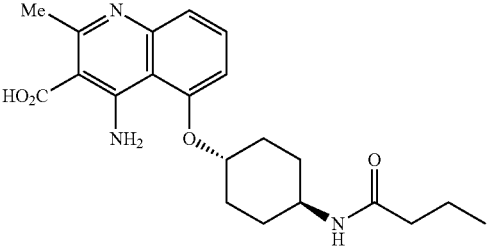 [SMILES: CCCC(=O)N[C@H]1CC[C@H](Oc2cccc3nc(C)c(C(=O)O)c(N)c23)CC1]<br>4-amino-5-(((1r,4r)-4-butyramidocyclohexyl)oxy)-2-methylquinoline-3-carboxylic acid | 386 |
| G-20 | 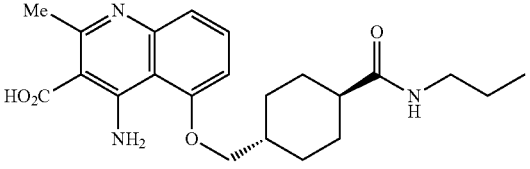 [SMILES: CCCNC(=O)[C@H]1CC[C@H](COc2cccc3nc(C)c(C(=O)O)c(N)c23)CC1]<br>4-amino-2-methyl-5-(((1r,4r)-4-(propylcarbamoyl)cyclohexyl)methoxy)quinoline-3-carboxylic acid | 400 |

Biological Tests

Experiment 1

Screening for Sweet Enhancers hT1R2/R3-mammalian Gal5 cells were seeded in 384-well-clear bottom plates (Fisher) at a density of ~32,000 cells/well and grown overnight. On the day of the experiment, hT1R2/R3-mammalian Gal5 were loaded with the calcium indicator Fluo3AM (4 mM) (Invitrogen, Carlsbad, Calif.) in D-PBS (Invitrogen, Carlsbad, Calif.) using a Multidrop. Cells were incubated for 1 hour at room temperature and excess dye was washed out with D-PBS using an EMBLA cell washer (Molecular Devices, Sunnyvale, Calif.), leaving a residual volume of 25 ml/well. Sweeteners and test compounds were prepared at 4× final concentration and mixed 1:1 in a 384-well Greiner plate (bringing the sweeteners and test compounds concentrations down to 2× final concentration). After 30 minutes of rest time at room temperature, Fluo3AM-loaded cell plates, and the sweetener/compound plate mixture were loaded into a Fluorometric Imaging Plate Reader (FLIPR) (Molecular Devices, Sunnyvale, Calif.). Imaging was performed using a 480 nm excitation and a 535 emission and was initiated with the acquisition of the baseline fluorescence for a period of 7 seconds. Then, the cells were stimulated on line with addition of 25 ml stimuli/well. Subsequent images were acquired every other second for a period of 2 minutes. Raw fluorescence counts were then normalized in each well (using custom made data import software) by calculating delta F/f values (maximum fluorescent count obtained after stimulation−minimal fluorescent count obtained before stimulation/minimal fluorescent count obtained before stimulation). $EC_{50}$s were determined using a non-linear regression algorithm (GraphPad PRISM, San Diego, Calif.), where the Hill slope, bottom asymptotes and top asymptotes were allow to vary. Enhancement properties of test compounds were quantified by determining the magnitude of the leftward shift in the sweeteners $EC_{50}$ values (or an $EC_{50}$ ratio): the value of the $EC_{50}$ measured in the absence of the enhancer divided by the value of the $EC_{50}$ measured in the presence of the enhancer).

The present compounds have been tested and shown sweet taste enhancing activities for sucrose, sucralose, and/or fructose as shown in Table E (EC50 ratio for sucrose at about 10 μM), Table F (EC50 ratio for sucralose at about 10 μM), and Table H (EC50 ratio for fructose at about 50 M). Specifically, the EC50 ratio of the test compounds for sucrose, sucralose, and/or fructose enhancement are greater than about 2 at about 10 LM or about 50 μM. The compounds listed in Tables E, F and H are Examples described above. For example, Compound C6 listed in Tables E and F is Example 18 described above.

TABLE E

Sucrose Enhancement at 10 μM

| Compound | EC50 Ratio | Compound | EC50 Ratio |
|---|---|---|---|
| D5 | 5.3 | M5 | 12.4 |
| K5 | 6.6 | T5 | 10.5 |
| Q5 | 65.1 | G5 | 4.0 |
| A6 | 20.6 | J6 | 2.9 |
| L6 | 9.3 | F6 | 7.4 |
| Y5 | 5.5 | N5 | 3.5 |
| E5 | 4.1 | U5 | 9.4 |
| E6 | 5.8 | G6 | 2.9 |
| R5 | 20.2 | T6 | 2.3 |
| M6 | 3.3 | H6 | 14.8 |
| L5 | 6.1 | V5 | 4.8 |
| B6 | 3.8 | O5 | 6.0 |
| Z5 | 31.1 | N6 | 2.4 |
| Q6 | 3.6 | I6 | 16.5 |
| F5 | 7.9 | P6 | 2.1 |
| S5 | 4.3 | I5 | 3.3 |
| C6 | 11.0 | U6 | 2.4 |
| J5 | 45.8 | W5 | 4.8 |
| D6 | 2.6 | O6 | 11.4 |
| X5 | 5.8 | | |

TABLE F

Sucralose Enhancement at 10 μM

| Compound | EC50 Ratio | Compound | EC50 Ratio |
|---|---|---|---|
| D5 | 2.9 | S5 | 2.6 |
| K5 | 3.4 | S5 | 2.6 |
| Q5 | 14.3 | C6 | 3.8 |
| A6 | 23.8 | M5 | 3.5 |
| L6 | 5.7 | T5 | 8.2 |
| Y5 | 3.8 | G5 | 2.9 |
| E5 | 2.1 | F6 | 4.3 |
| E6 | 3.1 | N5 | 2.9 |
| R5 | 5.8 | U5 | 6.2 |
| M6 | 3.1 | H6 | 6.8 |
| B6 | 2.7 | O5 | 4.3 |
| Z5 | 8.6 | N6 | 5.5 |
| F5 | 3.0 | I6 | 4.9 |
| X5 | 3.0 | W5 | 2.4 |
| J5 | 13.5 | O6 | 3.9 |

TABLE H

Fructose Enhancement at 50 μM

| Compound | EC50 Ratio | Compound | EC50 Ratio |
|---|---|---|---|
| Z5 | 2.9 | T5 | 3.4 |
| Q5 | 3.0 | F6 | 2.2 |
| A6 | 2.9 | U5 | 3.7 |
| L6 | 2.4 | H6 | 2.4 |
| Y5 | 2.2 | V5 | 2.4 |
| E6 | 2.5 | O5 | 2.6 |
| R5 | 2.1 | O6 | 2.6 |
| L5 | 2.0 | J5 | 4.1 (10 uM) |

Experiment 2

Sweet Flavor and Sweet Flavor Enhancement Measurement Using Human Panelists Conducting a Scaling Test Test samples containing experimental compounds were compared to a dose-response curve for perceived sweetness intensity of sweeteners (sucralose, sucrose, fructose and other sweeteners) concentrations to determine equivalent sweetness intensity.

A group of eight or more panelists tasted solutions including sweeteners at various concentrations, as well as the experimental compound both with and without added sweetener. Panelists then rated sweetness intensity of all samples on a structured horizontal line scale, anchored from 0 to 15, where 0 equals no sweetness and 15 equals equivalent sweetness to a 15% sucrose sample. Scores for sweetness intensity were averaged across panelists. Then using the average scores and/or equation of the line for the sweetener dose-response curve, equivalent sweetness concentrations were determined for the samples containing experimental compounds.

Subjects had been previously familiarized with the key attribute taste and were trained to use the 0 to 15 point line scale. Subjects refrained from eating or drinking (except water) for at least 1 hour prior to the test. Subjects ate a cracker and rinsed with water several times to clean the mouth.

Sweetener solutions are provided at a wide range of concentrations such as 100 ppm, 200 ppm, 300 ppm, 400 ppm, and 500 ppm for sucralose, or between 0% and 12% for sucrose or fructose, in order to create a dose-response curve. Samples containing experimental compound were prepared both alone and in a 100 ppm sucralose solution or a 6% sucrose or fructose solution. All samples were made up in low sodium buffer pH 7.1. In order to aid dispersion, solutions can be made up in 0.1% ethanol.

The solutions were dispensed in 20 ml volumes into 1 oz. sample cups and served to the subjects at room temperature. All samples were presented in randomized counterbalanced order to reduce response bias. Further, two sessions of testing may be used to check panel precision.

Subjects tasted each sample individually and rate sweetness intensity on the line scale prior to tasting the next sample. All samples were expectorated. Subjects may retaste the samples but can only use the volume of sample given. Subjects must rinse with water between samples. Eating an unsalted cracker between samples may be required depending on the samples tasted.

The scores for each sample were averaged across subjects and standard error was calculated. The dose-response curve was plotted graphically, and this may be used to ensure the panel is rating accurately; i.e., increasing the concentration of sucralose should correspond to increased average scores for sweetness. A 2-way ANOVA (factors being samples and panelists) and multiple comparison tests (such as Tukey's Honestly Significant Difference test) can be used to determine differences among samples and/or panelists. A 3-way ANOVA, with sessions as the third factor, can be used to determine if there is any difference in the ratings between sessions.

The results of human taste tests with Compound D5 are found below. Compound D5 is one of the examples described above. Table 1 indicates that 27.8 μM Compound D5 in 6% sucrose has sweetness equivalent to about between 10% sucrose and 12% sucrose

TABLE 1

Average Sweetness, n = 30 (15 Panelists × 2 rep). Tukey's Value = 1.023 (α = 0.05).

| Treatment | Average | SD | St Er | Tukey (5%) |
|---|---|---|---|---|
| 6% Sucrose | 6.6 | 1.3 | 0.2 | a |
| 8% Sucrose | 8.1 | 1.5 | 0.3 | b |
| 10% Sucrose | 9.8 | 1.4 | 0.3 | c |
| 6% Sucrose + 27.8 μM Compound D5 | 10.8 | 1.5 | 0.3 | cd |
| 12% Sucrose | 11.0 | 1.2 | 0.2 | d |

Experiment 3

Sweet Flavor and Sweet Flavor Enhancement Measurement Using Human Panelists Conducting a Paired Comparison Test Test samples containing experimental compounds are presented in pairs to the panelist and they are asked to determine which of the sample is sweeter. A group of 10-16 or more panelists participated in each test. Subjects refrained from eating or drinking (except water) for at least 1 hour prior to the test. Subjects rinsed with water several times to clean the mouth.

All samples are prepared with ethanol to ensure dispersion of the compound in solution. This includes samples without compound; all solutions are balanced for 0.1% ethanol.

Samples are also prepared with low sodium buffer (pH 7.1) in place of water. Buffer contains 0.952 g of KCl, 5.444 g of Na$_2$HPO$_4$, and 0.952 g of KH$_2$PO$_4$ in 40 L of DIUF water. Sample volumes are usually 20 ml.

In one paired comparison test, the panelist is presented with two different samples and asked to identify the sample which is sweeter. The samples within a paired comparison test are presented in a randomized, counterbalanced order. Panelists have up to a 1 minute delay between taste tests to clear the mouth of any tastes.

Binomial probability tables are used to determine the probability of the correct number of responses occurring for each test at alpha=0.05

The results of human taste tests with Compound D5 are found below. Table 2 indicates that panelists perceived 6% sucrose+27.8 µM Compound D5 as being significantly sweeter than a solution of 10% sucrose (p>0.05). Table 3 indicates that 27.8 µM Compound D5 alone has little or no sweetness on its own.

TABLE 2

| Sample selected as sweeter by panelists, n = 45 (15 panelists × 3 reps). | |
| --- | --- |
| Samples | Total |
| 10% Sucrose | 13 |
| 6% Sucrose + 27.8 µM Compound D5 | 32 |
| Total | 45 |
| 6% Sucrose + 27.8 µM Compound D5 (p-value) | 0.007 |

Table 3A indicates that 27.8 µM Compound D5 alone has little or no sweetness on its own. Table 3B indicates that 111.3 µM Compound D5 alone has little or no sweetness on its own.

TABLE 3A

| Sample selected as sweeter by panelists, n = 45 (15 panelists × 3 reps). | |
| --- | --- |
| Samples | Total |
| 1% Sucrose | 43 |
| LSB + 27.8 µM Compound D5 | 2 |
| Total | 45 |
| 1% Sucrose (p-value) | <0.001 |

TABLE 3B

| Sample selected as sweeter by panelists, n = 29 (16 panelists × 1 rep; 16 panelists × 1 rep ). | |
| --- | --- |
| Samples | Total |
| 1% Sucrose | 21 |
| LSB + 111.3 µM Compound D5 | 8 |
| Total | 29 |
| 1% Sucrose (p-value) | <0.024 |

The results of human taste tests with Compound K5 are found below. Table 4 indicates that panelists perceived 6% sucrose+27.9 µM Compound K5 as being significantly sweeter than a solution of 10% sucrose (p>0.05).

TABLE 4

| Sample selected as sweeter by panelists, n = 45 (15 panelists × 3 reps). | |
| --- | --- |
| Samples | Total |
| 10% Sucrose | 11 |
| 6% Sucrose + 27.9 µM Compound K5 | 34 |
| Total | 45 |
| 6% Sucrose + 27.9 µM compound K5 (p-value) | 0.001 |

The results of human taste tests with Compound Q5 are found below. Table 5 indicates that panelists perceived 6% sucrose+26.9 µM Compound Q5 as being significantly sweeter than a solution of 10% sucrose (p>0.05).

TABLE 5

| Sample selected as sweeter by panelists, n = 48 (16 panelists × 3 reps). | |
| --- | --- |
| Samples | Total |
| 10% Sucrose | 13 |
| 6% Sucrose + 26.9 µM Compound Q5 | 35 |
| Total | 48 |
| 6% Sucrose + 26.9 µM compound Q5 (p-value) | 0.002 |

The results of human taste tests with Compound A6 are found below. Table 6 indicates that panelists perceived 6% sucrose+26.9 µM Compound A6 as being significantly sweeter than a solution of 10% sucrose (p>0.05). Table 7 indicates that panelists perceived 6% High Fructose Corn Syrup+64.85 µM Compound A6 as being not significantly different in sweetness sweeter than a solution of 8% High Fructose Corn Syrup (p>0.05). Table 8 indicates that 64.8 M Compound A6 alone has little or no sweetness on its own.

TABLE 6

| Sample selected as sweeter by panelists, n = 45 (15 panelists × 3 reps). | |
| --- | --- |
| Samples | Total |
| 10% Sucrose | 9 |
| 6% Sucrose + 26.9 µM Compound A6 | 36 |
| Total | 45 |
| 6% Sucrose + 26.9 µM compound A6 (p-value) | 0.001 |

TABLE 7

| Sample selected as sweeter by panelists, n = 12 (12 panelists × 1 rep). | |
| --- | --- |
| Samples | Total |
| 8% High Fructose Corn Syrup | 8 |
| 6% High Fructose Corn Syrup + 64.8 µM Compound A6 | 4 |
| Total | 12 |
| 8% High Fructose Corn Syrup (p-value) | 0.388 |

TABLE 8

Sample selected as sweeter by panelists, n = 15 (15 panelists × 1 reps).

| Samples | Total |
| --- | --- |
| 1% High Fructose Corn Syrup | 14 |
| LSB + 64.8 µM Compound A6 | 1 |
| Total | 15 |
| 1% High Fructose Corn Syrup (p-value) | 0.001 |

The results of human taste tests with Compound L6 are found below. Table 9 indicates that panelists perceived 6% sucrose+26.8 µM Compound L6 as being significantly sweeter than a solution of 10% sucrose (p>0.05).

TABLE 9

Sample selected as sweeter by panelists, n = 45 (15 panelists × 3 reps).

| Samples | Total |
| --- | --- |
| 10% Sucrose | 14 |
| 6% Sucrose + 26.8 µM Compound L6 | 31 |
| Total | 45 |
| 6% Sucrose + 26.8 µM compound L6 (p-value) | 0.016 |

The results of human taste tests with Compound Y5 are found below. Table 10 indicates that panelists perceived 6% sucrose+27.8 µM Compound Y5 as being not significantly different in sweetness than a solution of 10% sucrose (p>0.05). Table 11 indicates that 27.8 µM Compound Y5 alone has little or no sweetness on its own.

TABLE 10

Sample selected as sweeter by panelists, n = 11 (11 panelists × 2 reps).

| Samples | Total |
| --- | --- |
| 10% Sucrose | 8 |
| 6% Sucrose + 27.8 µM Compound Y5 | 14 |
| Total | 22 |
| 6% Sucrose + 27.8 µM Compound Y5 (p-value) | 0.286 |

TABLE 11

Sample selected as sweeter by panelists, n = 45 (15 panelists × 3 reps).

| Samples | Total |
| --- | --- |
| 1% Sucrose | 44 |
| LSB + 27.8 µM Compound Y5 | 1 |
| Total | 45 |
| 1% Sucrose (p-value) | <0.001 |

The results of human taste tests with Compound E5 are found below. Table 12 indicates that panelists perceived 6% sucrose+24.9 µM Compound E5 as being not significantly different in sweetness than a solution of 10% sucrose (p>0.05).

TABLE 12

Sample selected as sweeter by panelists, n = 39 (13 panelists × 3 reps).

| Samples | Total |
| --- | --- |
| 10% Sucrose | 13 |
| 6% Sucrose + 24.9 µM Compound E5 | 26 |
| Total | 39 |
| 6% Sucrose + 24.9 µM Compound E5 (p-value) | 0.053 |

The results of human taste tests with Compound E6 are found below. Table 13 indicates that panelists perceived 6% sucrose+28.9 µM Compound E6 as being not significantly different in sweetness than a solution of 10% sucrose (p>0.05).

TABLE 13

Sample selected as sweeter by panelists, n = 39 (13 panelists × 3 reps).

| Samples | Total |
| --- | --- |
| 10% Sucrose | 18 |
| 6% Sucrose + 28.9 µM Compound E6 | 21 |
| Total | 39 |
| 6% Sucrose + 28.9 µM Compound E6 (p-value) | 0.053 |

The results of human taste tests with Compound R5 are found below. Table 14 indicates that panelists perceived 6% sucrose+26.9 µM Compound R5 as being not significantly different in sweetness than a solution of 10% sucrose (p>0.05).

TABLE 14

Sample selected as sweeter by panelists, n = 42 (14 panelists × 3 reps).

| Samples | Total |
| --- | --- |
| 10% Sucrose | 16 |
| 6% Sucrose + 26.9 µM Compound R5 | 26 |
| Total | 42 |
| 6% Sucrose + 26.9 µM Compound R5 (p-value) | 0.164 |

Experiment 4

Sweet Flavor and Sweet Flavor Enhancement Measurement Using Human Panelists Conducting a Paired Comparison Test with Compound D5 in Product Prototype Human panelists evaluated various drinks (e.g., tea, coffee, Kool-Aid) in paired comparison taste test procedure. Those drinks or precursors thereof were obtained from commercially available sources in non-sweetened forms and were prepared for testing by adding sucrose (sweetener) alone or adding sucrose (sweetener) and Compound D5 (sweetness enhancer) as indicated below.

Table 15 indicates that panelists perceived a Cherry flavored Kool-Aid sweetened with 5% sucrose+41.7 µM Compound D5 as being not significantly different in sweetness than a Cherry flavored Kool-Aid sweetened with 10% sucrose (p>0.05).

TABLE 15

| Sample selected as sweeter by panelists, n = 33 (11 panelists × 3 reps). | |
| --- | --- |
| Samples | Total |
| 10% Sucrose Cherry Kool-Aid | 18 |
| 5% Sucrose Cherry Kool-Aid + 41.7 μM Compound D5 | 15 |
| Total | 33 |
| 10% Sucrose Cherry Kool-Aid (p-value) | 0.728 |

Table 16 indicates that panelists perceived brewed Neutral Black Tea sweetened with 4% sucrose+30.6 μM Compound D5 as being not significantly different in sweetness than brewed Neutral Black Tea sweetened with 8% sucrose (p>0.05).

TABLE 16

| Sample selected as sweeter by panelists, n = 39 (13 panelists × 3 reps). | |
| --- | --- |
| Samples | Total |
| 8% Sucrose Brewed Neutral Black Tea | 22 |
| 4% Sucrose Brewed Neutral Black Tea + 30.6 μM Compound D5 | 17 |
| Total | 39 |
| 4% Sucrose Brewed Neutral Black Tea + 30.6 μM Compound D5 | 0.522 |

Table 17 indicates that panelists perceived a lemonade flavored Kool-Aid sweetened with 5% sucrose+41.7 μM Compound D5 as being not significantly different in sweetness than a lemonade flavored Kool-Aid sweetened with 10% sucrose (p>0.05).

TABLE 17

| Sample selected as sweeter by panelists, n = 48 (16 panelists × 3 reps). | |
| --- | --- |
| Samples | Total |
| 10% Sucrose Lemonade Kool-Aid | 27 |
| 5% Sucrose Lemonade Kool-Aid + 41.7 μM Compound D5 | 21 |
| Total | 48 |
| 10% Sucrose Lemonade Kool-Aid (p-value) | 0.471 |

Table 18 indicates that panelists perceived a Coffee Drink sweetened with 4% sucrose+23.65 μM Compound D5 as being not significantly different in sweetness than a Coffee Drink sweetened with 8% sucrose (p>0.05).

TABLE 18

| Sample selected as sweeter by panelists, n = 39 (13 panelists × 3 reps). | |
| --- | --- |
| Samples | Total |
| 8% Sucrose Coffee Drink | 20 |
| 4% Sucrose Coffee Drink + 23.65 μM Compound D5 | 19 |
| Total | 39 |
| 8% Sucrose Coffee Drink (p-value) | >0.871 |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A compound having structural Formula (I):

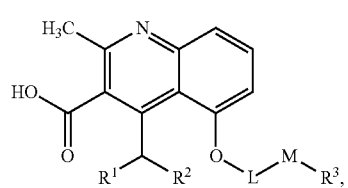

(I)

or a salt or solvate thereof; wherein
$R^1$ and $R^2$ are independently hydrogen or C1 to C6 alkyl;
L is optionally substituted C1 to C12 alkylene;
M is —$NR^4$—C(O)— or —C(O)—$NR^4$—;
$R^4$ is hydrogen or C1 to C6 alkyl; or alternatively, when M is —$NR^4$—C(O)—, $R^4$ and one or more atoms of L, together with the nitrogen to which they are attached, form an optionally substituted 5- to 8-membered heterocyclic ring; and
$R^3$ is optionally substituted C1 to C12 alkyl or optionally substituted 5- to 8-membered heterocyclyl,
wherein when a group is indicated as being optionally substituted, the one or more substituents are selected from the group consisting of halo, amino, N-alkyl amino, N,N-dialkyl amino, hydroxyl, alkoxy, alkyl, aryl, heteroaryl, heterocyclyl, carbocyclyl, =O, =S, =$NR^a$, =N—$OR^a$, —CN, —C(O)$R^b$, —C(O)$OR^a$, —C(=O)$NR^aR^a$, —OC(O)OH, —OC(O)$OR^a$, —$NR^a$C(O)$R^b$, —$NR^a$C(O)$OR^a$, and —$NR^a$C(O)$NR^aR^a$, wherein each $R^a$ is independently hydrogen or alkyl; or optionally two $R^a$, taken together with the nitrogen to which they are attached, form a heterocyclic ring; and each $R^b$ is alkyl.

2. The compound of claim 1, wherein $R^1$ and $R^2$ are both hydrogen.

3. The compound of claim 1, wherein the alkylene is straight, branched, cyclic, or a combination thereof.

4. The compound of claim 1, wherein the alkyl is straight, branched, cyclic, or a combination thereof.

5. The compound of claim 1, which is represented by structural Formula (Ia):

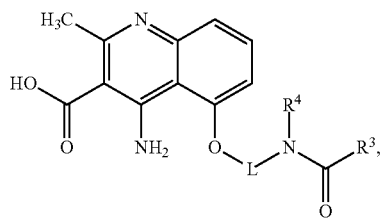

or a salt or solvate thereof, wherein,

L is optionally substituted C1 to C12 alkylene;

$R^4$ is hydrogen or C1 to C6 alkyl; or alternatively, $R^4$ and one or more atoms of L, together with the nitrogen to which they are attached, form an optionally substituted 5- to 8-membered heterocyclic ring; and $R^3$ is optionally substituted C1 to C12 alkyl or optionally substituted 5- to 8-membered heterocyclyl.

6. The compound of claim 1, which is represented by structural Formula (Ib):

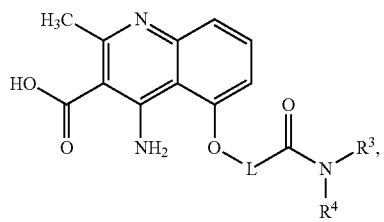

or a salt or solvate thereof, wherein:

L is optionally substituted C1 to C12 alkylene;

$R^4$ is hydrogen or C1 to C6 alkyl; and $R^3$ is optionally substituted C1 to C12 alkyl or optionally substituted 5- to 8-membered heterocyclyl.

7. The compound of claim 1, which is selected from the group consisting of

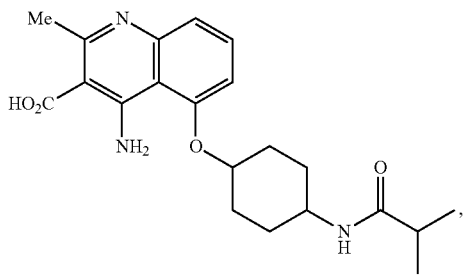

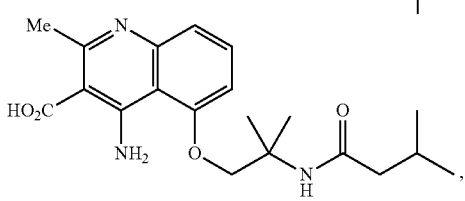

-continued

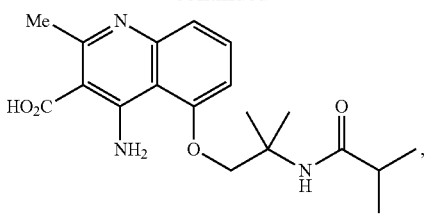

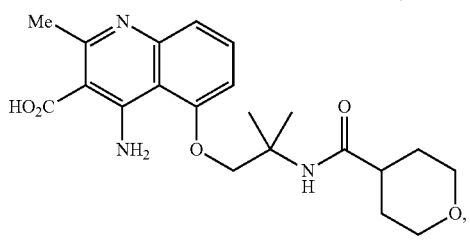

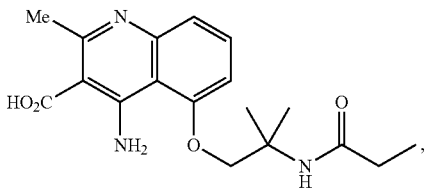

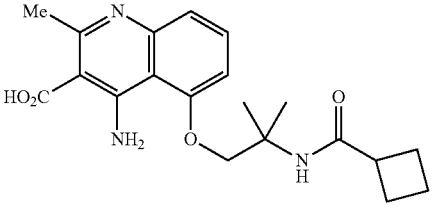

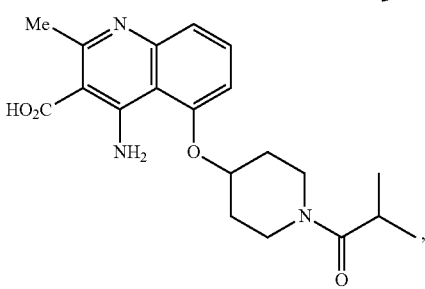

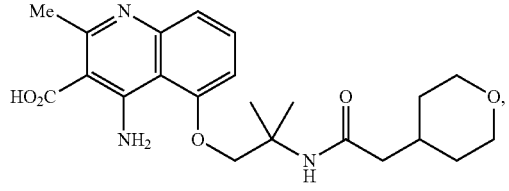

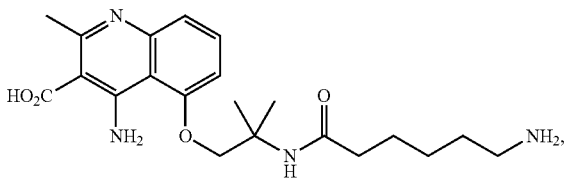

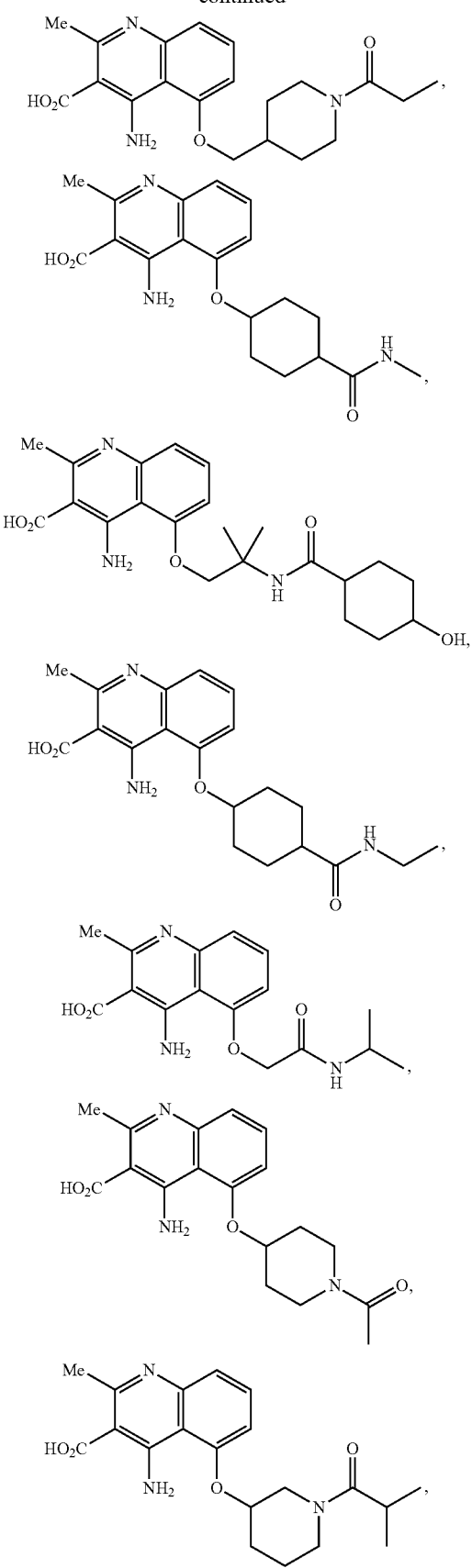
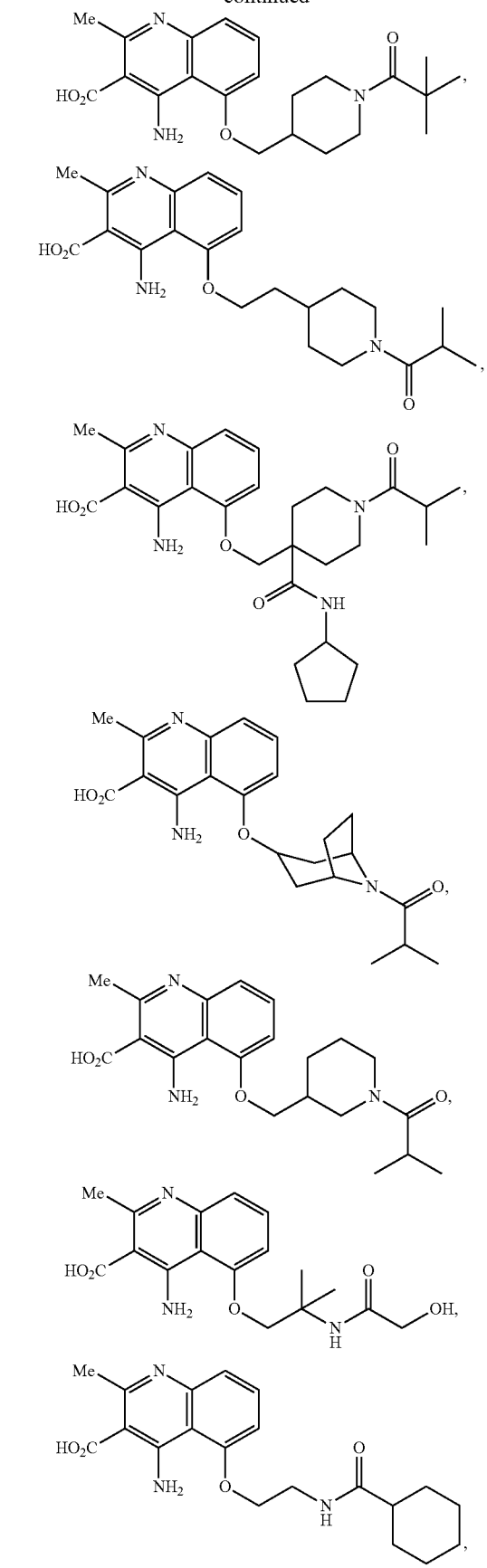

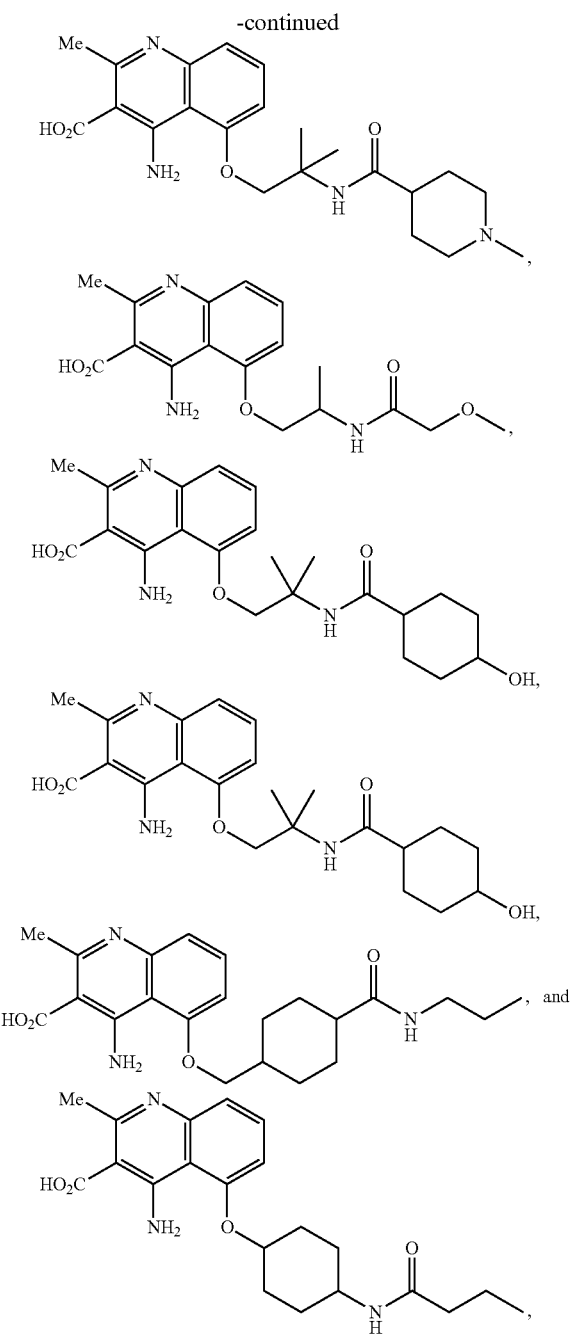

or a salt or solvate thereof.

8. The compound of claim 1, which enhances the sweetness of a sweetener at a pH from about 2.5 to about 8.5.

9. An ingestible composition comprising
a compound of claim 1; and optionally an ingestibly acceptable excipient.

10. The ingestible composition of claim 9, further comprising one or more sweeteners.

11. The ingestible composition of claim 10, wherein the sweetener is selected from the group consisting of sucrose, fructose, glucose, galactose, mannose, lactose, tagatose, maltose, corn syrup, D-tryptophan, glycine, erythritol, isomalt, lactitol, mannitol, sorbitol, xylitol, maltodextrin, maltitol, isomalt, hydrogenated glucose syrup (HGS), hydrogenated starch hydrolyzate (HSH), stevioside, rebaudioside A, other sweet Stevia-based glycosides, carrelame, other guanidine-based sweeteners, saccharin, acesulfame-K, cyclamate, sucralose, alitame, mogroside, neotame, aspartame, other aspartame derivatives, and combinations thereof.

12. The ingestible composition of claim 9, which is in form of a food or beverage product, a pharmaceutical composition, a nutritional product, a dietary supplement, over-the-counter medication, or oral care product.

13. The ingestible composition of claim 12, wherein the food or beverage product is selected from the group consisting of the Soup category; the Dried Processed Food category; the Beverage category; the Ready Meal category; the Canned or Preserved Food category; the Frozen Processed Food category; the Chilled Processed Food category; the Snack Food category; the Baked Goods category; the Confectionary category; the Dairy Product category; the Ice Cream category; the Meal Replacement category; the Pasta and Noodle category; the Sauces, Dressings, Condiments category; the Baby Food category; the Spreads category; sweet coatings, frostings, or glazes; and combinations thereof.

14. A method of increasing the sweet taste of a composition comprising contacting the composition thereof with a compound of claim 1 to form a modified composition.

15. A method of imparting a more sugar-like temporal profile and/or flavor profile to a sweetener composition comprising combining a compound of claim 1 and one or more sweetener in the sweetener composition.

16. A sweet enhancing composition, comprising a compound of claim 1 in an amount effective to provide sweetening in combination with a first amount of sweetener, wherein the sweetening is more than the sweetening provided by the first amount of sweetener without the compound.

17. An ingestible composition comprising the sweet enhancing composition of claim 16.

18. The ingestible composition of claim 17, which is in form of a food or beverage product, a pharmaceutical composition, a nutritional product, a dietary supplement, over-the-counter medication, or oral care product.

19. A flavoring concentrate formulation comprising
i) as flavor modifying ingredient, a compound of claim 1;
ii) a carrier; and
iii) optionally at least one adjuvant.

20. The flavoring concentrate formulation of claim 19, wherein the at least one adjuvant comprises one or more flavoring agents.

21. The flavoring concentrate formulation of claim 19, wherein the at least one adjuvant comprises one or more sweeteners.

22. The flavoring concentrate formulation of claim 19, wherein the at least one adjuvant comprises one or more ingredients selected from the group consisting of a emulsifier, a stabilizer, an antimicrobial preservative, an antioxidant, vitamins, minerals, fats, starches, protein concentrates and isolates, salts, a freezing point depressant, nucleating agent, and combinations thereof.

23. The flavoring concentrate formulation of claim 19, which is in a form selected from the group consisting of liquid, solid, semi-solid, foamy material, paste, gel, cream, lotion, and combinations thereof.

24. The compound of claim 1, wherein $R^4$ is hydrogen or C1 to C6 alkyl.

25. The compound of claim 1, wherein M is —$NR^4$—C(O)—; and $R^4$ and one or more atoms of L, together with the nitrogen to which they are attached, form an optionally substituted 5- to 8-membered heterocyclic ring.

26. The compound of claim 1, which is selected from the group consisting of

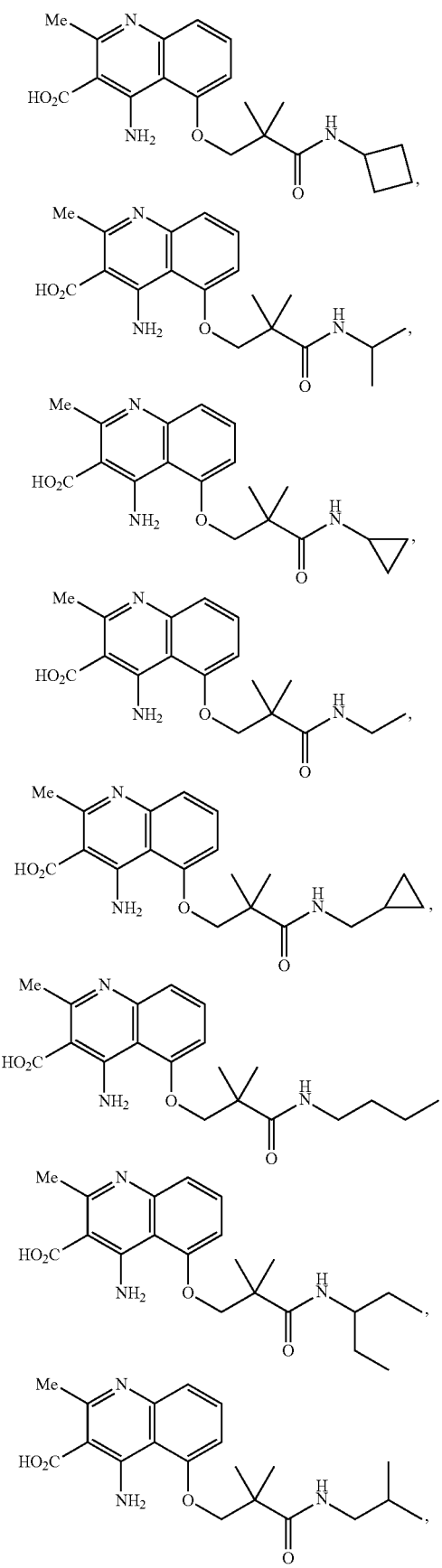
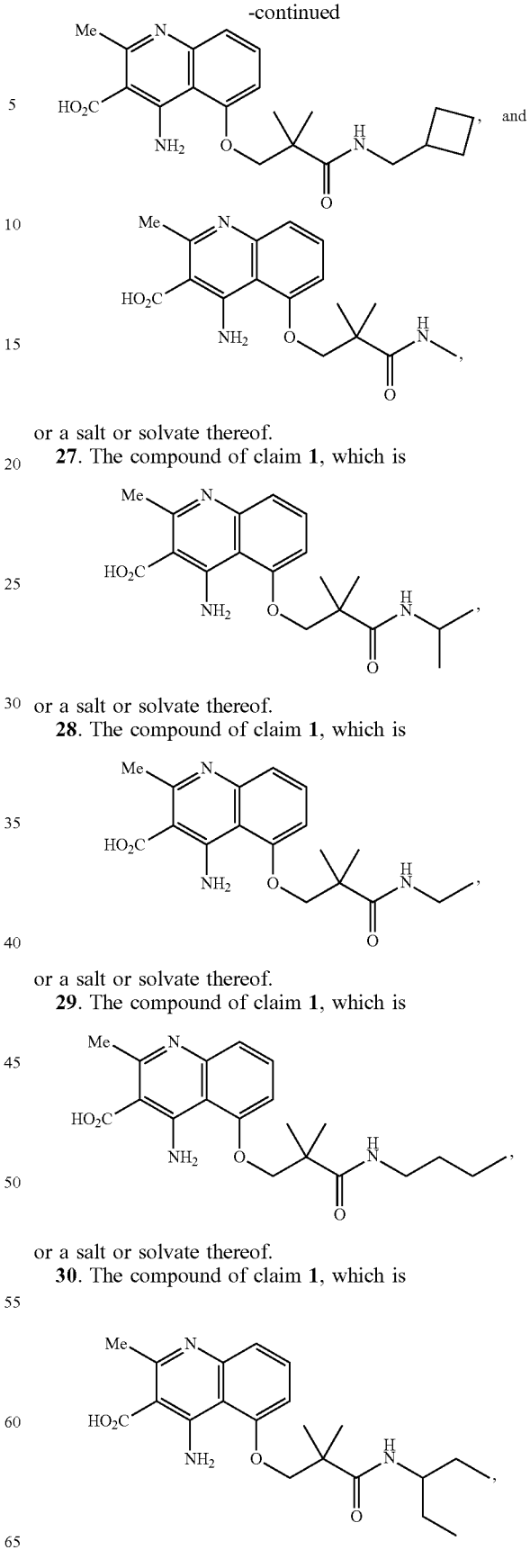
or a salt or solvate thereof.
27. The compound of claim 1, which is
or a salt or solvate thereof.
28. The compound of claim 1, which is
or a salt or solvate thereof.
29. The compound of claim 1, which is
or a salt or solvate thereof.
30. The compound of claim 1, which is
or a salt or solvate thereof.

31. The compound of claim 1, which is
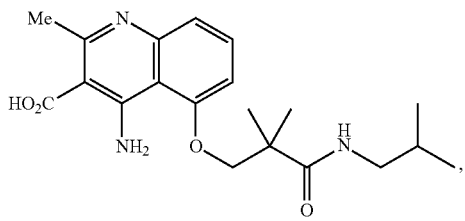 [SMILES: Cc1nc2cccc(OCC(C)(C)C(=O)NCC(C)C)c2c(N)c1C(=O)O]
or a salt or solvate thereof.
32. The compound of claim 1, which is
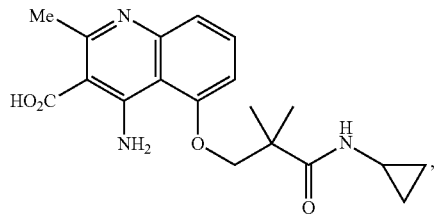 [SMILES: Cc1nc2cccc(OCC(C)(C)C(=O)NC3CC3)c2c(N)c1C(=O)O]
or a salt or solvate thereof.
* * * * *